(12) United States Patent
Alemparte-Gallardo et al.

(10) Patent No.: US 8,097,628 B2
(45) Date of Patent: Jan. 17, 2012

(54) COMPOUNDS

(75) Inventors: Carlos Alemparte-Gallardo, Madrid (ES); Christopher Barfoot, Stevenage (GB); David Barros-Aguirre, Madrid (ES); Monica Cacho-Izquierdo, Madrid (ES); Jose Maria Fiandor Roman, Madrid (ES); Alan Joseph Hennessy, Stevenage (GB); Neil David Pearson, Collegeville, PA (US); Modesto Jesus Remuinan-Blanco, Madrid (ES)

(73) Assignee: Glaxo Group Limited, Greenford, Middlesex (GB)

( * ) Notice: Subject to any disclaimer, the term of this patent is extended or adjusted under 35 U.S.C. 154(b) by 275 days.

(21) Appl. No.: 12/469,767

(22) Filed: May 21, 2009

(65) Prior Publication Data

US 2009/0306089 A1  Dec. 10, 2009

(30) Foreign Application Priority Data

May 23, 2008 (EP) .................................. 08382018
Oct. 17, 2008 (EP) .................................. 08382044
Oct. 17, 2008 (EP) .................................. 08382057

(51) Int. Cl.
| | |
|---|---|
| *C07D 471/00* | (2006.01) |
| *C07D 487/00* | (2006.01) |
| *C07D 491/00* | (2006.01) |
| *C07D 495/00* | (2006.01) |
| *C07D 497/00* | (2006.01) |
| *C07D 498/00* | (2006.01) |
| *C07D 513/00* | (2006.01) |
| *C07D 515/00* | (2006.01) |
| *A01N 43/58* | (2006.01) |
| *A01N 43/60* | (2006.01) |
| *A01N 43/42* | (2006.01) |
| *A01N 43/40* | (2006.01) |
| *A01N 43/52* | (2006.01) |
| *A61K 31/50* | (2006.01) |
| *A61K 31/495* | (2006.01) |
| *A61K 31/497* | (2006.01) |
| *A61K 31/4965* | (2006.01) |
| *A61K 31/44* | (2006.01) |
| *A61K 31/415* | (2006.01) |

(52) U.S. Cl. .............. 514/250; 514/252.11; 514/255.05; 514/292; 514/293; 514/334; 514/393; 546/81; 546/82; 544/344; 544/345; 544/346

(58) Field of Classification Search .................. 514/250, 514/252.11, 255.05, 292, 293, 334, 393; 544/344, 345, 346; 546/81, 82
See application file for complete search history.

(56) References Cited

FOREIGN PATENT DOCUMENTS

| | | |
|---|---|---|
| WO | 2007/071936 | 6/2007 |
| WO | 2007/115947 | 10/2007 |

OTHER PUBLICATIONS

P. Remuzon, et al.; Fluoronaphthyridines and -quinolones as antibacterial agents; J. Med. Chem. 34(1):29-37, 1991.

*Primary Examiner* — Sreeni Padmanabhan
*Assistant Examiner* — Sarah Pihonak
(74) *Attorney, Agent, or Firm* — Bonnie L. Deppenbrock

(57) ABSTRACT

Compounds of Formula (I) or pharmaceutically acceptable salts or N-oxides thereof:

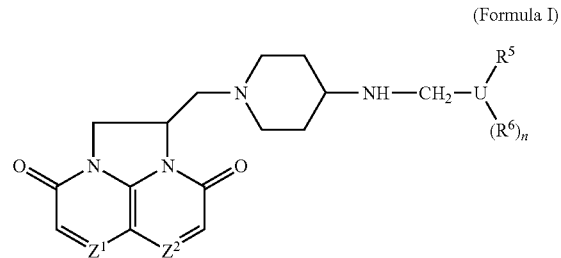

(Formula I)

(relative chemistry shown) pharmaceutical compositions comprising them, their use in therapy especially against tuberculosis, and methods of preparing them are described.

19 Claims, No Drawings

COMPOUNDS

FIELD OF THE INVENTION

This invention relates to compounds, compositions containing them, their use in therapy, including their use as antibacterials, for example in the treatment of tuberculosis, and methods for the preparation of such compounds.

BACKGROUND OF THE INVENTION

PCT patent publications WO02/08224, WO02/50061, WO02/56882, WO02/96907, WO2003087098, WO2003010138, WO2003064421, WO2003064431, WO2004002992, WO2004002490, WO2004014361, WO2004041210, WO2004096982, WO2002050036, WO2004058144, WO2004087145, WO2006002047, WO2006014580, WO2006010040, WO2006017326, WO2006012396, WO2006017468, WO2006020561, WO2006081179, WO2006081264, WO2006081289, WO2006081178, WO2006081182, WO01/25227, WO02/40474, WO02/07572, WO2004024712, WO2004024713, WO2004035569, WO2004087647, WO2004089947, WO2005016916, WO2005097781, WO2006010831, WO2006021448, WO2006032466, WO2006038172, WO2006046552, WO2006099884, WO2006105289, WO2006081178, WO2006081182, WO2006134378, WO 2006137485, WO2007016610, WO2007081597, WO2007071936, WO2007115947, WO2007118130, WO2007122258, WO2007138974, WO2008006648, WO2008 003690, and WO2008009700 disclose quinoline, naphthyridine, morpholine, cyclohexane, piperidine and piperazine derivatives and also tricyclic condensed ring compounds, having antibacterial activity. WO2004104000 discloses tricyclic condensed ring compounds capable of selectively acting on cannabinoid receptors.

Synthetic drugs for treating tuberculosis (TB) have been available for over half a century, but incidences of the disease continue to rise world-wide. In 2004, it is estimated that 24,500 people developed active disease and close to 5,500 died each day from TB (World Health Organization, Global Tuberculosis Control: Surveillance, Planning, Financing. WHO Report 2006, Geneva, Switzerland, ISBN 92-4 156314-1). Co-infection with HIV is driving the increase in incidence (Williams, B. G.; Dye, C. *Science,* 2003, 301, 1535) and the cause of death in 31% of AIDS patients in Africa can be attributed to TB (Corbett, E. L.; Watt, C. J.; Catherine, J.; Walker, N.; Maher D.; Williams, B. G.; Raviglione, M. C.; Dye, C. *Arch. Intl. Med.,* 2003, 163, 1009, Septkowitz, A.; Raffalli, J.; Riley, T.; Kiehn, T. E.; Armstrong, D. *Clin. Microbiol. Rev.* 1995, 8, 180). When coupled with the emergence of multi-drug resistant strains of *Mycobacterium tuberculosis* (MDR-TB), the scale of the problem is amplified. It is now more than a decade since the WHO declared TB "a global health emergency" (World Health Organization, Global Tuberculosis Control: Surveillance, Planning, Financing. WHO Report 2006, Geneva, Switzerland, ISBN 92-4 156314-1).

The limitations of tuberculosis therapy and prevention are well known. The current available vaccine, BCG was introduced in 1921 and fails to protect most people past childhood. Patients who do become infected with active disease currently endure combination therapy with isoniazid, rifampin, pyrazinamide and ethambutol for two months and then continue taking isoniazid and rifampin for a further four months. Daily dosing is required and poor compliance drives the emergence and spread of multi-drug-resistant strains, which are challenging to treat. A recently published detailed review discusses many aspects of TB such as pathogenesis, epidemiology, drug discovery and vaccine development to date (Nature Medicine, Vol 13(3), pages 263-312).

Shorter courses of more active agents which can be taken less frequently and which present a high barrier to the emergence of resistance, i.e. agents which are effective against multi-drug resistant strains of TB (MDR-TB), are urgently required. There is therefore a need to discover and develop new chemical entities to treat TB (recent synthetic leads are reviewed in: Ballell, L.; Field, R. A.; Duncan, K.; Young, R. J. *Antimicrob. Agents Chemother.* 2005, 49, 2153).

DETAILED DESCRIPTION OF THE INVENTION

In one aspect the present invention provides a compound of Formula (I) or a pharmaceutically acceptable salt or N-oxide thereof:

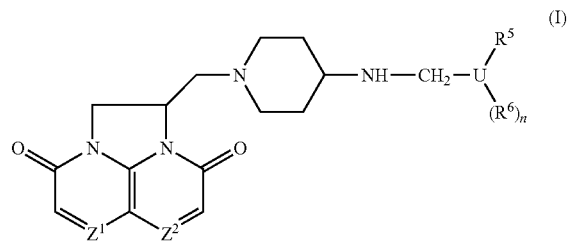

(I)

wherein:
one of $Z^1$ and $Z^2$ is CH or N and the other is CH;
U represents a group selected from: phenyl, pyridyl, pyridazinyl, pyrimidinyl, pyrazinyl, thiazolyl, furanyl, imidazolyl and thiophenyl;
n is 0 or 1;
$R^5$ and $R^6$ are independently selected from: halo, $CF_3$, $OCF_3$, $C_{1-3}$ alkyl, $NHR^7$, $NR^{7A}R^{7B}$, $C_{1-3}$ alkoxy, nitro and cyano; or $R^5$ may be a group —$C_mH_{2m}$-A where m is 1-5 and the moiety —$C_mH_{2m}$— may be straight or branched chain and A is selected from OH, $OR^7$, $OCOR^7$, $OCO_2R^7$, $OCONR^7$, $OPO_2R^7$ and $NH_2$, where each $R^7$, $R^{7A}$ and $R^{7B}$ is independently $C_{1-5}$ alkyl.

In one embodiment a compound of Formula (I) may be a compound of Formula (IA) or a pharmaceutically acceptable salt or N-oxide thereof:

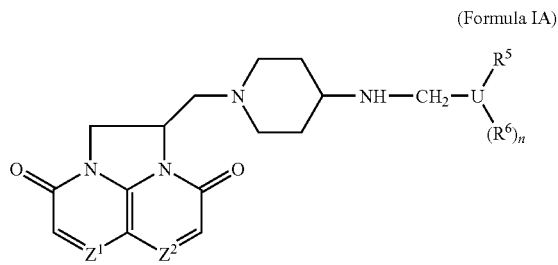

(Formula IA)

wherein:
one of $Z^1$ and $Z^2$ is CH or N and the other is CH;
U represents a group selected from: phenyl, pyridyl, pyridazinyl, pyrimidinyl, pyrazinyl, thiazolyl, furanyl, imidazolyl and thiophenyl;
$R^5$ and $R^6$ are independently selected from: halo, $CF_3$, $OCF_3$, $C_{1-3}$ alkyl, $C_{1-3}$ alkoxy, nitro and cyano, and n is 0 or 1.

The invention further provides a pharmaceutical composition comprising a compound of Formula (I), or a pharmaceutically acceptable salt or N-oxide thereof, and one or more pharmaceutically acceptable carriers, excipients or diluents.

The invention also provides a method of treatment of tuberculosis in mammals, particularly in man, which method comprises the administration to a mammal in need of such treatment an effective amount of a compound of Formula (I), or a pharmaceutically acceptable salt or N-oxide thereof.

This invention further provides a method of treatment of bacterial infections in mammals, particularly in man, which method comprises the administration to a mammal in need of such treatment an effective amount of a compound of Formula (I), or a pharmaceutically acceptable salt or N-oxide thereof.

The invention further provides a compound of Formula (I), or a pharmaceutically acceptable salt or N-oxide thereof, for use in therapy.

The invention yet further provides a compound of Formula (I), or a pharmaceutically acceptable salt or N-oxide thereof, for use in the treatment of tuberculosis in mammals, particularly in man.

The invention yet further provides a compound of Formula (I), or a pharmaceutically acceptable salt or N-oxide thereof, for use in the treatment of bacterial infections in mammals, particularly in man.

The invention still further provides the use of a compound of Formula (I), or a pharmaceutically acceptable salt or N-oxide thereof, in the manufacture of a medicament for use in the treatment of tuberculosis in mammals, particularly in man.

The invention still further provides the use of a compound of Formula (I), or a pharmaceutically acceptable salt or N-oxide thereof, in the manufacture of a medicament for use in the treatment of bacterial infections in mammals, particularly in man.

The invention also provides a pharmaceutical composition comprising a compound of Formula (I), or a pharmaceutically acceptable salt or N-oxide thereof, and one or more pharmaceutically acceptable carriers, excipients or diluents, for use in the treatment of tuberculosis in mammals, particularly in man.

The invention also provides a pharmaceutical composition comprising a compound of Formula (I), or a pharmaceutically acceptable salt or N-oxide thereof, and one or more pharmaceutically acceptable carriers, excipients or diluents, for use in the treatment of bacterial infections in mammals, particularly in man.

In one embodiment of the invention, U represents a group selected from: phenyl, pyridyl, pyridazinyl, pyrimidinyl, thienyl, thiazolyl, or thiophenyl. In another embodiment, U represents a group selected from: phenyl, pyridyl, pyridazinyl, thiazolyl, and thiophenyl.

In one embodiment of the invention, when n=0, $R^5$ represents $CF_3$, $OCF_3$, Cl, Br, or $NO_2$.

In one embodiment of the invention n=1 and one of $R^5$ and $R^6$ represents Cl and the other represents Cl, $CH_3$, $C_2H_5$, CN, $CF_3$ or $OCF_3$.

In one embodiment of the invention n=1 and one of $R^5$ and $R^6$ represents F and the other represents Cl, $CF_3$, CN, $CH_3$, or $C_2H_5$.

In one embodiment of the invention n=1 and one of $R^5$ and $R^6$ represents $CH_3$ and the other represents Br, $CH_3$, $CF_3$, CN or $NO_2$.

In one embodiment of the invention n is 0 and $R^5$ represents $CF_3$.

In one embodiment of the invention n is 1 and $R^5$ and $R^6$ represent Cl and $CH_3$.

In one embodiment of the invention n is 1 and $R^5$ and $R^6$ represent $CH_3$ and $CF_3$.

In one embodiment of the invention n is 1 and $R^5$ and $R^6$ represent Cl and CN.

In one embodiment of the invention m is 1 and A is —OH so $R^5$ represents —$CH_2$—OH, n is 1 and $R^6$ is Cl.

In one embodiment of the invention, when U represents a group selected from: phenyl, pyridyl or pyridazinyl n=0, then $R^5$ is in the para position of U relative to the bond between U and the $CH_2$ group to which it is bonded.

In one embodiment of the invention, when U represents a group selected from: phenyl or pyridyl, and n=1, one of $R^5$ and $R^6$ is in the para position, and the other in the meta position of U relative to the bond between U and the $CH_2$ group to which it is bonded.

One or more of the above structural embodiments may be present in a compound of Formula (I).

In an embodiment of the invention, the absolute stereochemistry of the compound of Formula (I) or (IA) is indicated by the Formula (IB):

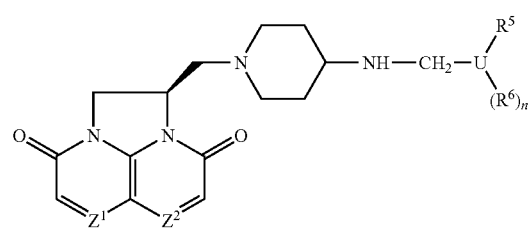

(Formula IB)

Compounds of Formula (I) may exist in the form of salts, solvates or N-oxides, and Formula (I) encompasses these forms.

In one aspect, compounds which are useful in the present invention include those mentioned in the Examples and their pharmaceutically acceptable salts, solvates or N-oxides.

In another aspect, compounds which are useful in the present invention include:

(1R)-1-[(4-{[(5-chloro-6-methyl-3-pyridinyl)methyl]amino}-1-piperidinyl)methyl]-1,2-dihydro-4H,9H-imidazo[1,2,3-ij]-1,8-naphthyridine-4,9-dione;

(2R)-2-[(4-{[(5-chloro-6-methyl-3-pyridinyl)methyl]amino}-1-piperidinyl)methyl]-1,2-dihydro-3H,8H-2a,5,8a-triazaacenaphthylene-3,8-dione;

(2R)-2-[(4-{[(3,4-dichlorophenyl)methyl]amino}-1-piperidinyl)methyl]-1,2-dihydro-3H,8H-2a,5,8a-triazaacenaphthylene-3,8-dione;

(2R)-2-{[4-({[4-fluoro-3-(trifluoromethyl)phenyl]methyl}amino)-1-piperidinyl]methyl}-1,2-dihydro-3H,8H-2a,5,8a-triazaacenaphthylene-3,8-dione;

5-{[(1-{[(2R)-3,8-dioxo-1,2-dihydro-3H,8H-2a,5,8a-triazaacenaphthylen-2-yl]methyl}-4-piperidinyl)amino]methyl}-2-fluorobenzonitrile;

(2R)-2-[(4-{[(4-fluoro-3-methylphenyl)methyl]amino}-1-piperidinyl)methyl]-1,2-dihydro-3H,8H-2a,5,8a-triazaacenaphthylene-3,8-dione;

(1R)-1-[(4-{[(5-chloro-4-methyl-2-pyridinyl)methyl]amino}-1-piperidinyl)methyl]-1,2-dihydro-4H,9H-imidazo[1,2,3-ij]-1,8-naphthyridine-4,9-dione;

(1R)-1-[(4-{[(5-chloro-6-methyl-3-pyridinyl)methyl]amino}-1-piperidinyl)methyl]-1,2-dihydro-3H,8H-2a,5,8a-triazaacenaphthylene-3,8-dione;

(1R)-1-{[4-({[6-(trifluoromethyl)-3-pyridinyl]
methyl}amino)-1-piperidinyl]methyl}-1,2-dihydro-4H,
9H-imidazo[1,2,3-ij]-1,8-naphthyridine-4,9-dione;
(1R)-1-{[4-({[6-(trifluoromethyl)-3-pyridinyl]
methyl}amino)-1-piperidinyl]methyl}-1,2-dihydro-3H,
8H-2a,5,8a-triazaacenaphthylene-3,8-dione;
(1R)-1-{[4-({[6-(trifluoromethyl)-3-pyridinyl]
methyl}amino)-1-piperidinyl]methyl}-1,2-dihydro-3H,
8H-2a,5,8a-triazaacenaphthylene-3,8-dione;
(1R)-1-[(4-{[(5-bromo-6-methyl-3-pyridinyl)methyl]
amino}-1-piperidinyl)methyl]-1,2-dihydro-4H,9H-imidazo[1,2,3-ij]-1,8-naphthyridine-4,9-dione;
(1R)-1-[(4-{[(5,6-dimethyl-3-pyridinyl)methyl]amino}-1-piperidinyl)methyl]-1,2-dihydro-4H,9H-imidazo[1,2,3-ij]-1,8-naphthyridine-4,9-dione;
2-[(4-{[(5,6-dimethyl-3-pyridinyl)methyl]amino}-1-piperidinyl)methyl]-1,2-dihydro-3H,8H-2a,5,8a-triazaacenaphthylene-3,8-dione;
2-[(4-{[(5,6-dichloro-3-pyridinyl)methyl]amino}-1-piperidinyl)methyl]-1,2-dihydro-3H,8H-2a,5,8a-triazaacenaphthylene-3,8-dione;
2-{[4-({[4-chloro-3-(trifluoromethyl)phenyl]
methyl}amino)-1-piperidinyl]methyl}-1,2-dihydro-3H,
8H-2a,5,8a-triazaacenaphthylene-3,8-dione;
2-{[4-({[6-(trifluoromethyl)-3-pyridazinyl]methyl}amino)-1-piperidinyl]methyl}-1,2-dihydro-3H,8H-2a,5,8a-triazaacenaphthylene-3,8-dione;
(1R)-1-{[4-({[6-(trifluoromethyl)-3-pyridazinyl]
methyl}amino)-1-piperidinyl]methyl}-1,2-dihydro-4H,
9H-imidazo[1,2,3-ij]-1,8-naphthyridine-4,9-dione;
2-{[4-({[6-(trifluoromethyl)-3-pyridinyl]methyl}amino)-1-piperidinyl]methyl}-1,2-dihydro-3H,8H-2a,5,8a-triazaacenaphthylene-3,8-dione;
2-{[4-({[6-(trifluoromethyl)-3-pyridinyl]methyl}amino)-1-piperidinyl]methyl}-1,2-dihydro-3H,8H-2a,5,8a-triazaacenaphthylene-3,8-dione;
2-[(4-{[(4-chlorophenyl)methyl]amino}-1-piperidinyl)methyl]-1,2-dihydro-3H,8H-2a,5,8a-triazaacenaphthylene-3,8-dione;
2-[(4-{[(3-chlorophenyl)methyl]amino}-1-piperidinyl)methyl]-1,2-dihydro-3H,8H-2a,5,8a-triazaacenaphthylene-3,8-dione;
2-[(4-{[(4-methyl-3-nitrophenyl)methyl]amino}-1-piperidinyl)methyl]-1,2-dihydro-3H,8H-2a,5,8a-triazaacenaphthylene-3,8-dione;
2-[(4-{[(5-bromo-4-methyl-2-thienyl)methyl]amino}-1-piperidinyl)methyl]-1,2-dihydro-3H,8H-2a,5,8a-triazaacenaphthylene-3,8-dione;
2-[(4-{[(3,4-dimethylphenyl)methyl]amino}-1-piperidinyl)methyl]-1,2-dihydro-3H,8H-2a,5,8a-triazaacenaphthylene-3,8-dione;
2-[(4-{[(5-chloro-6-methyl-3-pyridinyl)methyl]amino}-1-piperidinyl)methyl]-1,2-dihydro-3H,8H-2a,5,8a-triazaacenaphthylene-3,8-dione;
2-({4-[({4-[(trifluoromethyl)oxy]phenyl}methyl)amino]-1-piperidinyl}methyl)-1,2-dihydro-3H,8H-2a,5,8a-triazaacenaphthylene-3,8-dione;
2-{[4-({[4-(trifluoromethyl)phenyl]methyl}amino)-1-piperidinyl]methyl}-1,2-dihydro-3H,8H-2a,5,8a-triazaacenaphthylene-3,8-dione;
2-[(4-{[(4-bromophenyl)methyl]amino}-1-piperidinyl)methyl]-1,2-dihydro-3H,8H-2a,5,8a-triazaacenaphthylene-3,8-dione;
2-[(4-{[(5-chloro-6-methyl-3-pyridinyl)methyl]amino}-1-piperidinyl)methyl]-1,2-dihydro-3H,8H-2a,5,8a-triazaacenaphthylene-3,8-dione;

(1R)-1-[(4-{[(3,4-dichlorophenyl)methyl]amino}-1-piperidinyl)methyl]-1,2-dihydro-4H,9H-imidazo[1,2,3-ij]-1,8-naphthyridine-4,9-dione;
5-{[(1-{[(1R)-4,9-dioxo-1,2-dihydro-4H,9H-imidazo[1,2,3-ij]-1,8-naphthyridin-1-yl]methyl}-4-piperidinyl)amino]methyl}-3-methyl-2-pyridinecarbonitrile;
2-[(4-{[(6-fluoro-5-methyl-3-pyridinyl)methyl]amino}-1-piperidinyl)methyl]-1,2-dihydro-3H,8H-2a,5,8a-triazaacenaphthylene-3,8-dione;
2-[(4-{[(4-chloro-3-methylphenyl)methyl]amino}-1-piperidinyl)methyl]-1,2-dihydro-3H,8H-2a,5,8a-triazaacenaphthylene-3,8-dione;
2-[(4-{[(4-bromo-2-thienyl)methyl]amino}-1-piperidinyl)methyl]-1,2-dihydro-3H,8H-2a,5,8a-triazaacenaphthylene-3,8-dione;
2-[(4-{[(3,4-dichlorophenyl)methyl]amino}-1-piperidinyl)methyl]-1,2-dihydro-3H,8H-2a,5,8a-triazaacenaphthylene-3,8-dione;
2-[(4-{[(2-chloro-1,3-thiazol-5-yl)methyl]amino}-1-piperidinyl)methyl]-1,2-dihydro-3H,8H-2a,5,8a-triazaacenaphthylene-3,8-dione;
2-[(4-{[(4-nitrophenyl)methyl]amino}-1-piperidinyl)methyl]-1,2-dihydro-3H,8H-2a,5,8a-triazaacenaphthylene-3,8-dione;
2-{[4-({[3-chloro-4-(methyloxy)phenyl]methyl}amino)-1-piperidinyl]methyl}-1,2-dihydro-3H,8H-2a,5,8a-triazaacenaphthylene-3,8-dione;
2-[(4-{[(5-bromo-2-pyridinyl)methyl]amino}-1-piperidinyl)methyl]-1,2-dihydro-3H,8H-2a,5,8a-triazaacenaphthylene-3,8-dione;
2-[(4-{[(5-bromo-3-pyridinyl)methyl]amino}-1-piperidinyl)methyl]-1,2-dihydro-3H,8H-2a,5,8a-triazaacenaphthylene-3,8-dione;
2-[(4-{[(5-chloro-3-pyridinyl)methyl]amino}-1-piperidinyl)methyl]-1,2-dihydro-3H,8H-2a,5,8a-triazaacenaphthylene-3,8-dione;
2-[(4-{[(3-fluoro-4-methylphenyl)methyl]amino}-1-piperidinyl)methyl]-1,2-dihydro-3H,8H-2a,5,8a-triazaacenaphthylene-3,8-dione;
2-[(4-{[(3,4-difluorophenyl)methyl]amino}-1-piperidinyl)methyl]-1,2-dihydro-3H,8H-2a,5,8a-triazaacenaphthylene-3,8-dione;
(2R)-2-{[4-({[6-(trifluoromethyl)-3-pyridinyl]
methyl}amino)-1-piperidinyl]methyl}-1,2-dihydro-3H,
8H-2a,5,8a-triazaacenaphthylene-3,8-dione;
(2R)-2-{[4-({[6-(trifluoromethyl)-3-pyridinyl]
methyl}amino)-1-piperidinyl]methyl}-1,2-dihydro-3H,
8H-2a,5,8a-triazaacenaphthylene-3,8-dione hydrochloride;
(2S)-2-[(4-{[(3,4-dichlorophenyl)methyl]amino}-1-piperidinyl)methyl]-1,2-dihydro-3H,8H-2a,5,8a-triazaacenaphthylene-3,8-dione;
(2S)-2-{[4-({[6-(trifluoromethyl)-3-pyridinyl]
methyl}amino)-1-piperidinyl]methyl}-1,2-dihydro-3H,
8H-2a,5,8a-triazaacenaphthylene-3,8-dione;
3-chloro-5-{[(1-{[(1R)-4,9-dioxo-1,2-dihydro-4H,9H-imidazo[1,2,3-ij]-1,8-naphthyridin-1-yl]methyl}-4-piperidinyl)amino]methyl}-2-pyridinecarbonitrile;
3-chloro-5-{[(1-{[(1R)-4,9-dioxo-1,2-dihydro-4H,9H-imidazo[1,2,3-ij]-1,8-naphthyridin-1-yl]methyl}-4-piperidinyl)amino]methyl}-2-pyridinecarbonitrile dihydrochloride;
(2R)-2-[(4-{[(5-bromo-6-methyl-3-pyridinyl)methyl]
amino}-1-piperidinyl)methyl]-1,2-dihydro-3H,8H-2a,5,
8a-triazaacenaphthylene-3,8-dione;

2-[(4-{[(5-fluoro-6-methyl-3-pyridinyl)methyl]amino}-1-piperidinyl)methyl]-1,2-dihydro-3H,8H-2a,5,8a-triazaacenaphthylene-3,8-dione;

(2S)-2-[(4-{[(5-chloro-6-methyl-3-pyridinyl)methyl]amino}-1-piperidinyl)methyl]-1,2-dihydro-3H,8H-2a,5,8a-triazaacenaphthylene-3,8-dione;

(1R)-1-[(4-{[(6-ethyl-5-fluoro-3-pyridinyl)methyl]amino}-1-piperidinyl)methyl]-1,2-dihydro-4H,9H-imidazo[1,2,3-ij]-1,8-naphthyridine-4,9-dione;

(1R)-1-[(4-{[(5-bromo-6-methyl-3-pyridinyl)methyl]amino}-1-piperidinyl)methyl]-1,2-dihydro-3H,8H-2a,5,8a-triazaacenaphthylene-3,8-dione hydrochloride;

(1R)-1-{[4-({[5-chloro-6-(hydroxymethyl)-3-pyridinyl]methyl}amino)-1-piperidinyl]methyl}-1,2-dihydro-4H,9H-imidazo[1,2,3-ij]-1,8-naphthyridine-4,9-dione;

2-{[4-({[4-methyl-3-(methyloxy)phenyl]methyl}amino)-1-piperidinyl]methyl}-1,2-dihydro-3H,8H-2a,5,8a-triazaacenaphthylene-3,8-dione;

(1R)-1-[(4-{[(5-chloro-6-ethyl-3-pyridinyl)methyl]amino}-1-piperidinyl)methyl]-1,2-dihydro-4H,9H-imidazo[1,2,3-ij]-1,8-naphthyridine-4,9-dione;

(1R)-1-{[4-({[6-(Trifluoromethyl)-3-pyridinyl]methyl}amino)-1-piperidinyl]methyl}-1,2-dihydro-4H,9H-imidazo[1,2,3-ij]-1,8-naphthyridine-4,9-dione hydrochloride;

(1R)-1-{[4-({[5-methyl-6-(trifluoromethyl)-3-pyridinyl]methyl}amino)-1-piperidinyl]methyl}-1,2-dihydro-4H,9H-imidazo[1,2,3-ij]-1,8-naphthyridine-4,9-dione;

(1R)-1-{[4-({[5-bromo-6-(trifluoromethyl)-3-pyridinyl]methyl}amino)-1-piperidinyl]methyl}-1,2-dihydro-4H,9H-imidazo[1,2,3-ij]-1,8-naphthyridine-4,9-dione;

(1R)-1-{[4-({[5-chloro-6-(1-hydroxy-1-methylethyl)-3-pyridinyl]methyl}amino)-1-piperidinyl]methyl}-1,2-dihydro-4H,9H-imidazo[1,2,3-ij]-1,8-naphthyridine-4,9-dione;

(1R)-1-[(4-{[(5-fluoro-6-methyl-3-pyridinyl)methyl]amino}-1-piperidinyl)methyl]-1,2-dihydro-4H,9H-imidazo[1,2,3-ij]-1,8-naphthyridine-4,9-dione;

(1R)-1-{[4-({[3-chloro-4-(hydroxymethyl)phenyl]methyl}amino)-1-piperidinyl]methyl}-1,2-dihydro-4H,9H-imidazo[1,2,3-ij]-1,8-naphthyridine-4,9-dione;

3-chloro-5-{[(1-{[(2R)-3,8-dioxo-1,2-dihydro-3H,8H-2a,5,8a-triazaacenaphthylen-2-yl]methyl}-4-piperidinyl)amino]methyl}-2-pyridinecarbonitrile dihydrochloride;

(2R)-2-[(4-{[(5,6-dichloro-3-pyridinyl)methyl]amino}-1-piperidinyl)methyl]-1,2-dihydro-3H,8H-2a,5,8a-triazaacenaphthylene-3,8-dione;

(2R)-2-{[4-({[5-chloro-6-(hydroxymethyl)-3-pyridinyl]methyl}amino)-1-piperidinyl]methyl}-1,2-dihydro-3H,8H-2a,5,8a-triazaacenaphthylene-3,8-dione;

(2-chloro-4-{[(1-{[(1R)-4,9-dioxo-1,2-dihydro-4H,9H-imidazo[1,2,3-ij]-1,8-naphthyridin-1-yl]methyl}-4-piperidinyl)amino]methyl}phenyl)methyl acetate;

(1R)-1-{[4-({[5-chloro-6-(1-hydroxyethyl)-3-pyridinyl]methyl}amino)-1-piperidinyl]methyl}-1,2-dihydro-4H,9H-imidazo[1,2,3-ij]-1,8-naphthyridine-4,9-dione;

(1R)-1-[(4-{[(6-chloro-5-methyl-3-pyridazinyl)methyl]amino}-1-piperidinyl)methyl]-1,2-dihydro-4H,9H-imidazo[1,2,3-ij]-1,8-naphthyridine-4,9-dione;

(1R)-1-[(4-{[(6-chloro-5-methyl-3-pyridinyl)methyl]amino}-1-piperidinyl)methyl]-1,2-dihydro-4H,9H-imidazo[1,2,3-ij]-1,8-naphthyridine-4,9-dione;
and (2R)-2-{[4-({[5-methyl-6-(trifluoromethyl)-3-pyridinyl]methyl}amino)-1-piperidinyl]methyl}-1,2-dihydro-3H,8H-2a,5,8a-triazaacenaphthylene-3,8-dione hydrochloride.

Certain of the compounds of Formula (I) may exist in the form of optical isomers, e.g. mixtures of isomers in all ratios, e.g. racemic mixtures. The invention includes all such forms, in particular the pure isomeric forms. For example the invention includes enantiomers. The different isomeric forms may be separated or resolved one from the other by conventional methods, or any given isomer may be obtained by conventional synthetic methods or by stereospecific or asymmetric syntheses.

TERMS AND DEFINITIONS

The term "$C_{1-3}$ alkyl" as used herein refers to a straight or branched chain alkyl group having 1 to 3 carbon atoms. Examples of $C_{1-3}$ alkyl groups include methyl, ethyl, n-propyl, iso-propyl.

The term "halo" as used herein refers to fluoro, chloro, bromo and iodo groups. In one aspect, the term "halo" as used herein refers to fluoro, chloro and bromo groups.

The term "$C_{1-3}$ alkoxy" as used herein refers to a straight or branched chain alkoxy group having 1 to 3 carbon atoms. Examples of $C_{1-3}$ alkoxy groups include, methoxy, ethoxy, propoxy and isopropoxy.

The term "compounds of the invention" as used herein means a compound of Formula (I) or a pharmaceutically acceptable salt or N-oxide thereof. The term "a compound of the invention" means any one of the compounds of the invention as defined above.

Furthermore, it will be understood that phrases such as "a compound of Formula (I) or a pharmaceutically acceptable salt or N-oxide thereof" or "compounds of the invention" are intended to encompass the compound of Formula (I), a pharmaceutically acceptable salt or N-oxide of the compound of Formula (I), or any pharmaceutically acceptable combination of these. Thus by way of non-limiting example used here for illustrative purpose, "a compound of Formula (I) or a pharmaceutically acceptable salt or N-oxide thereof" encompasses a pharmaceutically acceptable salt of a compound of Formula (I) which is present as a solvate, or this phrase may include a mixture of a compound of Formula (I) and a salt of a compound of Formula (I).

It will be further appreciated that all crystalline forms, polymorphs and enantiomers of the compounds of the invention, or mixtures thereof, are contemplated to be within the scope of the present invention. Unless otherwise specified (for example when the absolute stereochemistry is shown), for compounds of the invention which possesses stereocentres and which can therefore form enantiomers, the compound contains a 1:1 mixture of enantiomers, i.e. a racemic mixture of enantiomers. These may be separated using conventional techniques such as chiral HPLC.

Some of the compounds of this invention may be crystallised or recrystallised from solvents such as aqueous and organic solvents. In such cases solvates may be formed. This invention includes within its scope stoichiometric solvates including hydrates as well as compounds containing variable amounts of water that may be produced by processes such as lyophilisation.

Since the compounds of Formula (I) are intended for use in pharmaceutical compositions it will readily be understood that in particular embodiments they are provided in substantially pure form, for example at least 60% pure, more suitably at least 75% pure and particularly at least 85%, especially at least 98% pure (% are on a weight for weight basis). Impure preparations of the compounds may be used for preparing the more pure forms used in the pharmaceutical compositions; these less pure preparations of the compounds should contain at least 1%, more suitably at least 5% and more particularly from 10 to 59% of a compound of Formula (I) or pharmaceutically acceptable salt or N-oxide thereof.

Pharmaceutically acceptable salts of the compounds of Formula (I) include the acid addition or quaternary ammonium salts, for example their salts with mineral acids e.g. hydrochloric, hydrobromic, sulphuric nitric or phosphoric acids, or organic acids, e.g. acetic, fumaric, succinic, maleic, citric, benzoic, p-toluenesulphonic, methanesulphonic, naphthalenesulphonic acid or tartaric acids. In one aspect of the invention, the salt of a compound of Formula (I) is the hydrochloride salt. In another aspect, the salt of a compound of Formula (I) is the dihydrochloride salt. Compounds of Formula (I) may also be prepared as the N-oxide. The invention extends to all such salts and N-oxides.

Compound Preparation

In further aspects of the invention there are provided processes for preparing compounds of Formula (I) and pharmaceutically acceptable salts or N-oxides thereof.

In one aspect a suitable process comprises the reaction between an amine compound of Formula (IIA) and a compound of Formula (IIB):

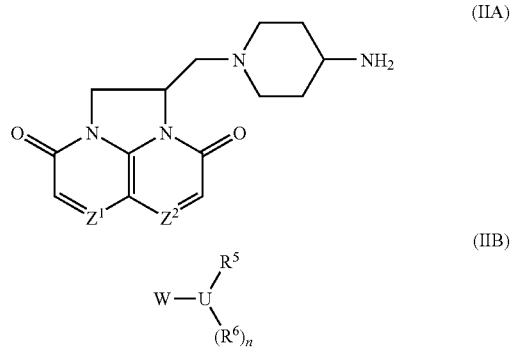

wherein $Z^1$, $Z^2$, U, $R^5$ and $R^6$ and n are as defined in Formula (I), and W is an aldehyde moiety —CH=O, the reaction being a reductive amination reaction, typically in the presence of a reducing agent such as sodium borohydride, or W is a bromomethyl moiety —CH$_2$.Br. Such reactions may be carried out in an organic solvent such as DCM/MeOH at ambient temperature.

See for example Smith, M. B.; March, J. M. *Advanced Organic Chemistry*, Wiley-Interscience.

Compounds of Formula (IIA) in a salt form, e.g. hydrochloride salt form, may be used in this process to form compounds of Formula (I) in a salt form.

Compounds of Formula (IIA) can be made via various preparative schemes.

One such scheme, suitable for compounds in which $Z^1$ is CH and $Z^2$ is N is Scheme (1) below.

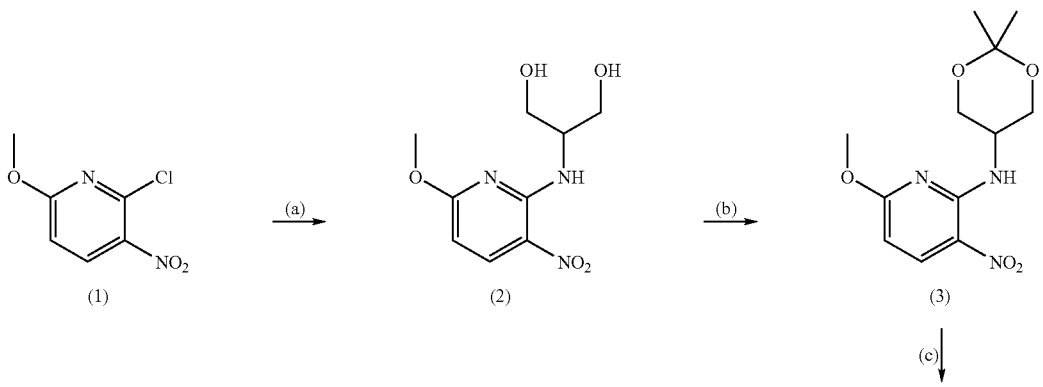

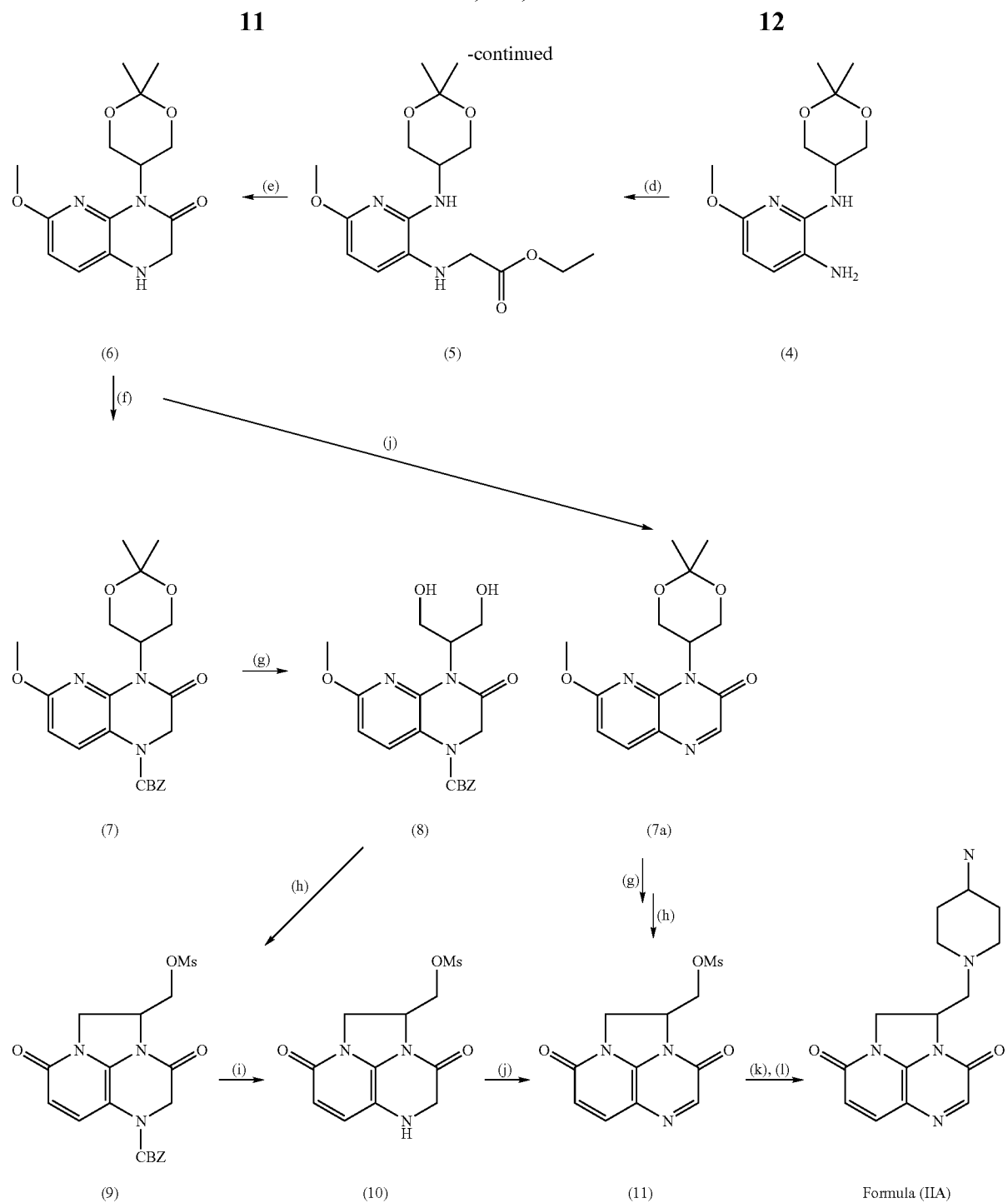

(a) 2-amino-1,3-propanediol (b) 2,2-dimethoxypropane, p-toluenesulfonic acid
(c) hydrogen, palladium/charcoal (d) ethyl bromoacetate, K₂CO₃ (e) sodium hydride
(f) benzyl chloroformate (g) aqueous acid (h) methane sulphonic anhydride
(i) hydrogen, palladium/charcoal (j) MnO₂ (k) 4-(N-tert
butoxycarbonylamino)piperidine, pyridine (l) HCl in 1,4-dioxane.

Reaction of nitropyridine (1) with 2-amino-1,3-propanediol affords diol (2) which is protected as acetal (3). Reduction of the nitro group gives amine (4) which is alkylated to yield ester (5). Cyclisation can be effected with sodium hydride to give (6). This is protected with a carboxybenzyl (CBz) group (7) then cleaved to give the diol (8). Cyclisation with methanesulphonic anhydride affords the mesylate (9), then hydrogenolysis of the CBz group (10) and subsequent oxidation with manganese(11) oxide gives the key dione intermediate mesylate (11). The order of steps may be changed to go via (7a). Reaction of mesylate (11) with 4-(N-tert-butoxycarbonylamino)piperidine and further deprotection by removal of the carbamate moiety affords desired compound of Formula (IIA).

Reaction with an aldehyde of Formula (IIB) may be carried out in the presence of NaBH(OAc)₃ to yield the compound of Formula (I).

Alternatively enantiomerically pure compounds of Formula (IIA) in which $Z^1$ is CH and $Z^2$ is N could be also obtained by preparing the chiral mesylate intermediate in an enantiomerically pure form as depicted in Scheme (1a) below:

lyst gives intermediate (7). Oxidation with manganese (II) oxide and treatment with methanesulfonic anhydride gives (8). This intermediate can be deprotected with TFA to give (9) and reacted with methanesulfonic anhydride or benzenesulfonyl chloride to give (10) as an enantiomerically pure

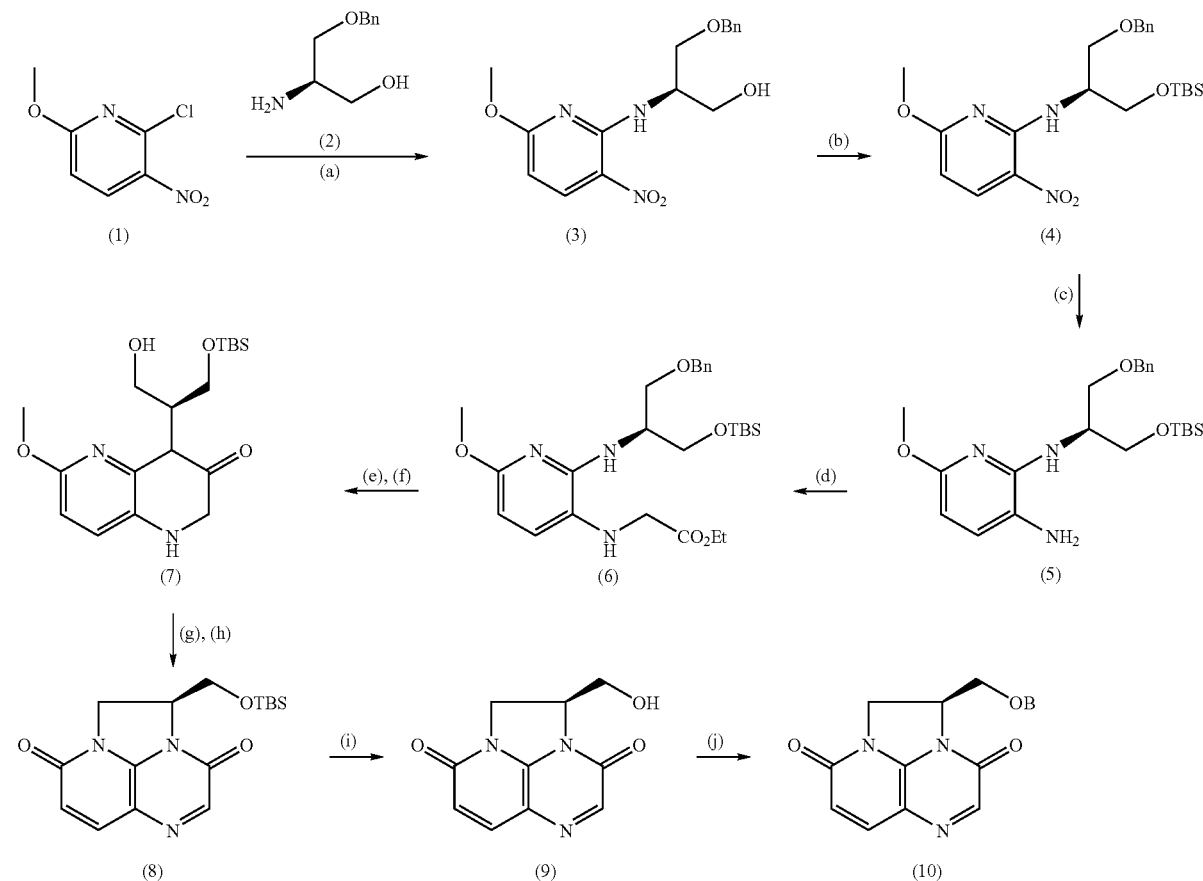

Scheme (1a)

(a) EtOH, reflux, (b) TBS-Cl, (c) Zinc, acetic acid, (d) ethyl bromoacetate, $K_2CO_3$
(e) NaH, (f) hydrogen, palladium/charcoal, (g) $MnO_2$, (h) methanesulfonic anhydride
(i) TFA, (j) methanesulfonic anhydride or benzenesulfonyl chloride.

Reaction of 2-chloro-6-(methyloxy)-3-nitropyridine with chiral amine (2) gives intermediate (3). Protection of (3) with tert-butyl-dimethylsilylchloride gives (4). Reduction of the nitro group gives amine (5), which is alkylated to yield ester (6).

Cyclisation of (6) can be effected with sodium hydride and then treatment with hydrogen over a palladium/charcoal catacompound. The mesylate or benzenesulfonate (10) formed may then be converted to the amine of Formula (IIa) and finally to the target compound of Formula (I) as generally described herein.

Another scheme, suitable for compounds in which $Z^1$ is N and $Z^2$ is CH, is Scheme (2) below.

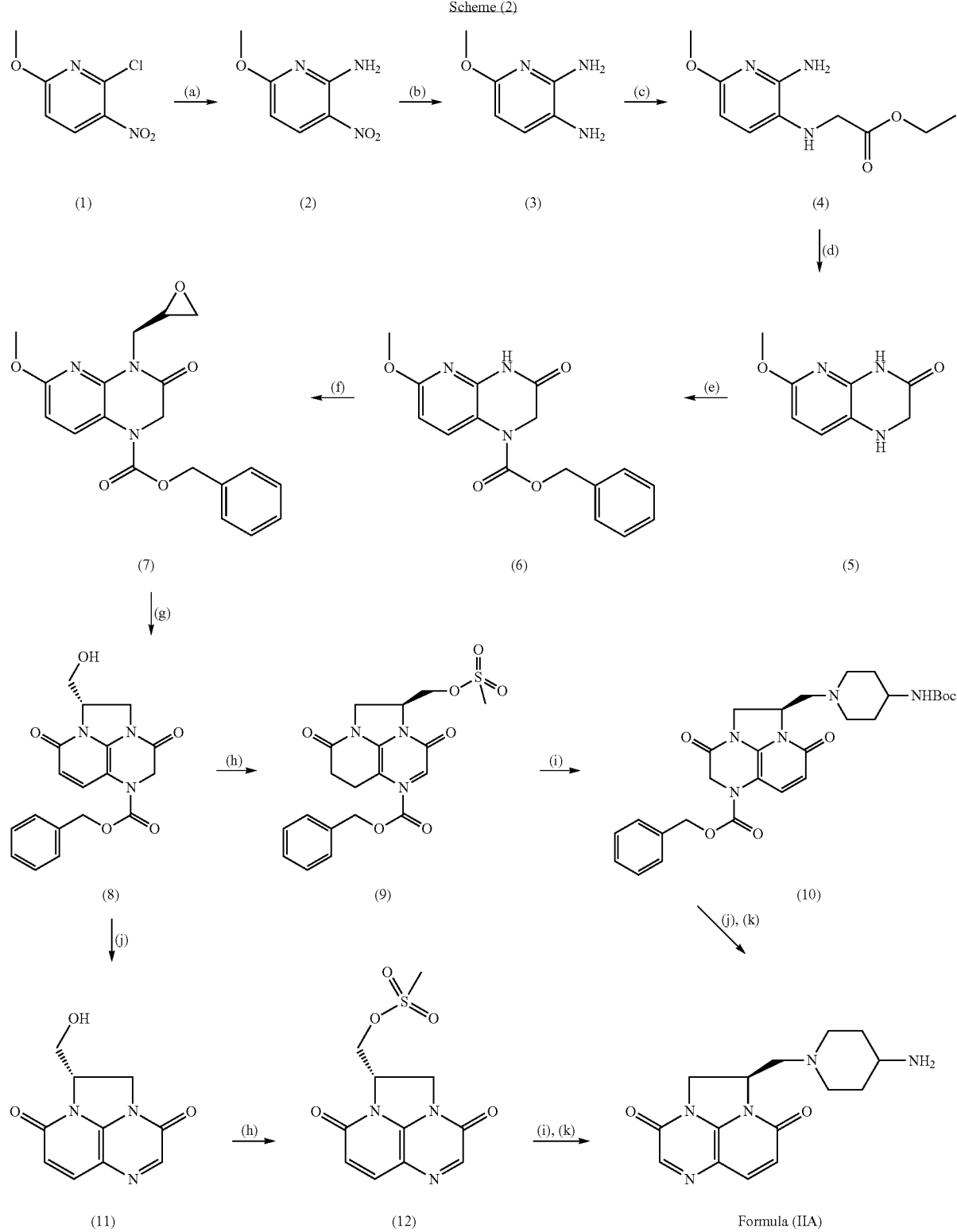
(a) NH$_3$/MeOH (b) hydrogen, palladium/charcoal (c) ethyl bromoacetate, K$_2$CO$_3$
(d) potassium tert-butoxide (e) CBzCl (f) NaH, (S)-glycidyl nosylate (g) DMF, heat
(h) methanesulfonyl chloride (i) 4-(N-tert-butoxycarbonylamino)piperidine, pyridine
(j) hydrogen, palladium/charcoal then MnO$_2$ (k) HCl in 1,4-dioxane.

Reaction of nitropyridine (1) with ammonia affords nitropyridine (2) which is reduced to bis-aniline (3). Alkylation with ethyl bromoacetate followed by cyclisation with potassium tert-butoxide gives (5). This is protected with a carboxybenzyl group to give (6) which can then be reacted with (commercially available) S-glycidyl nosylate ((2S)-2-oxiranylmethyl 3-nitrobenzenesulfonate) to give (7). Cyclisation under thermal conditions gives (8). Mesylation, displacement with 4-(N-tert-butoxycarbonylamino) piperidine, hydrogenolysis of the CBz group (10) and subsequent oxidation with manganese(II) oxide and deprotection by removal of the carbamate moiety gives the target amine of Formula (IIa). Alternatively hydrogenolysis of the CBz group (11) and subsequent oxidation with manganese(II) oxide, followed by mesylation, displacement with 4-(N-tert-butoxycarbonylamino)piperidine and removed of protective group also gives Formula (IIa). This may be converted to the compound of formula (I) as generally described herein.

Another scheme, suitable for compounds in which $Z^1$ and $Z^2$ are CH, is scheme (3) below.

In step (a) trimethylacetamide may be reacted with 2-chloro-6-(methyloxy)pyridine. In step (b) the product of step (a) may be treated with n-butyl lithium and 1,2-dibromoethane. The product from step (b) may be treated in step (c) with n-butyl acrylate. Hydrogenation in the presence of palladium on carbon in step (d) can yield the hydrogenated product. The product of step (d) may be cyclised in step (e) to yield the 3,4-dihydro-1,8-naphthyridin-2(1H)-one by treatment with hydrochloric acid. In step (f) the oxirane may be formed by reaction with sodium hydride then with (2S)-2-oxiranylmethyl 3-nitrobenzenesulfonate. Cyclisation to the imidazonaphthyridine may be done by heating the oxirane, or microwave power. Step (h) to attach the 4-(N-tert-butoxycarbonylamino) piperidine moiety may be performed by formation of the methanesulfonate, then reaction with the corresponding amine. Aromatisation of the ring in step (i) may be done by treatment with DDQ followed by heating. The amine may then be deprotected using acid hydrolysis, step (j) to yield the amine (IIA), which may then be reacted with a compound of Formula IIB e.g. an aldehyde to form the compound of Formula (I).

Scheme (3)

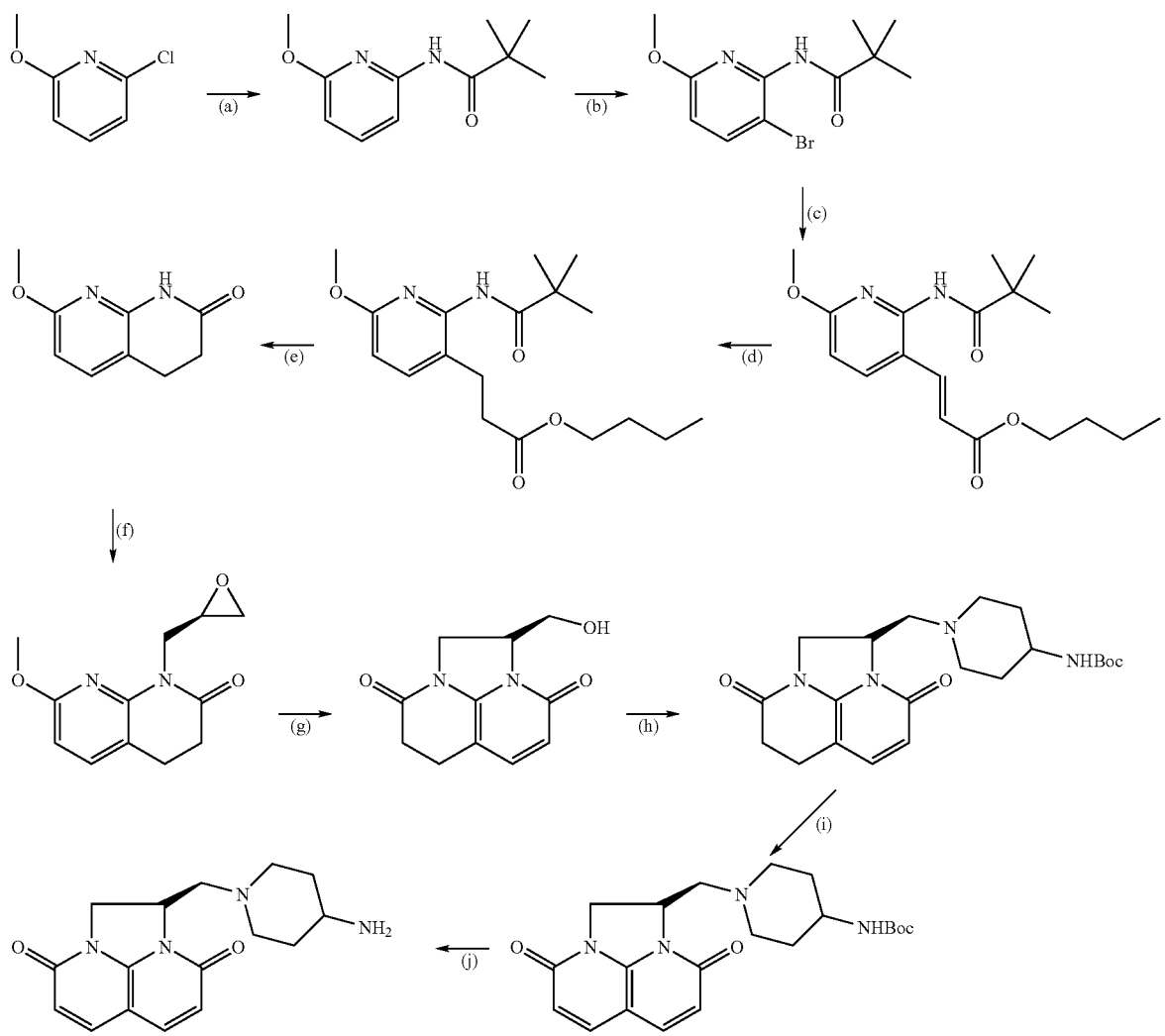

Formula (IIA)

In another aspect a suitable process for making compounds of Formula (I) comprises the reaction between a compound of Formula (IIC) and a compound of Formula (IID):

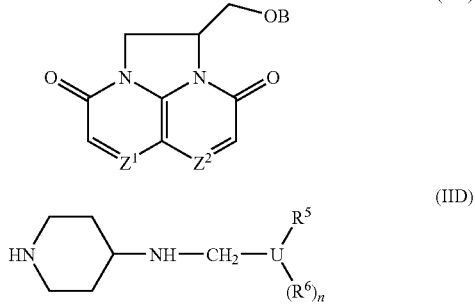

wherein $Z^1$, $Z^2$, U, $R^5$ and $R^6$ and n are as defined in Formula (I) and B is a benzenesulfonyl moiety. Compounds of formula (IID) may for example be prepared from compounds of formula (IIB) as described above by reaction with a compound of formula (IIE):

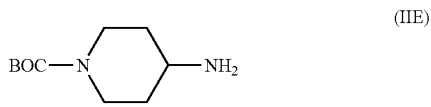

followed by removal of the BOC protecting group from the amino moiety.

An example of such a scheme proceeding via compounds of formula (IIC) and (IID) is Scheme 4 below where a compound of Formula (IIC) may be prepared as described in Scheme (1a).

Scheme (4)

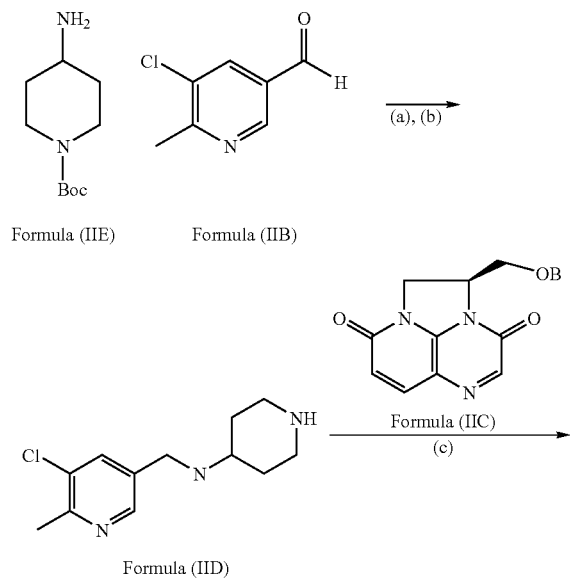

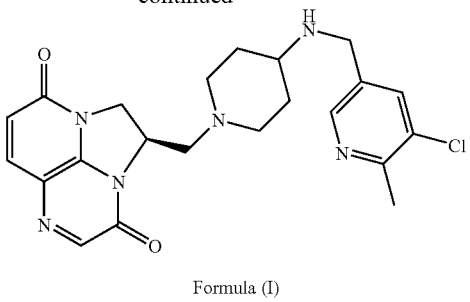

Formula (I)

Salt forms of compounds of Formula (I) and (IA), e.g. hydrochlorides may be formed by treatment of the corresponding free bases with an acid such as hydrochloric acid, or formation of the compounds in the presence of such an acid.

Many appropriate reagents of Formula (IIB) containing the required $R^5$ and optional $R^6$ group are known compounds (see for example the commercial sources listed in Table 1) or may be prepared analogously to known compounds. See for example WO02/08224, WO02/50061, WO02/56882, WO02/96907, WO2003087098, WO2003010138, WO2003064421, WO2003064431, WO2004002992, WO2004002490, WO2004014361, WO2004041210, WO2004096982, WO2002050036, WO2004058144, WO2004087145, WO06002047, WO06014580, WO06010040, WO06017326, WO06012396, WO06137485, WO06017468, WO06020561 and EP0559285.

Using these schemes, alternative reagents to provide alternative substituents such as $R^2$, $R^5$, $R^6$ etc. will be apparent to those skilled in the art.

Further details for the preparation of compounds of Formula (I) are found in the Examples.

Formulations and Administration

The antibacterial and/or antitubercular compounds according to the invention may be formulated for administration in any convenient way for use in human or veterinary medicine, by analogy with other antibacterials or antitubercular compounds.

The pharmaceutical compositions of the invention include those in a form adapted for oral, topical or parenteral use and may be used for the treatment of bacterial infection or infection with *Mycobacterium tuberculosis* in mammals including humans.

The composition may be formulated for administration by any route appropriate to antibacterial and/or antitubercular therapy. The compositions may be in the form of tablets, capsules, powders, granules, lozenges, creams or liquid preparations, such as oral or sterile parenteral solutions or suspensions.

The topical formulations of the present invention may be presented as, for instance, ointments, creams or lotions, eye ointments and eye or ear drops, impregnated dressings and aerosols, and may contain appropriate conventional additives such as preservatives, solvents to assist drug penetration and emollients in ointments and creams.

The formulations may also contain compatible conventional carriers, such as cream or ointment bases and ethanol or oleyl alcohol for lotions. Such carriers may be present as from about 1% up to about 98% of the formulation. More usually they will form up to about 80% of the formulation.

Formulations for oral administration may for example comprise tablets or capsules in unit dose presentation form, and may contain conventional excipients such as binding agents, for example syrup, acacia, gelatin, sorbitol, tragacanth, or polyvinylpyrrolidone; fillers, for example lactose, sugar, maize-starch, calcium phosphate, sorbitol or glycine; tabletting lubricants, for example magnesium stearate, talc, polyethylene glycol or silica; disintegrants, for example potato starch; or acceptable wetting agents such as sodium lauryl sulphate. The tablets may be coated according to methods well known in normal pharmaceutical practice.

Formulations for oral administration may also be in liquid form, for example in the form of aqueous or oily suspensions, solutions, emulsions, syrups or elixirs, or may be presented as a dry product for reconstitution with water or other suitable vehicle before use. Such liquid preparations may contain conventional additives, such as suspending agents, for example sorbitol, methyl cellulose, glucose syrup, gelatin, hydroxyethyl cellulose, carboxymethyl cellulose, aluminium stearate gel or hydrogenated edible fats, emulsifying agents, for example lecithin, sorbitan monooleate, or acacia; non-aqueous vehicles (which may include edible oils), for example almond oil, oily esters such as glycerine, propylene glycol, or ethyl alcohol; preservatives, for example methyl or propyl p-hydroxybenzoate or sorbic acid, and, if desired, conventional flavouring or colouring agents.

Suppositories will contain conventional suppository bases, e.g. cocoa-butter or other glyceride.

For parenteral administration, fluid unit dosage forms are prepared utilizing the compound and a sterile vehicle, water being preferred. The compound, depending on the vehicle and concentration used, can be either suspended or dissolved in the vehicle. In preparing solutions the compound can be dissolved in water for injection and filter sterilised before filling into a suitable vial or ampoule and sealing.

Advantageously, agents such as a local anaesthetic, preservative and buffering agents can be dissolved in the vehicle. To enhance the stability, the composition can be frozen after filling into the vial and the water removed under vacuum. The dry lyophilized powder is then sealed in the vial and an accompanying vial of water for injection may be supplied to reconstitute the liquid prior to use. Parenteral suspensions are prepared in substantially the same manner except that the compound is suspended in the vehicle instead of being dissolved and sterilization cannot be accomplished by filtration. The compound can be sterilised by exposure to ethylene oxide before suspending in the sterile vehicle. Advantageously, a surfactant or wetting agent is included in the composition to facilitate uniform distribution of the compound.

Depending on the route of administration the compositions may contain from 0.1% by weight, preferably from 10-60% by weight, of a compound of the invention. Where the compositions comprise dosage units, each unit will preferably contain from 50-1000 mg of the active ingredient. The dosage as employed for adult human treatment will preferably range from 100 to 3000 mg per day, for instance 1500 mg per day depending on the route and frequency of administration. Suitably the dosage is from 5 to 30 mg/kg per day.

The compound of Formula (I), or a pharmaceutically acceptable pharmaceutically acceptable salt or N-oxide thereof, may be the sole therapeutic agent in the compositions of the invention, or it may be present in the formulation in combination with one or more additional therapeutic agents. The invention thus provides, in a further aspect, a combination comprising a compound of Formula (I), or a pharmaceutically acceptable salt or N-oxide thereof together with one or more additional therapeutic agents.

The one or more additional therapeutic agent is, for example, an agent useful for the treatment of tuberculosis in a mammal. Examples of such therapeutic agents include isoniazid, ethambutol, rifampin, pirazinamide, streptomycin, capreomycin, ciprofloxacin and clofazimine.

When a compound of Formula (I), or a pharmaceutically acceptable pharmaceutically acceptable salt or N-oxide thereof is used in combination with one or more additional therapeutic agents, the dose of the compound or agent may differ from that when the compound or agent is used alone. Appropriate doses will be readily appreciated by those skilled in the art. It will be appreciated that the amount of a compound of the invention and the one or more additional therapeutic agents required for use in treatment will vary with the nature of the condition being treated and the age and the condition of the patient and will be ultimately at the discretion of the attendant physician or veterinarian.

The combinations may conveniently be presented for use in the form of a pharmaceutical formulation. In a further aspect of the present invention there is provided a pharmaceutical combination comprising a compound of Formula (I), or a pharmaceutically acceptable salt or N-oxide thereof, together with one or more additional therapeutic agents, and one or more pharmaceutically acceptable carriers, excipients or diluents. The individual components of such combinations may be administered either sequentially or simultaneously in separate or combined pharmaceutical formulations by any convenient route.

When administration is sequential, either the compound of the present invention or one or more additional therapeutic agent may be administered first. When administration is simultaneous, the combination may be administered either in the same or different pharmaceutical composition. When combined in the same formulation it will be appreciated that the compound and agents must be stable and compatible with each other and the other components of the formulation. When formulated separately they may be provided in any convenient formulation, conveniently in such manner as are known for such compounds in the art.

The compound of Formula (I) may be the sole therapeutic agent in the compositions of the invention or a combination with one or more other antibacterial and/or antitubercular compound. If the other antibacterial is a β-lactam then a β-lactamase inhibitor may also be employed.

Compounds of Formula (I) may also be used in the treatment of bacterial infections caused by a wide range of organisms including both Gram-negative and Gram-positive organisms. Some compounds of Formula (I) may be active against more than one organism. This may be determined by the methods described herein.

All publications, including but not limited to patents and patent applications, cited in this specification are herein incorporated by reference as if each individual publication were specifically and individually indicated to be incorporated by reference herein as though fully set forth.

The following Examples illustrate the preparation of certain compounds of Formula (I) and the activity of certain compounds of Formula (I) against various bacterial organisms and organisms which are known to cause tuberculosis.
Examples and Experimental
Abbreviations used herein:

| | |
|---|---|
| AcOH | acetic acid |
| Ac$_2$O | acetic anhydride |
| Bn | benzyl |
| BOC | N-tert-butoxycarbonyl |
| BOC anhydride | di-tert-butyl dicarbonate |
| CH$_3$CN | acetonitrile |

| | |
|---|---|
| CBz | carbobenzyl |
| Celite ® | a filter aid composed of acid-washed diatomaceous silica, (a trademark of Manville Corp., Denver, Colorado) |
| CF₃TMS | (trifluoromethyl)trimethylsilane |
| DME | dimethoxyethane |
| DCM | dichloromethane |
| DDQ | 2,3-dichloro-5,6-dicyano-1,4-benzoquinone (an aromatization reagent) |
| DIBAL-H | diisobutyl aluminium hydride |
| DMF | dimethylformamide |
| DMSO-d₆ | deuterated dimethylsulfoxide |
| DMSO | dimethylsulfoxide |
| ES MS | electrospray mass spectrometry |
| EtOAc | EtOAc |
| EtOH | ethanol |
| Et₃N | triethylamine |
| h | hours |
| HPLC | high performance liquid chromatography |
| LCMS | liquid chromatography mass spectroscopy |
| MeOH | methanol |
| MP-carbonate | macroporous triethylammonium methylpolystyrene carbonate (Argonaut Technologies) |
| Ms | methanesufonyl (Mesyl) |
| NaBH(OAc)₃ | sodium triacetoxyborohydride |
| NMP | N-methyl pyrrolidone (solvent) |
| NMR | nuclear magnetic resonance spectroscopy |
| AcO | acetoxy |
| Pd/C | palladium on carbon catalyst |
| Pd₂(dba)₃ | tris-(dibenxylideneacetone) dipalladium |
| rt | room temperature |
| SCX Cartridge | is an ion exchange column containing strong cation exchange resin (benzene sulfonic acid) supplied by Varian, USA. |
| TBS-Cl | tert-Butyldimethylsilyl chloride |
| TBME | methyl tert-butyl ether |
| TFA | trifluoroacetic acid |
| THF | tetrahydrofuran |
| uv | ultraviolet |

Proton nuclear magnetic resonance (¹H NMR) spectra were recorded, and chemical shifts are reported in parts per million (δ) downfield from the internal standard tetramethylsilane (TMS). Abbreviations for NMR data are as follows: s=singlet, d=doublet, t=triplet, q=quartet, m=multiplet, dd=doublet of doublets, dt=doublet of triplets, app=apparent, br=broad. Mass spectra were obtained using electrospray (ES) ionization techniques. All temperatures are reported in degrees centigrade.

As will be understood by the skilled chemist, references to preparations carried out in a similar manner to, or by the general method of, other preparations, may encompass variations in routine parameters such as time, temperature, workup conditions, minor changes in reagent amounts etc.

Reactions involving metal hydrides including lithium hydride, lithium aluminium hydride, di-isobutylaluminium hydride, sodium hydride, sodium borohydride and sodium triacetoxyborohydride are carried out under argon.

In the experimental Examples below, preparation of the compounds tabulated as Examples 1, 2, 9, 11, 12, 17, 51, 59, 60, 71 and 75 are presented as representative of compounds of this invention and of the various preparative schemes referred to herein. Further compounds of the invention prepared by analogous routes are listed in Table 1.

Example 1

Compound: Synthesis of (1R)-1-[(4-{[(5-chloro-6-methyl-3-pyridinyl)methyl]amino}-1-piperidinyl)methyl]-1,2-dihydro-4H,9H-imidazo[1,2,3-ij]-1,8-naphthyridine-4,9-dione hydrochloride, using Preparative Scheme (3)

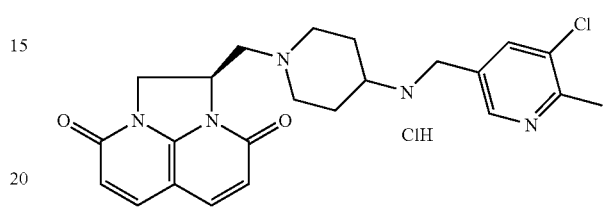

(a) 2,2-Dimethyl-N-[6-(methyloxy)-2-pyridinyl]propanamide

A suspension of trimethylacetamide (18.08 g, 178.744 mmol), Cs₂CO₃ (68.823 g, 211.242 mmol), Pd₂(dba)₃ (1.488 g, 1.625 mmol) and Xantphos (4,5-bis(diphenylphosphino)-9,9-dimethylxanthene) (1.880 g, 3.249 mmol) in dry, degassed 1,4-dioxane (800 ml) under argon was sonicated for 0.25 h and then treated with 2-chloro-6-(methyloxy)pyridine (19.32 ml, 162.494 mmol). The mixture was then heated at reflux for 24 h. The mixture was evaporated, treated with water (1 L) and extracted 3×DCM (1 L and then 2×500 ml). The organics were dried (MgSO₄), evaporated and chromatographed (50-100% DCM/40-60 Petroleum ether then 0-5% MeOH/DCM) to give title compound as a yellow solid (25.191 g, 121.111 mmol, 75%). Impure fractions were recolumned (eluting as above) to give more product (4.990 g, 23.990 mmol, 15%). Total yield of 90%.
[ES MS] m/z 209 (MH⁺, 100%).

(b) N-[3-Bromo-6-(methyloxy)-2-pyridinyl]-2,2-dimethylpropanamide

A solution of 2,2-dimethyl-N-[6-(methyloxy)-2-pyridinyl]propanamide (55.011 g, 264.467 mmol) in THF (450 ml) in a three necked 1 L flask with an internal thermometer under argon was cooled to −78° C. and treated with n-butyl lithium (232 ml, 581.847 mmol) over 15 minutes and then allowed to warm to 0° C. and stirred at 0° C. for 7 h. The mixture was then recooled to −78° C. and treated with 1,2-dibromoethane (27.3 ml, 317 mmol) over 10 minutes and then the solution was allowed warm to room temperature and stirred at room temperature for 30 minutes by which time all the solid which had formed dissolved again. Gas was evolved at this stage so a gas bubbler was placed on one of the flasks necks. Water (100 ml) was then carefully added over 10 minutes. Further water (500 ml) was then added and the mixture was extracted with Et₂O (3×500 ml). The combined organic solvents were then dried (MgSO₄), filtered, evaporated to give the crude product. This was then dissolved in warm EtOAc (100 ml) and allowed to stand in the freezer overnight. The resultant solid which crystallised out was filtered off, washed with ice-cooled Et₂O (20 ml) and dried in vacuo to give product as a white solid (45.660 g, 159.011 mmol, 60%). The filtrate was evaporated and the residue was chromatographed (0-25% EtOAc/40-60 petroleum ether) to give recovered starting material (7.264 g, 34.9 mmol), and product as a white solid (8.038 g, 27.99 2 mmol, 10%). The product from recrystallisation and chromatography were identical by NMR and LC-MS and so were combined.

[ES MS] m/z 287/289 (MH+, 100%).

(c) Butyl (2E)-3-[2-[(2,2-dimethylpropanoyl)amino]-6-(methyloxy)-3-pyridinyl]-2-propenoate A mixture of N-[3-bromo-6-(methyloxy)-2-pyridinyl]-2,2-dimethylpropanamide (78.738 g, 274 mmol), bis(tri-t-butylphosphine)palladium(0) (1 g, 1.957 mmol) and tris(dibenzylideneacetone)dipalladium(0) (0.892 g, 0.974 mmol) in dry, degassed 1,4-dioxane (600 ml) was treated with n-butyl acrylate (47.1 ml, 329 mmol) and dicyclohexylmethylamine (64.5 ml, 302 mmol). The reaction mixture was then heated at 80° C. for 4 h and then at 120° C. for 3 h. The reaction was then evaporated and water (1000 ml) was added and the mixture was extracted with Et$_2$O (3×500 ml). The combined organic solvents were then dried (MgSO$_4$), filtered, evaporated to give the crude product. This was then dissolved in DCM (300 ml) and chromatographed (10-30% EtOAc:40-60 petroleum ether) and then dried in vacuo to give product as a white solid (87.412 g, 95%).

[ES MS] m/z 335 (MH+, 100%).

(d) Butyl 3-[2-[(2,2-dimethylpropanoyl)amino]-6-(methyloxy)-3-pyridinyl]propanoate A solution of butyl (2E)-3-[2-[(2,2-dimethylpropanoyl)amino]-6-(methyloxy)-3-pyridinyl]-2-propenoate (43.706 g, 131 mmol) in ethanol (450 ml) under argon at rt was treated with palladium on carbon (10% paste) (5.0 g, 47.0 mmol) and then stirred at rt under 1 atmosphere of hydrogen for 90 h. The reaction mixture was then filtered through a thin pad of Kieselguhr, washing the product through with further ethanol (200 ml). The solvent was then evaporated to give product as a yellow solid (43.549 g, 99%).

[ES MS] m/z 337 (MH+, 100%).

(e) 7-(Methyloxy)-3,4-dihydro-1,8-naphthyridin-2(1H)-one

A mixture of butyl 3-[2-[(2,2-dimethylpropanoyl)amino]-6-(methyloxy)-3-pyridinyl]propanoate (86.01 g, 256 mmol) in hydrochloric acid (500 ml, 3000 mmol) (6M aqueous), was heated at 80° C. for 6 h. Reaction was cooled, treated with water (500 ml), transferred to a 5 L conical flask and carefully neutralised with solid K$_2$CO$_3$ (requires around 250 g) (much effervescence was observed). The mixture was then extracted with 20% MeOH/DCM (3×500 ml). The combined organic solvents were then dried (MgSO$_4$), filtered, evaporated to give the crude product as a yellow solid (35.84 g, 79%).

[ES MS] m/z 179 (MH+, 100%).

(f) 7-(Methyloxy)-1-[(2R)-2-oxiranylmethyl]-3,4-dihydro-1,8-naphthyridin-2(1H)-one A solution of 7-(methyloxy)-3,4-dihydro-1,8-naphthyridin-2(1H)-one (4.974 g, 27.9 mmol) in DMF (100 ml) at 0° C. under argon was treated with sodium hydride (60%, 1.340 g, 33.5 mmol) and allowed to stir at 0° C. for 20 min. The reaction mixture was then treated with (2S)-2-oxiranylmethyl 3-nitrobenzenesulfonate (7.60 g, 29.3 mmol) and then then allowed warm slowly to rt and stirred at rt for 1 h. Water (5 ml) was then added. Reaction was evaporated, saturated aqueous NaHCO$_3$ (500 ml) was then added and the mixture was extracted with DCM (3×500 ml). The combined organic solvents were then dried (MgSO$_4$), filtered, evaporated to give the crude product.

[ES MS] m/z 235 (MH+, 100%).

(g) (1S)-1-(Hydroxymethyl)-1,2,5,6-tetrahydro-4H,9H-imidazo[1,2,3-ij]-1,8-naphthyridine-4,9-dione A solution of 7-(methyloxy)-1-[(2R)-2-oxiranylmethyl]-3,4-dihydro-1,8-naphthyridin-2(1H)-one (1.167 g, 4.98 mmol) in DMF (20 ml) under argon was heated to 120° C. for 6 h. Reaction was then evaporated and chromatographed (0-20% MeOH/DCM) to give product as an orange solid (339 mg, 31%).

[ES MS] m/z 221 (MH+, 100%).

Alternatively the reaction can be heated with microwave power at 160° C. for 40 mins.

(h) 1,1-Dimethylethyl (1-{[(2R)-4,9-dioxo-1,2,8,9-tetrahydro-4H,7H-imidazo[1,2,3-ij]-1,8-naphthyridin-2-yl]methyl}-4-piperidinyl)carbamate A solution of (1S)-1-(hydroxymethyl)-1,2,5,6-tetrahydro-4H,9H-imidazo[1,2,3-ij]-1,8-naphthyridine-4,9-dione (1.909 g, 8.67 mmol) in DCM (100 ml) at 0° C. under argon was treated with Et$_3$N (1.450 ml, 10.40 mmol) and then methanesulfonyl chloride (0.743 ml, 9.54 mmol) and then allowed to warm to rt and stirred at rt for 1 h. The reaction mixture was then treated with saturated aqueous NaHCO$_3$ (100 ml) and the mixture was extracted with DCM (2×100 ml). The combined organic solvents were then dried (MgSO$_4$), filtered, evaporated to give the crude intermediate [(2S)-4,9-dioxo-1,2,8,9-tetrahydro-4H,7H-imidazo[1,2,3-ij]-1,8-naphthyridin-2-yl]methyl methanesulfonate. This was dissolved in dry CH$_3$CN (100 ml) and then treated with pyridine (1.402 ml, 17.34 mmol) and 1,1-dimethylethyl 4-piperidinylcarbamate (3.47 g, 17.34 mmol) and heated at 70° C. for 20 h. After 20 h more 1,1-dimethylethyl 4-piperidinylcarbamate (3.47 g, 17.34 mmol) and pyridine (1.402 ml, 17.34 mmol) were added and the temperature was increased to reflux (heating block 95° C.) and reaction was stirred at this temperature for a further 4 h. The reaction mixture was then evaporated, treated with saturated aqueous NaHCO$_3$ (200 ml) was then added and the mixture was extracted with DCM (3×200 ml). The combined organic solvents were then dried (MgSO$_4$), filtered, evaporated to give the crude product as a brown solid.

[ES MS] m/z 403 (MH+, 100%).

(i) 1,1-Dimethylethyl (1-{[(1R)-4,9-dioxo-1,2-dihydro-4H,9H-imidazo[1,2,3-ij]-1,8-naphthyridin-1-yl]methyl}-4-piperidinyl)carbamate A solution of 1,1-dimethylethyl (1-{[(2R)-4,9-dioxo-1,2,8,9-tetrahydro-4H,7H-imidazo[1,2,3-ij]-1,8-naphthyridin-2-yl]methyl}-4-piperidinyl)carbamate (5.710 g, 14.19 mmol) in 1,4-dioxane (50 ml) at rt was treated with DDQ (4.83 g, 21.28 mmol) and then heated at 120° C. for 1 h. The reaction was then cooled to rt. The reaction mixture was treated with saturated aqueous K$_2$CO$_3$ (5%, 1000 ml) and extracted with DCM (3×500 ml). The combined organic solvents were then dried (MgSO$_4$), filtered, evaporated to give the crude product as a brown solid. The reaction was repeated using a further portion of carbamate (2.889 g, 7.18 mmol) in 1,4-dioxane (50 ml) with DDQ (2.444 g, 10.77 mmol). The reaction was performed and worked up as above and the combined residues were chromatographed (0-100% EtOAc: 40-60 Petroleum ether then 0-20% MeOH:EtOAc) to give the product as a brown solid (1.532 g, 18%).

[ES MS] m/z 401 (MH+, 100%).

(j) (1R)-1-[(4-Amino-1-piperidinyl)methyl]-1,2-dihydro-4H,9H-imidazo[1,2,3-ij]-1,8-naphthyridine-4,9-dione A solution of 1,1-dimethylethyl (1-{[(1R)-4,9-dioxo-1,2-dihydro-4H,9H-imidazo[1,2,3-ij]-1,8-naphthyridin-1-yl]methyl}-4-piperidinyl)carbamate (1.532 g, 3.83 mmol) in chloroform (20 ml) under argon at rt was treated with 4M HCl in 1,4-dioxane (10 ml, 40.0 mmol) and stirred at rt for 0.25 h. MeOH (20 ml) was then added and reaction was stirred for a further 0.25 h. The reaction was then evaporated and triturated with Et$_2$O (20 ml). The solid was then dried in vacuo to give the impure product as a brown solid (1.443 g, 101%).

[ES MS] m/z 301 (MH+, 100%).

1-[(4-Amino-1-piperidinyl)methyl]-1,2-dihydro-4H,9H-imidazo[1,2,3-ij]-1,8-naphthyridine-4,9-dione dihydrochloride made by this general method (Example 5(a)-(j)) was analyzed via chiral HPLC (Chiralpak AS-H (5 microns)) and found to be a single enantiomer, presumed to be R.

The crude dihydrochloride was dissolved in MeOH and water (1 ml) and applied to an SCX column (20 g) (preconditioned with 2 column volumes of MeOH). The column was then eluted, under gravity, using (i) MeOH, (ii) 0.5M ammonia in MeOH. Appropriate fractions were combined and evaporated under reduced pressure to give 1.0 g (88%) of the title compound as a beige solid.

(k) Title compound: (1R)-1-[(4-{[(5-Chloro-6-methyl-3-pyridinyl)methyl]amino}-1-piperidinyl)methyl]-1,2-dihydro-4H,9H-imidazo[1,23-ij]-1,8-naphthyridine-4,9-dione hydrochloride A solution of (1R)-1-[(4-amino-1-piperidinyl)methyl]-1,2-dihydro-4H,9H-imidazo[1,2,3-ij]-1,8-naphthyridine-4,9-dione (119 mg, 0.396 mmol) and 5-chloro-6-methyl-3-pyridinecarbaldehyde (for a synthesis see WO2006/137485 A1 Example 256) (61.6 mg, 0.396 mmol) in a mixture of DCM (1.5 ml) and MeOH (1.5 ml) was stirred at room temperature for 2 h. NaBH(OAc)$_3$ (252 mg, 1.189 mmol) was then added and the mixture stirred at room temperature. The reaction was monitored by LCMS and when full conversion was observed, it was quenched with 10% NaHCO$_3$ and extracted with DCM. The organic layer was dried (MgSO$_4$), filtered, and concentrated.

Purification by flash chromatography using Flashmaster II, a 5 g silica gel cartridge, and mixtures of DCM and MeOH as eluent afforded 88 mg (0.2 mmol, 51%) of the expected product as the free base.

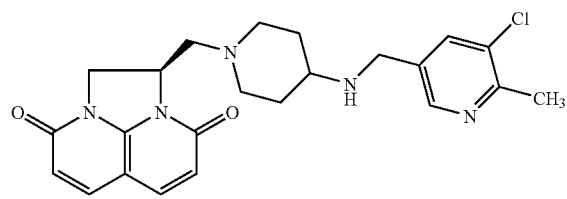

$^1$H-NMR (δ, ppm, CDCl$_3$): 8.29 (d, 1H), 7.66 (d, 1H), 7.48 (dd, 2H), 6.27 (dd, 2H), 5.00-4.96 (m, 1H), 4.56 (dd, 1H), 4.37 (dd, 1H), 3.76 (s, 2H), 3.10 (dd, 1H), 2.96-2.91 (m, 1H), 2.67 (dd, 2H), 2.59 (s, 3H), 2.54-2.48 (m, 1H), 2.30-2.17 (m, 2H), 1.90-1.81 (m, 2H), 1.47-1.31 (m, 2H). [ES MS] m/z 440 (MH+).

This free base was dissolved in MeOH (9 ml). HCl (4M solution in 1,4-dioxane, 0.050 ml, 0.2 mmol) was added dropwise. After stirring at room temperature for 20 min, the solvent was evaporated. MeOH and hexane were used to help removal of dioxane. (1R)-1-[(4-{[(5-chloro-6-methyl-3-pyridinyl)methyl]amino}-1-piperidinyl)methyl]-1,2-dihydro-4H,9H-imidazo[1,2,3-ij]-1,8-naphthyridine-4,9-dione hydrochloride (92.5 mg, 0.194 mmol, 49.0%) was obtained as an off-white solid.

$^1$H-NMR (δ, ppm, CDCl$_3$+CD$_3$OD): 8.33 (d, 1H), 8.05 (d, 1H), 7.53 (d, 1H), 7.52 (d, 1H), 6.28 (d, 1H), 6.24 (d, 1H), 5.05-4.93 (m, 1H), 4.48 (dd, 1H), 4.35 (dd, 1H), 3.99 (s, 2H), 3.07 (dd, 1H), 3.03-2.78 (m, 2H), 2.77-2.62 (m, 2H), 2.58 (s, 3H), 2.37-2.17 (m, 2H), 2.12-1.97 (m, 2H), 1.70-1.46 (m, 2H). [ES MS] m/z 440 (MH+).

Example 1A

Synthesis of Example 1 Compound (1R)-1-[(4-{[(5-chloro-6-methyl-3-pyridinyl)methyl]amino}-1-piperidinyl)methyl]-1,2-dihydro-4H,9H-imidazo[1,2,3-ij]-1,8-naphthyridine-4,9-dione hydrochloride, proceeding via a salt form of a compound of Formula (IIA)

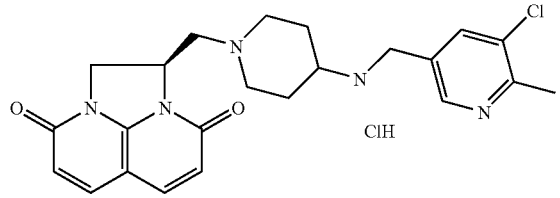

(i) (1R)-1-[(4-amino-1-piperidinyl)methyl]-1,2-dihydro-4H,9H-imidazo[1,2,3-ij]-1,8-naphthyridine-4,9-dione dihydrochloride A solution of 1,1-dimethylethyl (1-{[(1R)-4,9-dioxo-1,2-dihydro-4H,9H-imidazo[1,2,3-ij]-1,8-naphthyridin-1-yl]methyl}-4-piperidinyl)carbamate (see Example 1 (i) above) (4.282 g, 10.69 mmol) in CHCl$_3$ (20 ml) under Ar at room temperature was treated with HCl (4M solution in 1,4-dioxane, 20 ml, 80 mmol) and stirred at rt for 15 min, MeOH (20 ml) was then added. After stirred for 15 min, the reaction was evaporated and triturated with Et$_2$O (20 ml). The obtained solid was dried in vacuo to give (1R)-1-[(4-amino-1-piperidinyl)methyl]-1,2-dihydro-4H,9H-imidazo[1,2,3-ij]-1,8-naphthyridine-4,9-dione dihydrochloride (4.55 g, 12.21 mmol, 100%) as a yellow powder.

[ES MS] m/z 301 (MH+).

(ii) Title compound: (1R)-1-[(4-{[(5-Chloro-6-methyl-3-pyridinyl)methyl]amino}-1-piperidinyl)methyl]-1,2-dihydro-4H,9H-imidazo[1,2,3-ij]-1,8-naphthyridine-4,9-dione hydrochloride A solution of (1R)-1-[(4-amino-1-piperidinyl)methyl]-1,2-dihydro-4H,9H-imidazo[1,2,3-ij]-1,8-naphthyridine-4,9-dione dihydrochloride (63.3 mg, 0.170 mmol) and Et$_3$N (0.022 ml, 0.154 mmol) in CHCl₃ (3 ml) was stirred at room temperature for 15 min then 5-chloro-6-methyl-3-pyridinecarbaldehyde (for a synthesis see WO20006/137485 A1 Example 256) (24 mg, 0.154 mmol) was added. The resulting reaction mixture was stirred at room temperature for 1 h then NaBH(OAc)₃ (98 mg, 0.463 mmol) was added and the mixture was stirred at room temperature overnight. The reaction was monitored by LCMS and when full conversion was observed, it was quenched with 10% NaHCO₃ and extracted with DCM several times. The organic layer was dried (MgSO₄), filtered, and concentrated. Purification by flash chromatography using a 5 g silica gel cartridge, and mixtures of DCM and MeOH as eluent afforded 9 mg (13%) of the expected product as the free base. It was dissolved in MeOH (2 ml). HCl (1M solution in Et₂O, 0.02 ml, 0.02 mmol) was added dropwise. After stirring at room temperature for 20 min, the solvent was evaporated. (1R)-1-[(4-{[(5-Chloro-6-methyl-3-pyridinyl)methyl]amino}-1-piperidinyl)methyl]-1,2-dihydro-4H,9H-imidazo[1,2,3-ij]-1,8-naphthyridine-4,9-dione hydrochloride (92.5 mg, 0.194 mmol, 49%) was obtained as a yellow powder.

¹H-NMR (δ, ppm, CDCl₃+CD₃OD): 8.33 (d, 1H), 8.05 (d, 1H), 7.53 (d, 1H), 7.52 (d, 1H), 6.28 (d, 1H), 6.24 (d, 1H), 5.05-4.93 (m, 1H), 4.48 (dd, 1H), 4.35 (dd, 1H), 3.99 (s, 2H), 3.07 (dd, 1H), 3.03-2.78 (m, 2H), 2.77-2.62 (m, 2H), 2.58 (s, 3H), 2.37-2.17 (m, 2H), 2.12-1.97 (m, 2H), 1.70-1.46 (m, 2H). [ES MS] m/z 440 (MH⁺).

Example 2

Compound: Synthesis of (2R)-2-[(4-{[(5-chloro-6-methyl-3-pyridinyl)methyl]amino}-1-piperidinyl)methyl]-1,2-dihydro-3H,8H-2a,5,8a-triazaacenaphthylene-3,8-dione hydrochloride, using Preparative Scheme (1)

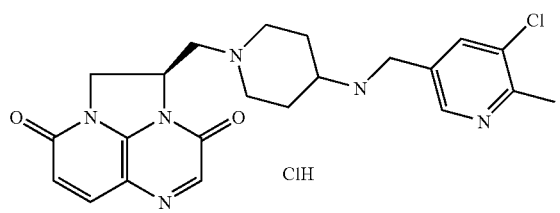

(a) 2-{[6-(Methyloxy)-3-nitro-2-pyridinyl]amino}-1,3-propanediol

6-Methoxy-2-chloro-3-nitropyridine (36.94 g, 195.9 mmol) and 2-aminopropane-1,3-diol (35.65 g, 391.3 mmol) were stirred in ethanol (500 ml) at reflux under argon for 3 h. The mixture was allowed to cool to room temperature and left overnight. The solvent was partially removed under reduced pressure (to ca. 150 ml) and the resulting bright yellow slurry was poured into ice-water (1.5 L) with vigorous stirring. The mixture was stirred for 1 h then filtered with suction while cold. The solid was washed with ice-cold water (200 ml) and air-dried to give the title compound as a bright yellow solid (45.03 g, 94%). LCMS showed desired product (93%) plus 7% starting material. The product was used without further purification.

[ES MS] m/z 244 (MH⁺).

(b) N-(2,2-Dimethyl-1,3-dioxan-5-yl)-6-(methyloxy)-3-nitro-2-pyridinamine

2-{[6-(Methyloxy)-3-nitro-2-pyridinyl]amino}-1,3-propanediol (53.93 g, 228.7 mmol) was stirred in 2,2-dimethoxypropane (900 ml) under argon and p-toluenesulphonic acid monohydrate (1.00 g) was added. The mixture was stirred at room temperature overnight to give a clear yellow solution. This was with diluted with DCM (1 L) and the resulting solution was treated with saturated aqueous NaHCO₃ (20 ml) and solid NaHCO₃ (20 g) with vigorous stirring (effervescence). The mixture was vigorously stirred for 20 minutes, then the remaining water was absorbed by addition of anhydrous Na₂SO₄. The mixture was filtered with suction and the solids were washed with DCM (500 ml). The combined filtrate plus washings were evaporated under reduced pressure to give a yellow solid which was stirred with petroleum ether (40-60°) over the weekend. The solid was isolated by filtration with suction, washed with petroleum ether (40-60°) and air-dried to give the title compound as a bright yellow solid (57.83 g, 92%).

[ES MS] m/z 284 (MH⁺).

(c) N²-(2,2-Dimethyl-1,3-dioxan-5-yl)-6-(methyloxy)-2,3-pyridinediamine

N-(2,2-Dimethyl-1,3-dioxan-5-yl)-6-(methyloxy)-3-nitro-2-pyridinamine (35.00 g, 123.6 mmol) was divided into 2 aliquots, each of which was taken up in 1,4-dioxane (500 ml) and hydrogenated over 10% Pd on carbon (paste, 1:1 w:w with water, 4.00 g) under 1 atmosphere hydrogen pressure, at room temperature for 18 h. The mixtures were filtered with suction though Celite, using argon blanket and taking care to minimise contact of the product with air. The solids were washed with 1,4-dioxane and the combined filtrate plus washings were evaporated under reduced pressure to give the title compound as a deep purple oil. This was used immediately in the next step.

[ES MS] m/z 254 (MH⁺).

(d) Ethyl N-[2-[(2,2-dimethyl-1,3-dioxan-5-yl)amino]-6-(methyloxy)-3-pyridinyl]glycinate Crude N²-(2,2-dimethyl-1,3-dioxan-5-yl)-6-(methyloxy)-2,3-pyridinediamine (123.6 mmol) was dissolved in anhydrous DMF (500 ml) under argon and anhydrous K₂CO₃ (37.56 g) was added, followed by ethyl bromoacetate (12.31 ml). The mixture was stirred at room temperature overnight. The solvent was removed under reduced pressure and the resulting reddish-brown slurry was partitioned between DCM (1.2 L) and water (300 ml). The organic phase was separated and washed with water (300 ml), dried over Na₂SO₄, filtered and evaporated under reduced pressure to give a dark red oil, this was taken up in a minimum of DCM and purified by column chromatography on silica (eluted with 5%-60% EtOAc in petroleum ether (40-60°)). Appropriate fractions were combined and evaporated under reduced pressure to give the title compound as a dark orange oil (35.42 g, 84%).

[ES MS] m/z 340 (MH⁺).

(e) 4-(2,2-Dimethyl-1,3-dioxan-5-yl)-6-(methyloxy)-1,4-dihydropyrido[2,3-b]pyrazin-3(2H)-one Ethyl N-[2-[(2,2-dimethyl-1,3-dioxan-5-yl)amino]-6-(methyloxy)-3-pyridinyl]glycinate (35.42 g, 104.4 mmol) was dissolved in dry THF (500 ml) and the solution was added dropwise over 2 h to a cooled (0° C.) suspension of sodium hydride (4.173 g of 60% w:w dispersion in oil) in dry THF (500 ml) under argon. During the addition the colour of the suspension changed from orange to green. The mixture was stirred at 0° C. for a further 15 minutes, then allowed to warm to room temperature and stirred at rt for 1 h. The mixture was cooled to 0° C. and saturated NH$_4$Cl (15 ml) was added cautiously with vigorous stirring (effervescence observed). After effervescence had ceased, the mixture was allowed to warm to room temperature and stirred for 4 h then diluted with EtOAc (500 ml) and filtered with suction. The solids were washed with EtOAc (300 ml) and the combined filtrate plus washings were evaporated under reduced pressure to give a dark brown solid. This was stirred with petroleum ether (40-60°) (500 ml) plus EtOAc (20 ml) and filtered with suction to give a lighter brown solid which was washed with petroleum ether (40-60°) (100 ml) and air-dried to afford the title compound (25.37 g, 82%).

[ES MS] m/z 316 (MNa$^+$).

(f) 4-(2,2-Dimethyl-1,3-dioxan-5-yl)-6-(methyloxy)pyrido[2,3-b]pyrazin-3(4H)-one 4-(2,2-Dimethyl-1,3-dioxan-5-yl)-6-(methyloxy)-1,4-dihydropyrido[2,3-b]pyrazin-3(2H)-one (25.37 g) and activated manganese dioxide (120 g) were stirred in DCM (500 ml) at room temperature for 2 h. The mixture was filtered with suction and the solids were washed with DCM (2×100 ml). The combined filtrate plus washings were evaporated under reduced pressure to give a brown foam; this was purified by column chromatography on silica (eluting with 0%-100% EtOAc in petroleum ether (40-60°)). Appropriate fractions were combined and evaporated under reduced pressure to give the title compound as a light tan solid (17.40 g, 69%).

[ES MS] m/z 314 (MNa$^+$).

(g) 4-[2-Hydroxy-1-(hydroxymethyl)ethyl]-6-(methyloxy)pyrido[2,3-b]pyrazin-3(4H)-one 4-(2,2-Dimethyl-1,3-dioxan-5-yl)-6-(methyloxy)pyrido[2,3-b]pyrazin-3(4H)-one (17.40 g, 59.7 mmol) was dissolved in THF (220 ml) to give a dark yellow solution. 1M HCl aq. (200 ml) was added (transient blue and green colours appeared in the solution) and the now light yellow solution was stirred at room temperature for 1 h. The mixture was concentrated to ca. 300 ml on a rotary evaporator using a cold water bath (some solid was precipitated during this procedure) then was stirred vigorously while solid sodium hydrogen carbonate was added in portions (caution: effervescence) until the mixture was ca. pH 8. The resulting yellow solid was collected by filtration with suction, washed with water (2×20 ml) and air-dried to give the title compound as an amorphous yellow solid (13.805 g, 91%).

[ES MS] m/z 252 (MH$^+$).

(h) (3,8-Dioxo-1,2-dihydro-3H 8H-2a,5,8a-triazaacenaphthylen-2-yl)methyl methanesulfonate In a 1 L round-bottomed flask was placed 4-[2-hydroxy-1-(hydroxymethyl)ethyl]-6-(methyloxy)pyrido[2,3-b]pyrazin-3(4H)-one (11.330 g, 45.1 mmol). Anhydrous chloroform (280 ml) was added, followed by Et$_3$N (31.4 ml, 225 mmol), and methanesulfonic anhydride (31.4 g, 180 mmol) to give a dark yellow-brown solution. During addition of the methanesulfonic anhydride, an exothermic reaction occurred which was sufficient to cause the solvent to boil. The mixture was stirred vigorously at reflux under argon for 4.5 h. The mixture was allowed to cool to room temperature, diluted with DCM to ca. 600 ml, and washed with water (200 ml). The organic phase was separated, and the aqueous phase was extracted with DCM (2×200 ml). The combined organic extracts were dried over anhydrous Na$_2$SO$_4$, filtered, and evaporated under reduced pressure to give crude mesylate as dark brown oil. This was left overnight under 40-60° petrol (200 ml) plus DCM (50 ml). The resulting solid was isolated by filtration with suction, washed with 4:1 petrol:DCM (2×50 ml) and air-dried to give the title compound as a brown amorphous solid (6.950 g, 52%)

[ES MS] m/z 298 (MH$^+$).

(i) 1,1-Dimethylethyl {1-[(3,8-dioxo-1,2-dihydro-3H,8H-2a,5,8a-triazaacenaphthylen-2-yl)methyl]-4-piperidinyl}carbamate Crude (3,8-dioxo-1,2-dihydro-3H,8H-2a,5,8a-triazaacenaphthylen-2-yl)methyl methanesulfonate (6.950 g, 23.38 mmol) was dissolved in dry CH$_3$CN (200 ml) and the mixture was treated with pyridine (7.55 ml, 94.0 mmol) followed by 1,1-dimethylethyl 4-piperidinylcarbamate (10.30 g, 51.4 mmol). The mixture was stirred at reflux under argon for 3 h then at 50° C. over the weekend. The mixture was then stirred at 90° C. for 2 h, then the volatiles were removed under reduced pressure and the residue was partitioned between DCM (600 ml) and water (100 ml). The organic phase was separated and the aqueous phase was extracted with DCM (2×200 ml). The combined organic extracts were washed with water (2×100 ml) dried over anhydrous Na$_2$SO$_4$, filtered and evaporated under reduced pressure to give a dark tan solid; this was taken up in a minimum of 5% MeOH in DCM and applied chromatographed, eluting with 0-10% MeOH in DCM. Appropriate fractions were combined and evaporated under reduced pressure to give the title compound as an amorphous pale tan solid (5.444 g, 57%).

[ES MS] m/z 424 (MNa$^+$), 402 (MH$^+$).

(j) 2-[(4-Amino-1-piperidinyl)methyl]-1,2-dihydro-3H 8H-2a,5,8a-triazaacenaphthylene-3,8-dione (Racemic and Enantiomer 1 and 2 synthesis)

Method A (Racemic Synthesis):

1,1-Dimethylethyl {1-[(3,8-dioxo-1,2-dihydro-3H,8H-2a,5,8a-triazaacenaphthylen-2-yl)methyl]-4-piperidinyl}carbamate (1.630 g, 4.06 mmol) was suspended in DCM (30 ml) and 4M HCl in 1,4-dioxane (15 ml) was added to give a bright yellow suspension (and gas evolution). The bright yellow mixture was allowed to stand at room temperature for 1 h. LCMS showed no starting material remaining. The solvents were removed under reduced pressure and the residue was dried under reduced pressure overnight to give the dihydrochloride salt of the title compound as an amorphous tan solid (1.760 g (>theoretical yield for the dihydrochloride owing to the presence of residual solvent)).

A portion of the crude dihydrochloride (0.513 g) was dissolved in MeOH (4 ml) plus water (1 ml) and applied to an SCX column (10 g) (preconditioned with 2 column volumes of MeOH). The column was then eluted, under gravity, using (i) MeOH (2×50 ml), (ii) 0.5M ammonia in MeOH (3×50 ml fractions). Appropriate fractions were combined and evaporated under reduced pressure to give the crude title compound as a tan amorphous solid (410 mg), which contained MeOH-insoluble material not apparent by LCMS (possibly NH$_4$Cl). The product was shaken with MeOH (30 ml) and the suspension was filtered. The solid was washed with MeOH (20 ml)

and the combined filtrate and washings were evaporated under reduced pressure to give the title compound (360 mg, 87%).

[ES MS] m/z 302 (MH+).

Method B 1,1-Dimethylethyl {1-[(3,8-dioxo-1,2-dihydro-3H,8H-2a,5,8a-triazaacenaphthylen-2-yl)methyl]-4-piperidinyl}carbamate (9.735 g, 24.25 mmol) was suspended in DCM (90 ml) and 4M HCl in 1,4-dioxane (45 ml) was added to give a bright yellow suspension (and gas evolution). The bright yellow mixture was stirred at room temperature for 1 h. The solvents were removed under reduced pressure to give the crude dihydrochloride as a bright yellow amorphous solid (10.420 g) containing residual solvent).

The racemic dihydrochloride (10.42 g) was resolved into its two enantiomers by preparative chiral HPLC using a 4 inch Chiralpak AD (20 microns) preparative column with 50:50:0.1 $CH_3CN$:MeOH:isopropylamine as the mobile phase. The alpha value was 3.1 and baseline resolution was observed for all 3 runs. There was no overlap fraction and both enantiomers (as the free bases) were isolated in >99.8 ee each.

(2R)-2-[(4-Amino-1-piperidinyl)methyl]-1,2-dihydro-3H,8H-2a,5,8a-triazaacenaphthylene-3,8-dione (first component eluted): (3.30 g, light beige solid, chiral HPLC: 100% ee).

[ES MS] m/z 302 (MH+).

Optical rotation: alpha D=120° (C=1.00, MeOH, 21.8° C.).

(2S)-2-[(4-Amino-1-piperidinyl)methyl]-1,2-dihydro-3H,8H-2a,5,8a-triazaacenaphthylene-3,8-dione (second component eluted): (3.30 g, light beige solid, chiral HPLC: 99.8% ee).

[ES MS] m/z 302 (MH+).

Optical rotation: alpha D=+1220 (C=1.00, MeOH, 21.8° C.).

(k) Title compound: (2R)-2-[(4-{[(5-Chloro-6-methyl-3-pyridinyl)methyl]amino}-1-piperidinyl)methyl]-1,2-dihydro-3H 8H-2a,5,8a-triazaacenaphthylene-3,8-dione hydrochloride A solution of (2R)-2-[(4-amino-1-piperidinyl)methyl]-1,2-dihydro-3H,8H-2a,5,8a-triazaacenaphthylene-3,8-dione (63.4 mg, 0.210 mmol) and 5-chloro-6-methyl-3-pyridinecarbaldehyde (for a synthesis see WO2006/137485 A1 Example 256) (32.7 mg, 0.210 mmol) in a mixture of DCM (1.5 ml) and MeOH (0.5 ml) was stirred at room temperature for 30 min. $NaBH(OAc)_3$ (312 mg, 1.473 mmol) was then added and the mixture stirred at room temperature. The reaction was monitored by LCMS and when full conversion was observed, it was quenched with 10% $NaHCO_3$ and extracted with DCM. The organic layer was dried ($MgSO_4$), filtered, and concentrated.

Purification by flash chromatography using Flashmaster II, a 2 g silica gel cartridge, and mixtures of DCM and MeOH as eluent afforded 34.6 mg (0.078 mmol, 37%) of the expected product as the free base. It was dissolved in MeOH (6 ml). HCl (4 M solution in 1,4-dioxane, 0.019 ml, 0.078 mmol) was added dropwise and the mixture stirred at room temperature for 35 min. Then, the solvent was evaporated. MeOH and hexane were used to help removal of dioxane. (2R)-2-[(4-{[(5-chloro-6-methyl-3-pyridinyl)methyl]amino}-1-piperidinyl)methyl]-1,2-dihydro-3H,8H-2a,5,8a-triazaacenaphthylene-3,8-dione hydrochloride (60.4 mg, 0.127 mmol) was obtained as a yellow solid.

$^1$H-NMR (d, ppm, DMSO-$d_6$): 9.07 (bs, 1H), 8.52 (s, 1H), 8.10 (s, 1H), 7.85 (d, 1H), 7.73 (s, 1H), 6.25 (d, 1H), 5.07-4.99 (s, 1H), 4.36-4.17 (s, 4H), 3.04-2.96 (m, 3H), 2.86-2.72 (m, 2H), 2.55 (s, 3H), 2.25-1.96 (m, 5H), 1.53-1.46 (m, 2H). [ES MS] m/z 441 (MH+).

Example 2

Compound: Synthesis of (2R)-2-[(4-{[(5-chloro-6-methyl-3-pyridinyl)methyl]amino}-1-piperidinyl)methyl]-1,2-dihydro-3H,8H-2a,5,8a-triazaacenaphthylene-3,8-dione hydrochloride, using Preparative Scheme (4)

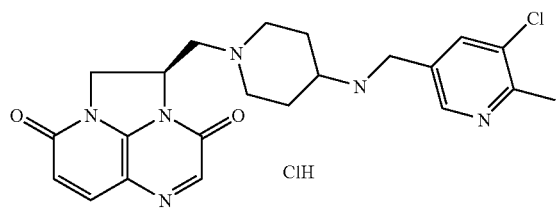

(a) (2R)-2-{[6-(Methyloxy)-3-nitro-2-pyridinyl]amino}-3-[(phenylmethyl)oxy]-1-propanol To a solution of (R)-2-amino-3-benzyloxy-1-propanol (698.4 g, 3.931 mol) in EtOH (3.6 L) was added $Et_3N$ (1.27 L, 9.11 mol) in portions over 10 min. Then a solution of 2-chloro-6-methoxy-3-nitropyridine (672.7 g, 3.567 mol) in EtOH (0.6 L) was added in portions over 10 min. The mixture was heated at 78° C. for 2 h. The reaction mixture was cooled to room temperature and added to stirred ice/$H_2O$ (8.4 L). The mixture was extracted with EtOAc (9+6+3 L). The extracts were washed with brine (6 L), dried over $MgSO_4$ (~900 g), filtered and evaporated to give (2R)-2-{[6-(methyloxy)-3-nitro-2-pyridinyl]amino}-3-[(phenylmethyl)oxy]-1-propanol (1373.1 g, 115%) as an orange oil.

(b) N-((1S)-2-{[(1,1-Dimethylethyl)(dimethyl)silyl]oxy}-1-{[(phenylmethyl)oxy]methyl}ethyl)-6-(methyloxy)-3-nitro-2-pyridinamine To a solution of (2R)-2-{[6-(methyloxy)-3-nitro-2-pyridinyl]amino}-3-[(phenylmethyl)oxy]-1-propanol (675.8 g) in DMF (2.37 L) was added chloro(1,1-dimethylethyl)dimethylsilane (382.0 g) in portions. Then, imidazole (331.2 g) was added in portions and the mixture was stirred at room temperature for 1.5 h. The reaction mixture was evaporated and the resulting orange gum was partitioned between EtOAc (3 L) and $H_2O$ (3 L). The layers were separated and the aqueous was extracted with EtOAc (2.5+2 L). The organic layers were combined, dried over $MgSO_4$ (~500 g), filtered and evaporated to give an orange oil. The crude product was purified by column chromatography (10 kg silica, 9:1 heptane:EtOAc) to give N-((1S)-2-{[(1,1-dimethylethyl)(dimethyl)silyl]oxy}-1-{[(phenylmethyl)oxy]methyl}ethyl)-6-(methyloxy)-3-nitro-2-pyridinamine (774.7 g, 100%) as a bright yellow solid.

(c) $N^2$-((1S)-2-{[(1,1-Dimethylethyl)(dimethyl)silyl]oxy}-1-{[(phenylmethyl)oxy]methyl}ethyl)-6-(methyloxy)-2,3-pyridinediamine To a solution of N-((1S)-2-{[(1,1-dimethylethyl)(dimethyl)silyl]oxy}-1-{[(phenylmethyl)oxy]methyl}ethyl)-6-(methyloxy)-3-nitro-2-pyridinamine (642.6 g, 1.436 mol) in MeOH (12 L) was added a suspension of zinc dust (938 g, 14.35 mol) in MeOH (4 L). Acetic acid (411 ml, 7.18 mol) was added dropwise over ~30 min such that the temperature remained below 36° C. When the addition was complete the mixture was stirred for 15 min. The reaction mixture was filtered through celite and the cake was washed with EtOAc (8 L). The mixture was washed with brine (8 L) and the layers were separated. The aqueous phase was extracted with EtOAc (8+6 L) then the organic phases were combined, washed with saturated NaHCO$_3$ (8 L), brine (8 L), dried over MgSO$_4$ (1 kg) and filtered. The filtrate was evaporated to give 478 g (80%) of N$^2$-((1S)-2-{[(1,1-dimethylethyl)(dimethyl)silyl]oxy}-1-{[(phenylmethyl)oxy]methyl}ethyl)-6-(methyloxy)-2,3-pyridinediamine as a dark red viscous oil.

(d) Ethyl N-[2-[((1S)-2-{[(1,1-dimethylethyl)(dimethyl)silyl]oxy}-1-{[(phenylmethyl)oxy]methyl}ethyl)amino]-6-(methyloxy)-3-pyridinyl]glycinate To a solution of N$^2$-((1S)-2-{[(1,1-dimethylethyl)(dimethyl)silyl]oxy}-1-{[(phenylmethyl)oxy]methyl}ethyl)-6-(methyloxy)-2,3-pyridinediamine (673.1 g, 1.612 mol) in DMF (10 L) was added K$_2$CO$_3$ (490.1 g, 3.546 mol). Ethyl bromoacetate (196.6 ml, 1.77 mol) was added to the mixture over 15 min and the reaction mixture was stirred at room temperature. After 3 h, the reaction was quenched in H$_2$O (10 L) then partitioned with EtOAc (10 L). The layers were separated and the aqueous was extracted with EtOAc (7 L). The organic phases were combined, washed with H$_2$O (7 L) and brine (7 L), dried over MgSO$_4$ (1 kg), filtered and evaporated. The resulting dark oil (853 g) was purified by column chromatography (9 kg silica, mixtures of heptane and EtOAc as eluent) to give ethyl N-[2-[((1S)-2-{[(1,1-dimethylethyl)(dimethyl)silyl]oxy}-1-{[(phenylmethyl)oxy]methyl}ethyl)amino]-6-(methyloxy)-3-pyridinyl]glycinate (672.0 g, 83%) as a dark oil.

(e) 4-((1S)-2-{[(1,1-Dimethylethyl)(dimethyl)silyl]oxy}-1-{[(phenylmethyl)oxy]methyl}ethyl)-6-(methyloxy)-1,4-dihydropyrido[2,3-b]pyrazin-3(2H)-one To a solution of NaH (50.5 g, 57-63% dispersion in mineral oil, 1.26 mol) in THF (8.5 L) was added ethyl N-[2-[((1S)-2-{[(1,1-dimethylethyl)(dimethyl)silyl]oxy}-1-{[(phenylmethyl)oxy]methyl}ethyl)amino]-6-(methyloxy)-3-pyridinyl]glycinate (577.8 g, 1.147 mol) at −5° C. When the addition was complete the mixture was warmed to room temperature and stirred for 30 min. The reaction was quenched by the addition of saturated aqueous NH$_4$Cl (610 ml) and the mixture was stirred for 10 min. Na$_2$SO$_4$ (1 kg) was added and the mixture was stirred for 10 min before being filtered through celite. The filter cake was washed with EtOAc (5 L). The filtrate was evaporated and the dark purple oil was purification by column chromatography and mixtures of heptane and EtOAc as eluent to give 477 g (91%) of 4-((1S)-2-{[(1,1-dimethylethyl)(dimethyl)silyl]oxy}-1-{[(phenylmethyl)oxy]methyl}ethyl)-6-(methyloxy)-1,4-dihydropyrido[2,3-b]pyrazin-3(2H)-one as a viscous purple oil.

(f) 4-[(1S)-2-{[(1,1-Dimethylethyl)(dimethyl)silyl]oxy}-1-(hydroxymethyl)ethyl]-6-(methyloxy)-1,4-dihydropyrido[2,3-b]pyrazin-3(2H)-one A mixture of 4-((1S)-2-{[(1,1-dimethylethyl)(dimethyl)silyl]oxy}-1-{[(phenylmethyl)oxy]methyl}ethyl)-6-(methyloxy)-1,4-dihydropyrido[2,3-b]pyrazin-3(2H)-one (250.4 g, 0.547 mol), Pearlman's catalyst (25 g) and 10% Pd/C (25 g, 50% wet) in EtOH (5 L) was stirred at 50° C. under 5 bar of H$_2$ for 3.5 h. The reaction mixture was filtered through celite and the filtrate was evaporated to give 4-[(1S)-2-{[(1,1-dimethylethyl)(dimethyl)silyl]oxy}-1-(hydroxymethyl)ethyl]-6-(methyloxy)-1,4-dihydropyrido[2,3-b]pyrazin-3(2H)-one (191.2 g, 95%) as a dark blue solid.

(g) 4-[(1S)-2-{[(1,1-Dimethylethyl)(dimethyl)silyl]oxy}-1-(hydroxymethyl)ethyl]-6-(methyloxy)pyrido[2,3-b]pyrazin-3(4H)-one A solution of 4-[(1S)-2-{[(1,1-dimethylethyl)(dimethyl)silyl]oxy}-1-(hydroxymethyl)ethyl]-6-(methyloxy)-1,4-dihydropyrido[2,3-b]pyrazin-3(2H)-one (494.1 g, 1.34 mol) and MnO$_2$ (584.4 g, 6.72 mol) in DCM (18 L) was stirred at room temperature for 1 h. The mixture was filtered through celite and the filtrate was evaporated to give a purple/white solid. The crude was purified by column chromatography and mixtures of heptane and EtOAc as eluent to give of 451.6 g (66%) of 4-[(1S)-2-{[(1,1-dimethylethyl)(dimethyl)silyl]oxy}-1-(hydroxymethyl)ethyl]-6-(methyloxy)pyrido[2,3-b]pyrazin-3(4H)-one.

$^1$H-NMR (δ, ppm, CDCl$_3$): 8.15 (s, 1H), 8.03 (d, 1H), 6.74 (d, 1H), 6.00 (bs, 1H), 4.30-4.20 (m, 4H), 4.04-3.96 (m, 1H), 4.01 (s, 3H), 0.66 (s, 9H), −0.046 (s, 3H), −0.166 (s, 3H).

[ES MS] m/z 366 (MH$^+$).

(h) (2S)-2-({[(1,1-Dimethylethyl)(dimethyl)silyl]oxy}methyl)-1,2-dihydro-3H,8H-2a,5,8a-triazaacenaphthylene-3,8-dione To a solution of 4-[(1S)-2-{[(1,1-dimethylethyl)(dimethyl)silyl]oxy}-1-(hydroxymethyl)ethyl]-6-(methyloxy)pyrido[2,3-b]pyrazin-3(4H)-one (1 g, 2.74 mmol) in CHCl$_3$ (50 mL) was added Et$_3$N (0.953 mL, 6.84 mmol) followed by a solution of methanesulfonic anhydride (0.953 g, 5.47 mmol) in CHCl$_3$ (50 mL). The reaction mixture was stirred at reflux temperature for 5 h. The crude of reaction was diluted with water, washed with NaCl, dried (MgSO$_4$), filtered, and concentrated. Purification by flash chromatography using a 40 g silica gel cartridge, and mixtures of DCM and MeOH as eluent afforded (2S)-2-({[(1,1-dimethylethyl)(dimethyl)silyl]oxy}methyl)-1,2-dihydro-3H,8H-2a,5,8a-triazaacenaphthylene-3,8-dione (0.806 g, 88%) as a tan solid.

$^1$H-NMR (δ, ppm, CDCl$_3$): 7.84 (s, 1H), 7.75 (d, 1H), 6.35 (d, 1H), 5.13-5.07 (m, 1H), 4.53-4.35 (m, 3H), 3.82 (dd, 1H), 0.66 (s, 9H), 0.00 (s, 3H), −0.13 (s, 3H). [ES MS] m/z 334 (MH$^+$).

(i) (2S)-2-(Hydroxymethyl)-1,2-dihydro-3H,8H-2a,5,8a-triazaacenaphthylene-3,8-dione A suspension of (2S)-2-({[(1,1-dimethylethyl)(dimethyl)silyl]oxy}methyl)-1,2-dihydro-3H,8H-2a,5,8a-triazaacenaphthylene-3,8-dione (42.6 g, 128 mmol) and Dowex 50X2-200 ion exchange resin (50 g, 128 mmol) in MeOH (1000 mL) was stirred at room temperature for 15 h. The reaction mixture was filtered to give (2S)-2-(hydroxymethyl)-1,2-dihydro-3H,8H-2a,5,8a-triazaacenaphthylene-3,8-dione (26.55 g, 121 mmol, 95%).

[ES MS] m/z 220 (MH$^+$).

(j) [(2S)-3,8-Dioxo-1,2-dihydro-3H,8H-2a,5,8a-triazaacenaphthylen-2-yl]methyl benzenesulfonate To the suspension of (2S)-2-(hydroxymethyl)-1,2-dihydro-3H,8H-2a,5,8a-triazaacenaphthylene-3,8-dione (26.5 g, 121 mmol) in DCM (320 ml) was added benzenesulfonyl chloride (23.38 ml, 181 mmol) followed by Et$_3$N (39.6 ml, 284 mmol). The reaction mixture was heated at gentle reflux at 42° C. for 2 h. Then, the reaction was cooled to 5° C. and 2-(dimethylamino)ethanol (7.30 ml, 72.5 mmol) was added dropwise. The crude was stirred at room temperature for 30 min and TBME (600 ml) was added. The obtained solid was filtered. The resulting solid was suspended in 100 ml 1N HCl and washed with water and TBME, dried to give [(2S)-3,8-dioxo-1,2-dihydro-3H,8H-2a,5,8a-triazaacenaphthylen-2-yl]methyl benzenesulfonate (37.04 g, 85%) as a cream solid.

$^1$H-NMR (δ, ppm, CDCl$_3$): 7.79-7.69 (m, 5H), 7.57-7.52 (m, 2H), 6.38 (d, 1H), 5.19-5.12 (m, 1H), 4.92 (dd, 1H), 4.47-4.38 (m, 3H). [ES MS] m/z 360 (MH$^+$).

(k) Title compound: (2R)-2-[(4-{[(5-Chloro-6-methyl-3-pyridinyl)methyl]amino}-1-piperidinyl)methyl]-1,2-dihydro-3H 8H-2a,5,8a-triazaacenaphthylene-3,8-dione hydrochloride To a suspension of [(2S)-3,8-dioxo-1,2-dihydro-3H,8H-2a,5,8a-triazaacenaphthylen-2-yl]methyl benzenesulfonate (14.5 g, 40.3 mmol) in CH$_3$CN (100 ml) was added at 0° C. N-[(5-chloro-6-methyl-3-pyridinyl)methyl]-4-piperidinamine (for a synthesis see Preparation 11) (11.61 g, 48.4 mmol) and N,N-diisopropylethylamine (7.03 ml, 40.3 mmol). The reaction mixture was stirred at 77° C. for 6 h. The reaction was allowed to cooled to room temperature and then to 0° C. in an ice bath. The precipitated solid was filtrated under vacuum and washed with CH$_3$CN, to give a first filtrate. Then, the isolated solid was washed again with H$_2$O and TBME to give a second filtrate.

The resulting solid was collected to give a first batch of (2R)-2-[(4-{[(5-chloro-6-methyl-3-pyridinyl)methyl]amino}-1-piperidinyl)methyl]-1,2-dihydro-3H,8H-2a,5,8a-triazaacenaphthylene-3,8-dione (3.5 g, 20%) as a yellow solid.

The first filtrate was concentrated under vacuum and dissolved in DCM. 2N HCl was added until pH 1-2 and the organic phase was extracted and discarded. 10% NaHCO$_3$ was added to the aqueous phase until pH 9, and the organic phase was extracted with DCM, washed with NaCl, dried (MgSO$_4$), filtered and concentrated. Purification by flash chromatography using a 50 g silica gel cartridge, and mixtures of DCM and MeOH as eluent afforded a second batch of (2R)-2-[(4-{[(5-chloro-6-methyl-3-pyridinyl)methyl]amino}-1-piperidinyl)methyl]-1,2-dihydro-3H,8H-2a,5,8a-triazaacenaphthylene-3,8-dione (2.09 g, 12%).

The second filtrate was extracted with DCM and DCM/MeOH 95/5, dried (Na$_2$SO$_4$), filtered and concentrated to give a third batch of (2R)-2-[(4-{[(5-chloro-6-methyl-3-pyridinyl)methyl]amino}-1-piperidinyl)methyl]-1,2-dihydro-3H,8H-2a,5,8a-triazaacenaphthylene-3,8-dione free base (7.75 g, 44%). Total yield of 76%.

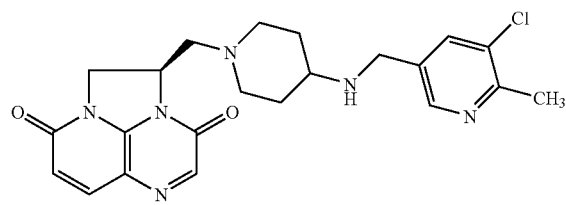

$^1$H-NMR (δ, ppm, CDCl$_3$): 8.30 (s, 1H), 7.82 (s, 1H), 7.76 (d, 1H), 7.64 (s, 1H), 6.38 (d, 1H), 5.06-4.98 (m, 1H), 4.57-4.52 (m, 1H), 4.41-4.33 (m, 1H), 3.76 (s, 2H), 3.15 (dd, 1H), 2.96-2.92 (m, 1H), 2.73-2.63 (m, 2H), 2.60 (s, 3H), 2.51-2.45 (m, 1H), 2.36-2.20 (m, 2H), 1.88-1.80 (m, 2H), 1.35-1.31 (m, 2H). [ES MS] m/z 441 (MH$^+$).

To a solution of this free base (3.5 g, 7.94 mmol) in DCM (80 ml) was added HCl (4M solution in 1,4-dioxane, 2.0 ml, 8.0 mmol) dropwise. After stirring at room temperature for 1 h, the solvent was evaporated under vacuum and the crude was dispersed in hexane/DCM. The obtained solid was collected by filtration to afford (2R)-2-[(4-{[(5-Chloro-6-methyl-3-pyridinyl)methyl]amino}-1-piperidinyl)methyl]-1,2-dihydro-3H,8H-2a,5,8a-triazaacenaphthylene-3,8-dione hydrochloride (3.2 g, 84%) as a yellow solid.

$^1$H-NMR (d, ppm, DMSO-d$_6$): 9.07 (bs, 1H), 8.52 (s, 1H), 8.10 (s, 1H), 7.85 (d, 1H), 7.73 (s, 1H), 6.25 (d, 1H), 5.07-4.99 (s, 1H), 4.36-4.17 (s, 4H), 3.04-2.96 (m, 3H), 2.86-2.72 (m, 2H), 2.55 (s, 3H), 2.25-1.96 (m, 5H), 1.53-1.46 (m, 2H). [ES MS] m/z 441 (MH$^+$).

Example 9

Compound: Synthesis of (1R)-1-{[4-({[6-(Trifluoromethyl)-3-pyridinyl]methyl}amino)-1-piperidinyl]methyl}-1,2-dihydro-4H,9H-imidazo[1,2,3-ij]-1,8-naphthyridine-4,9-dione hydrochloride

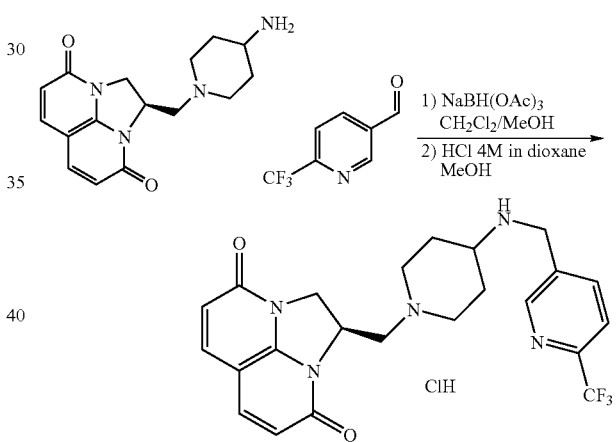

A solution of (1R)-1-[(4-amino-1-piperidinyl)methyl]-1,2-dihydro-4H,9H-imidazo[1,2,3-ij]-1,8-naphthyridine-4,9-dione (see Example 1 step (j) above: 400 mg, 1.33 mmol) and 6-(trifluoromethyl)-3-pyridinecarbaldehyde (233 mg, 1.33 mmol, from Apollo) in a mixture of DCM (5 ml) and MeOH (5 ml) was stirred at room temperature for 2 hour. NaBH(OAc)$_3$ (1.7 g, 7.99 mmol) was then added and the mixture was stirred at room temperature. The reaction was monitored by LCMS. More aldehyde (47 mg, 0.27 mmol), and NaHB(OAc)$_3$ (421 mg, 1.98 mmol) were added and when full conversion was observed, it was quenched with 10% NaHCO$_3$ and extracted with DCM. The organic layer was dried (MgSO$_4$), filtered, and concentrated. Purification by flash chromatography using a 70 g silica gel cartridge, and mixtures of DCM and MeOH as eluent afforded 463 mg (75%) of the expected product as the free base. It was dissolved in MeOH (50 ml). HCl (4M solution in 1,4-dioxane, 0.25 ml, 1 mmol) was added dropwise. After stirring at room temperature for 20 min, the solvent was evaporated. (1R)-1-{[4-({[6-(Trifluoromethyl)-3-pyridinyl]methyl}amino)-1-piperidinyl]methyl}-1,2-dihydro-4H,9H-imidazo[1,2,3-ij]-1,8- naphthyridine-4,9-dione hydrochloride (238 mg, 0.480 mmol, 36%) was obtained as a beige solid.

¹H-NMR (δ, ppm, d-DMSO): 10.21 (bs, 1H), 9.01 (s, 1H), 8.43 (d, 1H), 8.02 (d, 1H), 7.79 (dd, 2H), 6.22 (d, 2H), 5.40 (bs, 1H), 4.50-4.36 (m, 4H), 3.80-3.66 (m, 5H), 3.17 (bs, 2H), 2.17 (bs, 4H). [ES MS] m/z 460 (MH⁺).

Example 11

Compound: Synthesis of (1R)-1-{[4-({[6-(trifluoromethyl)-3-pyridinyl]methyl}amino)-1-piperidinyl]methyl}-1,2-dihydro-3H,8H-2a,5,8a-triazaacenaphthylene-3,8-dione, using Preparative Scheme (2)

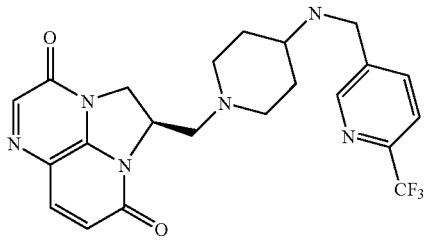

(a) 6-(Methyloxy)-3-nitro-2-pyridinamine

A solution/suspension of 2-chloro-6-(methyloxy)-3-nitropyridine (65.7 g, 348 mmol) in 2M ammonia in MeOH (500 ml, 1000 mmol) and aqueous ammonia (500 ml, 348 mmol) was stirred at 65° C. for 18 h. The reaction was cooled down and the solid filtered off and washed with water (2×100 ml). The solid was dried in the vacuum oven at 40° C. overnight to afford the product as a bright yellow solid (52.14 g, 84% purity by NMR, 74%).

[ES MS] m/z 170 (MH⁺).

(b) 6-(Methyloxy)-2,3-pyridinediamine 6-(Methyloxy)-3-nitro-2-pyridinamine (26 g, 129 mmol) was suspended in EtOH (500 ml) at room temperature under argon and then treated with palladium on carbon (15 g, 14.10 mmol) (10% paste). The reaction was stirred under 1 atmosphere of hydrogen overnight. The reaction was filtered through a Celite pad and the pad washed with EtOH (500 ml). EtOH was evaporated to afford the product as a purple oil (20.68 g, slightly impure).

[ES MS] m/z 140 (MH⁺).

(c) Ethyl N-[2-amino-6-(methyloxy)-3-pyridinyl]glycinate 6-(Methyloxy)-2,3-pyridinediamine (21.7 g, estimated 87% purity, 136 mmol) was dissolved in CH₃CN (500 ml) at room temperature under argon and then treated with K₂CO₃ (24.38 g, 176 mmol) and ethyl bromoacetate (18.13 ml, 163 mmol). The reaction was stirred at room temperature overnight. The CH₃CN was then removed in vacuo. The reaction was repeated using more 6-(methyloxy)-2,3-pyridinediamine (20.68 g, 87% purity, 129 mmol), in CH₃CN (500 ml), K₂CO₃ (23.23 g) and ethyl bromoacetate (17.27 g) and the reaction was again stirred at room temperature overnight and the CH₃CN was then removed in vacuo. The residues were partitioned between water (1 L) and EtOAc (1 L) and the layers separated. The aqueous layer was extracted once more with EtOAc (1 L) and the combined organic extracts were dried over MgSO₄, filtered and evaporated to afford a purple oil (64 g). The oil was treated with DCM (300 ml) and the insoluble impurities filtered off. The DCM solution was loaded onto a 800 g silica column and eluted with 0-2% MeOH/DCM to afford 40.6 g of desired product as a brown solid (LCMS and NMR consistent with 75% desired product with 15% cyclized product 6-(methyloxy)-1,4-dihydropyrido[2,3-b]pyrazin-3(2H)-one and 6.4 g of cyclized product 6-(methyloxy)-1,4-dihydropyrido[2,3-b]pyrazin-3(2H)-one as a purple solid.

[ES MS] m/z 226 (MH⁺).

(d) 6-(Methyloxy)-1,4-dihydropyrido[2,3-b]pyrazin-3(2H)-one

Ethyl N-[2-amino-6-(methyloxy)-3-pyridinyl]glycinate (40.6 g, 135 mmol) was dissolved in THF (1 L) at room temperature under argon and treated with potassium tert-butoxide (15.17 g, 135 mmol). After 2 h at room temperature saturated NH₄Cl (500 ml) was added and the THF evaporated. Water (500 ml) was added followed by 20% MeOH/DCM (1 L); the insoluble material was filtered off, washed with Et₂O and dried in the vacuum oven at 40° C. overnight to afford the desired product as a yellow solid (15.3 g): LCMS and NMR consistent with product (9% of oxidized material present by NMR).

The two phases were transferred to a separating funnel and separated. The aqueous layer was extracted twice more with 20% MeOH/DCM (2×500 ml) and the combined organic extracts were dried over MgSO₄ filtered and evaporated to afford a brown solid which was washed with plenty of Et₂O to afford more of the desired product as a pale green solid (7.7 g): LCMS and NMR consistent with product (20% of oxidized material present by NMR).

[ES MS] m/z 180 (MH⁺).

Alternative Procedure:

Ethyl N-[2-amino-6-(methyloxy)-3-pyridinyl]glycinate (16.2 g, 72 mmol) was dissolved in tetrahydrofuran (500 ml) and cooled to 0° C. (ice bath cooling) under argon. This was then treated with potassium tert-butoxide (1M in THF, 80 ml, 80 mmol). After 1.5 h the reaction was treated with AcOH (80 mmol) and evaporated to give a dark solid. This was triturated with water (200 ml), filtered and dried in vacuo (~13 g, quant.), which may be used without further purification (e) Phenylmethyl 6-(methyloxy)-3-oxo-3,4-dihydropyrido[2,3-b]pyrazine-1(2H)-carboxylate To a solution of 6-(methyloxy)-1,4-dihydropyrido[2,3-b]pyrazin-3(2H)-one (6.35 g, 35.4 mmol) in EtOAc (600 ml)/NaHCO₃ (sat. solution) (200 ml) stirred vigorously was added at room temperature benzyl chloroformate (5.31 ml, 37.2 mmol). After 45 minutes the reaction was complete. The layers were separated and the organic layer was dried over MgSO₄, filtered and evaporated to afford the desired product as an off-white solid (11 g, 99%).

[ES MS] m/z 314 (MH⁺).

(f) Phenylmethyl 6-(methyloxy)-4-[(2R)-2-oxiranylmethyl]-3-oxo-3,4-dihydropyrido[2,3-b]pyrazine-1 (2H)-carboxylate Phenylmethyl 6-(methyloxy)-3-oxo-3,4-dihydropyrido[2,3-b]pyrazine-1(2H)-carboxylate (11 g, 35.1 mmol) was dissolved in DMF (300 ml) at room temperature under argon to give a yellow solution. The solution was then cooled with an ice bath and treated with sodium hydride (1.685 g, 42.1 mmol). The solution was allowed to warm to room temperature. After 20 minutes (2S)-2-oxiranylmethyl 3-nitrobenzenesulfonate (9.56 g, 36.9 mmol) was added. After 1 h all the starting material was consumed so the reaction was treated with a saturated solution of NaHCO$_3$ (350 ml) and the aqueous layer was extracted with DCM (3×400 ml). The combined organic layers were dried over MgSO$_4$, filtered and evaporated to afford a light brown oil (16.93 g). The product was used as crude in the next step.
[ES MS] m/z 370 (MH$^+$).

(g) Phenylmethyl (1S)-1-(hydroxymethyl)-3,8-dioxo-1,2,3,4-tetrahydro-5H 8H-2a,5,8a-triazaacenaphthylene-5-carboxylate Phenylmethyl 6-(methyloxy)-4-[(2R)-2-oxiranylmethyl]-3-oxo-3,4-dihydropyrido[2,3-b]pyrazine-1(2H)-carboxylate (crude, 15.93 g, estimated 32.8 mmol) was dissolved in DMF (250 ml) at room temperature and heated at 130° C. for 2 nights and at 120° C. for one night. The reaction was complete so DMF was evaporated and the residue treated with water/brine (350/50 ml) and DCM (500 ml). The layers were separated and the aqueous layer was extracted once more with DCM (500 ml). The combined organic extracts were dried over MgSO$_4$, filtered and evaporated to afford a brown oil which was dried under high vacuum over the weekend. The crude product was purified by silica chromatography using a 0-10% MeOH/DCM gradient to afford the desired product as a golden foam (3.6 g, 30.9%).
[ES MS] m/z 356 (MH$^+$).

(h) (1S)-1-(Hydroxymethyl)-1,2-dihydro-3H,8H-2a, 5,8a-triazaacenaphthylene-3,8-dione Phenylmethyl (1S)-1-(hydroxymethyl)-3,8-dioxo-1,2,3,4-tetrahydro-5H,8H-2a,5,8a-triazaacenaphthylene-5-carboxylate (1.6 g, 4.50 mmol) was dissolved in ethanol (100 ml) at room temperature and then treated with palladium on carbon (10% paste) (1 g, 0.940 mmol). Everything was stirred at room temperature under 1 atmosphere of hydrogen for 3 h. The reaction was then filtered through a Celite pad and the impurities washed with more ethanol. The product was then eluted with DMF (400 ml) and the DMF evaporated to afford a brown solid (780 mg). The solid was then suspended in 30% MeOH/DCM (150 ml) and stirred with manganese dioxide (1.174 g, 13.51 mmol) at room temperature for 5 h and then filtered through a pad of Celite which was washed with 20% MeOH/DCM (100 ml). The solvents were evaporated to afford the desired compound as a brown solid (750 mg, 76%).
[ES MS] m/z 220 (MH$^+$).

(i) [(1S)-3,8-Dioxo-1,2-dihydro-3H,8H-2a,5,8a-triazaacenaphthylen-1-yl]methyl methanesulfonate (1S)-1-(Hydroxymethyl)-1,2-dihydro-3H,8H-2a,5,8a-triazaacenaphthylene-3,8-dione (750 mg, 3.42 mmol) was suspended in dry DCM (100 ml) at room temperature under argon and then treated with Et$_3$N (0.572 ml, 4.11 mmol). The mixture was then cooled using an ice-water bath. Methanesulfonyl chloride (0.293 ml, 3.76 mmol) was then added and the reaction was allowed to warm up to room temperature. After 50 minutes there was no starting material left so the mixture was washed with saturated NaHCO$_3$ (100 ml). The aqueous layer was extracted with 20% MeOH/DCM (2×100 ml); the combined organic extracts were dried over MgSO$_4$, filtered and evaporated to afford the product as a brown foam (1.05 g, 90% purity by LCMS).
[ES MS] m/z 297.9 (MH$^+$).

(j) 1,1-Dimethylethyl (1-{[(1R)-3,8-dioxo-1,2-dihydro-3H,8H-2a,5,8a-triazaacenaphthylen-1-yl]methyl}-4-piperidinyl)carbamate A solution of [(1S)-3,8-dioxo-1,2-dihydro-3H,8H-2a,5,8a-triazaacenaphthylen-1-yl]methyl methanesulfonate (1.05 g, 3.53 mmol) in dry CH$_3$CN (50 ml) at room temperature under argon was treated with pyridine (0.343 ml, 4.24 mmol), followed by 1,1-dimethylethyl 4-piperidinylcarbamate (0.884 g, 4.24 mmol). The mixture was heated at 70° C. for 1.5 h and then at 90° C. for 3 h. LCMS showed ~25% of product. So 0.5 eq of pyridine and 0.5 eq of 1,1-dimethylethyl 4-piperidinylcarbamate were added and the reaction was heated at 90° C. overnight and then stirred at room temperature for 2 days. The reaction was complete. The solvent was evaporated and the residue partitioned between sat NaHCO$_3$ and 20% MeOH/DCM (100 ml/100 ml). The layers were separated and the aqueous layer was extracted with 20% MeOH/DCM again (2×100 ml). The combined organic extracts were dried over MgSO$_4$, filtered and evaporated to afford 1.7 g of crude which was purified by silica chromatography using a 0-5% MeOH/DCM gradient to afford the product as a yellow solid (0.57 g, 40.2%).
[ES MS] m/z 402 (MH$^+$).

(k) (1R)-1-[(4-Amino-1-piperidinyl)methyl]-1,2-dihydro-3H,8H-2a,5,8a-triazaacenaphthylene-3,8-dione A solution of 1,1-dimethylethyl (1-{[(1R)-3,8-dioxo-1,2-dihydro-3H,8H-2a,5,8a-triazaacenaphthylen-1-yl]methyl}-4-piperidinyl)carbamate (0.57 g, 1.420 mmol) in chloroform (7 ml) at room temperature was treated with 4M HCl in 1,4-dioxane (7 ml). A solid precipitated out and the mixture was stirred at room temperature. After 0.5 h some MeOH was added to dissolve most of the solid, followed by toluene and all the solvents were removed to afford the product as a yellow solid.

The crude dihydrochloride was dissolved in MeOH (4 ml) plus water (1 ml) and applied to an SCX column (10 g) (preconditioned with 2 column volumes of MeOH). The column was then eluted, under gravity, using (i) MeOH (2×50 ml), (ii) 0.5M ammonia in MeOH (3×50 ml fractions). Appropriate fractions were combined and evaporated under reduced pressure to give 385 mg (90%) of the title compound.
[ES MS] m/z 302 (MH$^+$).

(l) Title compound: (1R)-1-{[4-({[6-(Trifluoromethyl)-3-pyridinyl]methyl}amino)-1-piperidinyl] methyl}-1,2-dihydro-3H 8H-2a,5,8a-triazaacenaphthylene-3,8-dione A solution of (1R)-1-[(4-amino-1-piperidinyl)methyl]-1,2-dihydro-3H,8H-2a,5,8a-triazaacenaphthylene-3,8-dione (10.7 mg, 0.036 mmol) and 6-(trifluoromethyl)-3-pyridinecarbaldehyde (6.22 mg, 0.036 mmol) in a mixture of DCM (0.5 ml) and MeOH (0.5 ml) was stirred at room temperature overnight. NaBH(OAc)$_3$ (22.58 mg, 0.107 mmol) was then added. The resulting mixture was stirred at room temperature and more NaBH(OAc)$_3$ was added in several portions until starting material was not detected by LCMS. The reaction was quenched with 10% NaHCO$_3$ and extracted with DCM. The organic layer was dried (MgSO$_4$), filtered, and concentrated.

The crude of reaction was purified by flash chromatography using manual Flashmaster II, a 500 mg silica gel cartridge, and mixtures of DCM and MeOH as eluent. The obtained solid was triturated with hexane and filtered under vacuum to give 4 mg (8.69 µmol, 24.47%) of (1R)-1-{[4-({[6-(trifluoromethyl)-3-pyridinyl]methyl}amino)-1-piperidinyl]methyl}-1,2-dihydro-3H,8H-2a,5,8a-triazaacenaphthylene-3,8-dione as a brown solid.

$^1$H-NMR (δ, ppm, CDCl$_3$): 8.67 (s, 1H), 7.93-7.84 (m, 2H), 7.77 (d, 1H), 7.66 (d, 1H), 6.35 (d, 1H), 5.09-4.96 (m, 1H), 4.60 (dd, 1H), 4.41 (dd, 1H), 3.90 (s, 2H), 3.13 (dd, 1H), 2.99-2.86 (m, 1H), 2.73 (dd, 1H), 2.69-2.58 (m, 1H), 2.56-2.43 (m, 1H), 2.39-2.19 (m, 2H), 1.93-1.76 (m, 2H), 1.42-1.20 (m, 2H). [ES MS] m/z 461 (MH$^+$).

Example 12

Compound: Synthesis of (1R)-1-[(4-{[(5-bromo-6-methyl-3-pyridinyl)methyl]amino}-1-piperidinyl)methyl]-1,2-dihydro-4H,9H-imidazo[1,2,3-ij]-1,8-naphthyridine-4,9-dione hydrochloride, using Preparative Scheme (3)

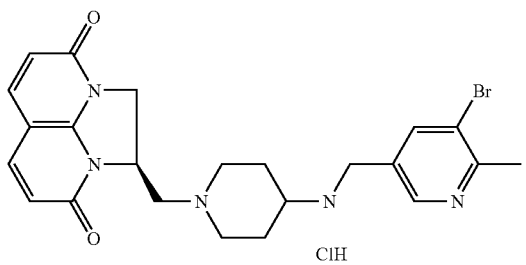

A solution of (1R)-1-[(4-amino-1-piperidinyl)methyl]-1,2-dihydro-4H,9H-imidazo[1,2,3-ij]-1,8-naphthyridine-4,9-dione (for a synthesis see Example 110)) (66.1 mg, 0.220 mmol) and 5-bromo-6-methyl-3-pyridinecarbaldehyde (for a synthesis see Preparation 7 below) (44 mg, 0.172 mmol) in a mixture of DCM (2.0 ml) and MeOH (0.1 ml) was stirred at room temperature overnight. NaBH(OAc)$_3$ (140 mg, 0.661 mmol) was then added and the mixture stirred at room temperature. The reaction was monitored by LCMS and when full conversion was observed, it was quenched with 10% NaHCO$_3$ and extracted with DCM. The organic layer was dried (MgSO$_4$), filtered, and concentrated.

Purification by flash chromatography using Flashmaster II, a 2 g silica gel cartridge, and mixtures of hexane and EtOAc and then DCM and MeOH as eluent afforded 69.5 mg (0.14 mmol, 83%) of the expected product as the free base. It was dissolved in MeOH (3 ml). HCl (3M solution in MeOH, 38 µl, 0.114 mmol) was added dropwise. After stirring at room temperature for 20 min, the solvent was evaporated. (1R)-1-[(4-{[(5-bromo-6-methyl-3-pyridinyl)methyl]amino}-1-piperidinyl)methyl]-1,2-dihydro-4H,9H-imidazo[1,2,3-ij]-1,8-naphthyridine-4,9-dione hydrochloride (47 mg, 0.09 mmol, 80%) was obtained as a pale yellow solid.

$^1$H-NMR (δ, ppm, DMSO-d$_6$): 8.40 (s, 1H), 8.01 (s, 1H), 7.72 (d, 2H), 6.12 (t, 2H), 5.01-4.89 (m, 1H), 4.35-4.19 (m, 2H), 3.80 (bs, 2H), 2.89 (bd, 2H), 2.76 (bt, 1H), 2.54 (s, 3H), 2.52-2.41 (m, 2H), 2.21-1.98 (m, 2H), 1.78 (bt, 2H), 1.35-1.09 (m, 2H). [ES MS] m/z 484 (MH$^+$).

Example 17

Compound: Synthesis of 2-{[4-({[6-(trifluoromethyl)-3-pyridazinyl]methyl}amino)-1-piperidinyl]methyl}-1,2-dihydro-3H,8H-2a,5,8a-triazaacenaphthylene-3,8-dione, using Preparative Scheme (1)

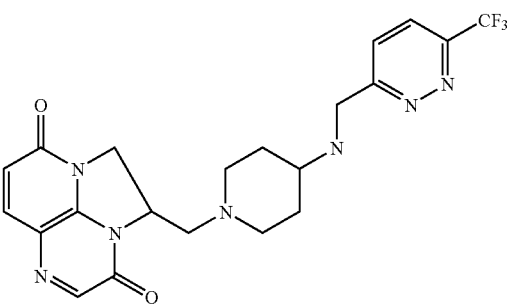

A mixture of 2-[(4-amino-1-piperidinyl)methyl]-1,2-dihydro-3H,8H-2a,5,8a-triazaacenaphthylene-3,8-dione (for a synthesis see Example 2(j)) (56.3 mg, 0.187 mmol), K$_2$CO$_3$ (34.4 mg, 0.249 mmol) and 3-(bromomethyl)-6-(trifluoromethyl)pyridazine (for a synthesis see Preparation 1 below) (30 mg, 0.124 mmol) in CH$_3$CN (1 ml) and MeOH (0.1 ml) was stirred at room temperature overnight. LCMS showed amine derivative remaining. An excess of 3-(bromomethyl)-6-(trifluoromethyl)pyridazine (25 mg) was added. The mixture was stirred at room temperature for 1 h. The solid was filtered off and the solvent evaporated. Purification by flash chromatography using Flashmaster II and mixtures of DCM and MeOH as eluent afforded 2-{[4-({[6-(trifluoromethyl)-3-pyridazinyl]methyl}amino)-1-piperidinyl]methyl}-1,2-dihydro-3H,8H-2a,5,8a-triazaacenaphthylene-3,8-dione (17 mg, 30%).

$^1$H-NMR (δ, ppm, CDCl$_3$): 7.84-7.75 (m, 4H), 6.39 (d, 1H), 5.08-4.99 (m, 1H), 4.56 (dd, 1H), 4.39 (dd, 1H), 4.24 (s, 2H), 3.16 (dd, 1H), 2.97-2.91 (m, 1H), 2.74-2.65 (m, 2H), 2.61-2.51 (m, 1H), 2.39-2.22 (m, 2H), 1.93-1.82 (m, 2H), 1.43-1.33 (m, 2H). [ES MS] m/z 462 (MH+).

Example 51

Compound: Synthesis of (2R)-2-[(4-{[(5-bromo-6-methyl-3-pyridinyl)methyl]amino}-1-piperidinyl)methyl]-1,2-dihydro-3H,8H-2a,5,8a-triazaacenaphthylene-3,8-dione hydrochloride, using Preparative Scheme (1)

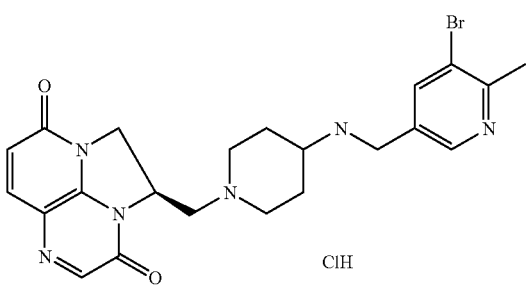

A solution of (2R)-2-[(4-amino-1-piperidinyl)methyl]-1,2-dihydro-3H,8H-2a,5,8a-triazaacenaphthylene-3,8-dione (for a synthesis see Example 2(j)) (187 mg, 0.622 mmol) and 5-bromo-6-methyl-3-pyridinecarbaldehyde (for a synthesis see Preparation 7 below) (97 mg, 0.485 mmol) in a mixture of DCM (10 ml) and MeOH (0.1 ml) was stirred at room temperature overnight. NaBH(OAc)$_3$ (396 mg, 1.867 mmol) was then added and the mixture stirred at room temperature. The reaction was monitored by LCMS and when full conversion was observed, it was quenched with 10% NaHCO$_3$ and extracted with DCM. The organic layer was dried (MgSO$_4$), filtered, and concentrated.

Purification by flash chromatography using Flashmaster II, a 5 g silica gel cartridge, and mixtures of DCM and MeOH as eluent afforded 140 mg (0.288 mmol, 60%) of the expected product as the free base. It was dissolved in MeOH (10 ml). HCl (3M solution in MeOH, 0.071 ml, 0.213 mmol) was added dropwise. After stirring at room temperature for 20 min, the solvent was evaporated. (2R)-2-[(4-{[(5-bromo-6-methyl-3-pyridinyl)methyl]amino}-1-piperidinyl)methyl]-1,2-dihydro-3H,8H-2a,5,8a-triazaacenaphthylene-3,8-dione hydrochloride (95 mg, 0.173 mmol, 81%) was obtained as a pale yellow solid.

$^1$H-NMR (δ, ppm, CD$_3$OD): 8.41 (s, 1H), 8.07 (s, 1H), 7.88 (d, 1H), 7.78 (s, 1H), 6.37 (d, 1H), 5.16-5.10 (m, 1H), 4.45-4.42 (m, 2H), 3.93 (s, 2H), 3.13-3.07 (m, 2H), 2.86 (dd, 1H), 2.78-2.73 (m, 2H), 2.63 (s, 3H), 2.36-2.21 (m, 2H), 2.01-1.91 (m, 2H), 1.47-1.38 (m, 2H). [ES MS] m/z 485 (MH+).

Example 59

Compound: Synthesis of (1R)-1-{[4-({[6-(trifluoromethyl)-3-pyridinyl]methyl}amino)-1-piperidinyl]methyl}-1,2-dihydro-4H,9H-imidazo[1,2,3-ij]-1,8-naphthyridine-4,9-dione hydrochloride, using Preparative Scheme (3)

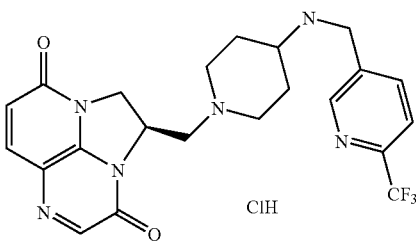

A solution of (1R)-1-[(4-amino-1-piperidinyl)methyl]-1,2-dihydro-4H,9H-imidazo[1,2,3-ij]-1,8-naphthyridine-4,9-dione (for a synthesis see Example 11)) (400 mg, 1.33 mmol) and 6-(trifluoromethyl)-3-pyridinecarbaldehyde (233 mg, 1.33 mmol) in a mixture of DCM (5 ml) and MeOH (5 ml) was stirred at room temperature for 2 h. NaBH(OAc)$_3$ (1.7 g, 7.99 mmol) was then added and the mixture was stirred at room temperature. The reaction was monitored by LCMS. More aldehyde (47 mg, 0.27 mmol), and NaBH(OAc)$_3$ (421 mg, 1.98 mmol) were added and when full conversion was observed, it was quenched with 10% NaHCO$_3$ and extracted with DCM. The organic layer was dried (MgSO$_4$), filtered, and concentrated. Purification by flash chromatography using a 70 g silica gel cartridge, and mixtures of DCM and MeOH as eluent afforded 463 mg (75%) of the expected product as the free base. It was dissolved in MeOH (50 ml). HCl (4M solution in 1,4-dioxane, 0.25 ml, 1 mmol) was added dropwise. After stirring at room temperature for 20 min, the solvent was evaporated. (1R)-1-{[4-({[6-(Trifluoromethyl)-3-pyridinyl]methyl}amino)-1-piperidinyl]methyl}-1,2-dihydro-4H,9H-imidazo[1,2,3-ij]-1,8-naphthyridine-4,9-dione hydrochloride (238 mg, 0.480 mmol, 36%) was obtained as a beige solid.

$^1$H-NMR (δ, ppm, DMSO-d$_6$): 10.21 (bs, 1H), 9.01 (s, 1H), 8.43 (d, 1H), 8.02 (d, 1H), 7.79 (dd, 2H), 6.22 (d, 2H), 5.40 (bs, 1H), 4.50-4.36 (m, 4H), 3.80-3.66 (m, 5H), 3.17 (bs, 2H), 2.17 (bs, 4H). [ES MS] m/z 460 (MH+).

Example 60

Compound: Synthesis of (1R)-1-{[4-({[5-methyl-6-(trifluoromethyl)-3-pyridinyl]methyl}amino)-1-piperidinyl]methyl}-1,2-dihydro-4H,9H-imidazo[1,2,3-ij]-1,8-naphthyridine-4,9-dione A mixture of (1R)-1-[(4-amino-1-piperidinyl)methyl]-1,2-dihydro-4H,9H-imidazo[1,2,3-ij]-1,8-naphthyridine-4,9-dione (Example 1 step (j): 70.5 mg, 0.235 mmol), 5-methyl-6-(trifluoromethyl)-3-pyridinecarbaldehyde (Preparation 12: 37 mg, 0.196 mmol) and magnesium sulphate (anhydrous) (58.9 mg, 0.489 mmol) in DCM (7 ml) was stirred overnight at RT. LCMS on the crude product showed imine and not starting material was present. Rt of the desired compound was 2.59 [M+H] 472.2. Then sodium triacetoxyborohydride (124 mg, 0.587 mmol) was added and the mixture was stirred for 3 hours. LCMS showed imine so 1 eq. sodium triacetoxyborohydride (41.5 mg, 0.196 mmol) was added. Saturated aqueous sodium bicarbonate solution was added to the organic phase until pH9 was achieved. The organic phase was extracted with DCM and isolated, dried over anhydrous sodium sulphate, filtered and concentrated under reduced pressure. The residue was purified by Flash-Master chromatography on a 2 g silica gel cartridge using DCM/MeOH 5% to obtain three batches (9.3 mg). $^1$H NMR was consistent with the desired compound, and LCMS was consistent with the desired compound [M+H]+ 474, Rt=1.81 purity 95%.

Example 71

Compound: Synthesis of (2-chloro-4-{[(1-{[(1R)-4,9-dioxo-1,2-dihydro-4H,9H-imidazo[1,2,3-ij]-1,8-naphthyridin-1-yl]methyl}-4-piperidinyl)amino]methyl}phenyl)methyl acetate (last step)

This example illustrates the use of a compound of Formula (IIB) in which W is a bromomethyl moiety.

(1R)-1-[(4-amino-1-piperidinyl)methyl]-1,2-dihydro-4H,9H-imidazo[1,2,3-ij]-1,8-naphthyridine-4,9-dione (Example 1 step 11): 34 mg, 0.113 mmol) was dissolved in Acetonitrile (5 mL) and [4-(bromomethyl)-2-chlorophenyl]methyl acetate (34.6 mg, 0.125 mmol), potassium carbonate (31.3 mg, 0.226 mmol) and sodium iodide (0.848 mg, 5.66 µmol) was added leaving the reaction at room temperature overnight. Next morning LCMS showed completion and solvent was removed under vacuum. Resulting crude was dissolved in DCM and washed several times with water. Organic layers were dried over sodium sulphate, filtered and volatiles removed under vacuum. Purification was carried out by flash master II, Si II 2 g, DCM-MeOH (0-20%) to obtain 10 mg of the final compound as a yellow solid.

Example 75

Compound: Synthesis of (2R)-2-{[4-({[5-methyl-6-(trifluoromethyl)-3-pyridinyl]methyl}amino)-1-piperidinyl]methyl}-1,2-dihydro-3H,8H-2a,5,8a-triazaacenaphthylene-3,8-dione hydrochloride To a solution of (2R)-2-{[4-({[5-methyl-6-(trifluoromethyl)-3-pyridinyl]methyl}amino)-1-piperidinyl]methyl}-1,2-dihydro-3H,8H-2a,5,8a-triazaacenaphthylene-3,8-dione (Example 60 compound: 80 mg, 0.169 mmol) in DCM (2 mL) at 0° C., HCl (4M in 1,4-dioxane) (0.042 mL, 0.169 mmol) was added. The reaction mixture was stirred at room temperature for 40 min. Then the solvent was evaporated under vacuum and the crude was dispersed in hexane/DCM. The precipitated solid was isolated by filtration under vacuum and washed with DCM and hexane to obtain 42 mg of beige solid. $^1$H NMR were consistent with the desired product. LCMS was consistent with the desired product [M+H]+ 475, Rt=2.58 purity 95%.

In Table 1 the source of the compound of Formula IIB used in the preparation of the Example compounds is indicated. Where these are not known compounds their preparation is described below. The other Example compounds listed above were prepared using an analogous procedure with minor modifications and were isolated either as the parent compound or as the hydrochloride.

Preparation of various compounds of Formula IIB used in the preparation of the listed Examples is set out below.

Preparation 1

3-(Bromomethyl)-6-(trifluoromethyl)pyridazine
(Used to prepare Examples 17 and 18)

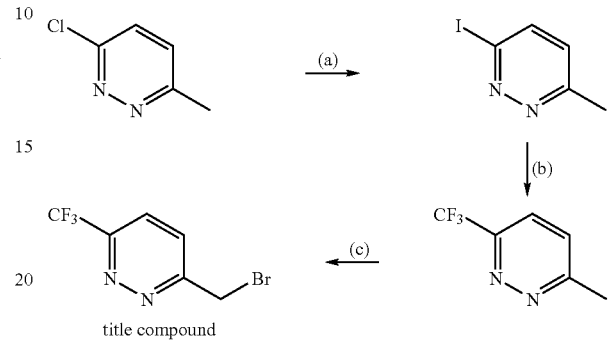

(a) 3-Iodo-6-methylpyridazine

To a solution of 3-chloro-6-methylpyridazine (500 mg) in HI (3 ml) was added NaI (782 mg). The reaction was heated at 40° C. for 4 h and at 70° C. overnight. The yellow precipitate was filtered. The mother liquors were basified using solid NaOH, extracted with DCM, dried over MgSO$_4$, filtered, concentrated, and purified by chromatography on silica gel using EtOAc/hexane as eluent to give 171.7 mg (20%) of the title compound as a white solid almost pure by HPLC. The yellow precipitate was basified using the same aqueous phase, extracted with DCM, dried over MgSO$_4$, filtered and concentrated, to give 579.1 mg (68%) of the pure title compound as a white solid.
$^1$H-NMR (δ, ppm, CDCl$_3$): 7.74 (1H, d), 7.02 (1H, d), 2.66 (3H, s). [ES MS] m/z 221 (MH$^+$).

(b) 3-Methyl-6-(trifluoromethyl)pyridazine

A mixture of CuI (263 mg) and KF (80 mg) was heated under vacuum for 30 minutes until a greenish colour was observed. The system was filled with N$_2$ and a solution of 3-iodo-6-methylpyridazine (300 mg) in DMF (1.25 ml) and N-methylpyrrolidinone (1.25 ml) followed by trimethyl(trifluoromethyl)silane (185 µl) were subsequently added. A dark brown colour was observed. After stirring at room temperature for 5 days, the reaction was not complete. CuI (263 mg), KF (80 mg), and CF$_3$TMS (185 µl) were added and stirring was continued overnight. Additional CuI (135 mg), KF (40 mg), and CF$_3$TMS (90 µl) were added and after one more day at room temperature, almost no starting material was observed. Aqueous ammonia and TBME were added and the phases were separated. The aqueous one was washed with TBME. The organic extracts were combined and subsequently washed with aqueous ammonia, 1M HCl, saturated NaHCO$_3$, and brine, dried over Na$_2$SO$_4$, filtered and concentrated to give 70 mg (35%) of the title compound.
$^1$H-NMR (δ, ppm, CDCl$_3$): 7.72 (1H, d), 7.53 (1H, d), 2.85 (3H, s). [ES MS] m/z 163 (MH$^+$).

(c) Title compound:
3-(Bromomethyl)-6-(trifluoromethyl)pyridazine

A mixture of 3-methyl-6-(trifluoromethyl)pyridazine (70 mg), N-bromosuccinimide (84 mg), azobisisobutyronitrile (14.1 mg), and CCl$_4$ (3 ml) was heated under reflux for 2 days. The solvent was evaporated to dryness under vacuum. The residue obtained was purified by chromatography column on silica gel (AIT, Flashsmart BP-SUP, 20-40 μm) using a mixture of EtOAc/hexane as eluent to give 14 mg (14%) of the title compound along with 15.3 mg (11%) of the dibrominated derivative.

$^1$H-NMR (δ, ppm, CDCl$_3$): 7.90 (1H, d), 7.86 (1H, d), 4.83 (2H, s). [ES MS] m/z 241 and 243 (MH$^+$).

Preparation 2

5,6-Dichloro-3-pyridinecarbaldehyde (Used to prepare Example 15)

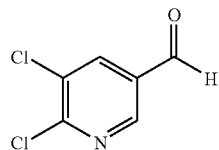

To a solution of (5,6-dichloro-3-pyridinyl)methanol (200 mg) in DCM, molecular sieves (3 Å) (55 mg) and 4-methyl-morpholine-N-oxide (198 mg) was added and stirred at room temperature for 10 minutes. Then tetra-n-propylammonium perruthenate (VII) (38 mg) was added and stirred overnight. The reaction mixture was filtered and the solvent was evaporated to dryness under vacuum. The residue obtained was purified by chromatography column on silica gel using a mixture of EtOAc/hexane as eluent to give 44 mg (22%) of the title compound.

$^1$H-NMR (δ, ppm, CDCl$_3$): 10.09 (s, 1H), 8.77 (s, 1H), 8.25 (s, 1H).

Preparation 3

5-Formyl-3-methyl-2-pyridinecarbonitrile (Used to prepare Example 32)

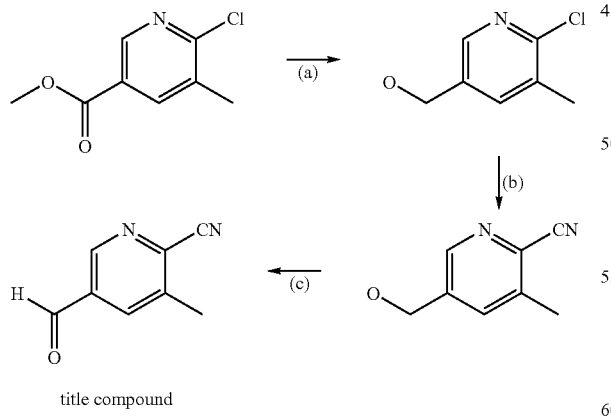

title compound (a) (6-Chloro-5-methyl-3-pyridinyl)methanol

To a solution of methyl 6-chloro-5-methyl-3-pyridinecarboxylate (84 mg, 0.453 mmol) in DCM (2 ml), DIBAL-H (1.5 M solution in toluene, 0.905 ml, 1.358 mmol) was added dropwise under N$_2$ at −78° C. The reaction mixture was allowed to attain rt and stirred overnight. After 18 h, TLC showed no starting material. The reaction was quenched by addition of sodium-potassium tartrate saturated solution, extracted with DCM, dried, filtered, and concentrated to afford (6-chloro-5-methyl-3-pyridinyl)methanol (63 mg, 0.400 mmol, 88% yield) pure enough to be used in the next step.

$^1$H-NMR (δ ppm, CDCl$_3$): 8.17 (s, 1H), 7.60 (s, 1H), 4.69 (s, 2H), 2.37 (s, 3H).

(b) 5-(Hydroxymethyl)-3-methyl-2-pyridinecarbonitrile

CuCN (54.3 mg, 0.607 mmol) was added to a solution of (6-chloro-5-methyl-3-pyridinyl)methanol (47.8 mg, 0.303 mmol) in anhydrous DMF (2 ml) and the mixture was stirred under microwave irradiation at 250° C. for 35 min. Full conversion was observed by HPLC. TBME and 28% NH$_3$ were added. Extraction, drying (MgSO$_4$), filtration, and removal of the solvent afforded 5-(hydroxymethyl)-3-methyl-2-pyridinecarbonitrile (28.2 mg, 0.190 mmol, 62.8% yield) pure enough to be used in the next step.

$^1$H-NMR (δ, ppm, CDCl$_3$): 8.50 (s, 1H), 7.72 (s, 1H), 4.81 (s, 2H), 2.57 (s, 3H).

(c) Title compound:
5-Formyl-3-methyl-2-pyridinecarbonitrile

MnO$_2$ (165 mg, 1.903 mmol) was added to a solution of 5-(hydroxymethyl)-3-methyl-2-pyridinecarbonitrile (28.2 mg, 0.190 mmol) in DCM (2 ml) at rt and the mixture was stirred at that temperature overnight. LCMS showed the starting material was gone. The solids were filtered off and the solvent evaporated. 5-Formyl-3-methyl-2-pyridinecarbonitrile (20.2 mg) was obtained impure. It was used in the next step without prior purification.

$^1$H-NMR (δ ppm, CDCl$_3$): 10.18 (s, 1H), 8.99 (s, 1H), 8.14 (s, 1H), 2.68 (s, 3H).

Preparation 4

3-Chloro-5-Formyl-2-pyridinecarbonitrile (Used to prepare Example 49)

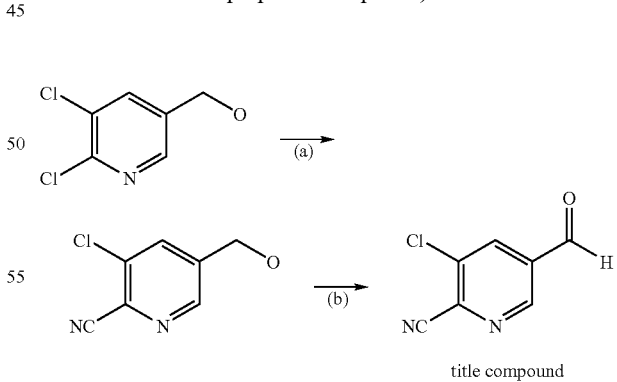

title compound (a)
3-Chloro-5-(hydroxymethyl)-2-pyridinecarbonitrile

Zn(CN)$_2$ (64.3 mg, 0.548 mmol) and Pd(PPh$_3$)$_4$ (84 mg, 0.073 mmol) were added to a solution of 5,6-dichloro-3-pyridinemethanol (130 mg, 0.730 mmol) in anhydrous DMF (1.5 ml) under $N_2$ and the mixture was heated at 95° C. overnight. Low conversion was observed by HPLC. After heating under reflux for 2 h, the conversion did not increase, so additional $Pd(PPh_3)_4$ (84 mg, 0.073 mmol) was added. Two more h under reflux gave full conversion. TBME, and 10% $Na_2CO_3$ were added. Extraction, drying ($MgSO_4$), filtration, and removal of the solvent afforded the crude product. Purification by flash chromatography using Flashmaster II, a 5 g spherical silica gel cartridge, and mixtures of hexane and EtOAc as an eluent afforded 3-chloro-5-(hydroxymethyl)-2-pyridinecarbonitrile (34.6 mg, 0.205 mmol, 28% yield) as a pale yellow solid.

1H-NMR ($\delta$, ppm, $CDCl_3$): 8.57 (s, 1H), 7.94 (s, 1H), 4.87 (s, 2H). [ES MS] m/z 169 ($MH^+$).

(b) Title compound:
3-Chloro-5-Formyl-2-pyridinecarbonitrile $CrO_2$ (Magtrieve) (335 mg, 3.99 mmol) was added to a solution of 3-chloro-5-(hydroxymethyl)-2-pyridinecarbonitrile (33.6 mg, 0.199 mmol) in DCM (2.5 ml) and the mixture was stirred at 40° C. TLC (5% MeOH in DCM) after 3 h showed some starting material. It was heated at 40° C. overnight and full conversion was observed by TLC. The solids were filtered off and the solvent evaporated, yielding 3-chloro-5-formyl-2-pyridinecarbonitrile (19.7 mg, 0.118 mmol, 59% yield) as a white solid.

$^1$H-NMR ($\delta$, ppm, $CDCl_3$): 10.19 (s, 1H), 9.06 (s, 1H), 8.32 (s, 1H).

Preparation 5

5-Fluoro-6-methyl-3-pyridinecarbaldehyde (Used to prepare Example 52)

(a) (2,6-Dichloro-5-fluoro-3-pyridinyl)methanol

To a solution of methyl 2,6-dichloro-5-fluoro-3-pyridinecarboxylate (3 g, 13.39 mmol) in DCM (12 ml) at 0° C. under $N_2$ was added dropwise DIBAL-H (1.5 M solution in toluene, 19.20 ml, 28.8 mmol). The reaction mixture was stirred at 0° C. for 20 h. TLC (DCM) showed starting material remaining. Then, more DIBAL-H (1.5 M solution in toluene, 10 ml) was added. The reaction was stirred at 0° C. for 20 h. The reaction mixture was diluted with MeOH and concentrated under reduced pressure. The residue was treated with 1N HCl solution and extracted 3 times with EtOAc. The combined organic phases were washed with sat. NaCl, dried over $Na_2SO_4$ and concentrated to give 1.5 g (53%) of the title compound.

$^1$H-NMR ($\delta$, ppm, $CDCl_3$): 7.77 (d, 1H), 4.77 (bs, 2H).

(b) (6-Chloro-5-fluoro-3-pyridinyl)methanol

To a solution of (2,6-dichloro-5-fluoro-3-pyridinyl)methanol (4.4 g, 22.45 mmol) in 1,4-dioxane (20 ml) was added $Et_3N$ (3.42 ml, 24.69 mmol), formic acid (0.947 ml, 24.69 mmol) and $Pd(PPh_3)_4$ (1.297 g, 1.122 mmol). The mixture was then heated at 110° C. for 6 h in a pressure tube. The crude was diluted with $H_2O$ and extracted twice with EtOAc. The combined organic phases were washed with $H_2O$ and sat. NaCl, dried over $Na_2SO_4$ and concentrated under reduced pressure. The crude was purified by flash chromatography using Flashmaster II, a 70 g spherical silica gel cartridge and DCM/MeOH 98:2 as eluent to give 2.0 g (41%) of the title compound pure enough to be used in the next step.

$^1$H-NMR ($\delta$, ppm, $CDCl_3$): 8.18 (d, 1H), 7.70 (dd, 1H), 4.78 (bs, 2H), 1.93 (bs, 1H). [ES MS] m/z 162 ($MH^+$).

(c) (5-Fluoro-6-methyl-3-pyridinyl)methanol

To a solution of (6-chloro-5-fluoro-3-pyridinyl)methanol (1.3 g, 8.05 mmol) in 1,4-dioxane (10 ml) was added $K_2CO_3$ (3.34 g, 24.14 mmol), trimethylboroxin (1.125 ml, 8.05 mmol) and $Pd(PPh_3)_4$ (0.465 g, 0.402 mmol). The mixture was then heated at 110° C. for 20 h in a pressure tube. The resulting mixture was quenched with $H_2O$, extracted with EtOAc, dried over $MgSO_4$ and concentrated under vacuum. The residue was purified by flash chromatography using Flashmaster II, a 25 g spherical silica gel cartridge and DCM/MeOH 98:2 as eluent to give 560 mg of the title compound along with $Ph_3PO$. This was washed again with water and extracted with EtOAc to remove $Ph_3PO$. The organic layer

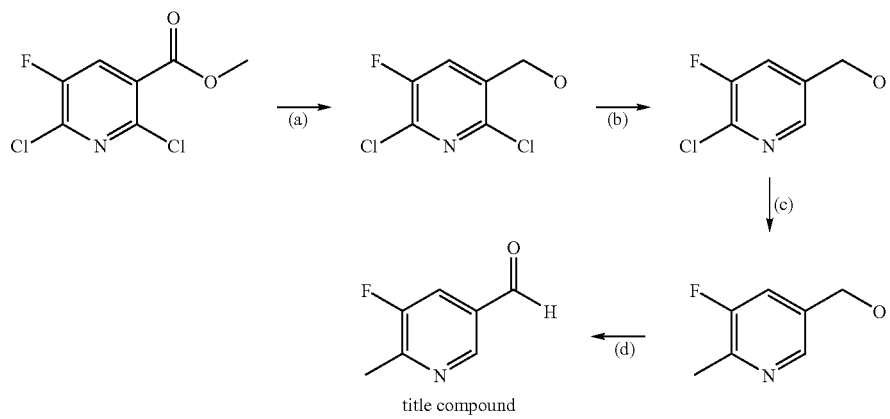

was dried over $MgSO_4$, filtered and concentrated under vacuum to give 468 mg (39%) of the title compound pure enough to be used in the next step.

$^1$H-NMR ($\delta$, ppm, $CDCl_3$): 8.27 (d, 1H), 7.55 (dd, 1H), 4.74 (bs, 2H), 2.49 (s, 3H). [ES MS] m/z 142 ($MH^+$).

(d) Title compound:
5-Fluoro-6-methyl-3-pyridinecarbaldehyde

To a solution of (5-fluoro-6-methyl-3-pyridinyl)methanol (468 mg, 3.32 mmol) in DCM (4 ml) was added $CrO_2$ (Magtrieve) (4.2 g, 49.7 mmol). The mixture was stirred at 35° C. for 4 h. TLC (5% MeOH in DCM) showed starting material remaining. An excess of CrO₂ (Magtrieve) (2.8 g, 33.3 mmol) was added. The mixture was stirred at 35° C. for 48 h. The solids were filtered off and the solvent evaporated to afford 144 mg (28%) of the title compound.

¹H-NMR (δ, ppm, CDCl₃): 10.32 (s, 1H), 8.57 (d, 1H), 7.81 (dd, 1H), 2.87 (s, 3H). [ES MS] m/z 140 (MH⁺).

Preparation 6

6-Ethyl-5-fluoro-3-pyridinecarbaldehyde (used to prepare Example 54)

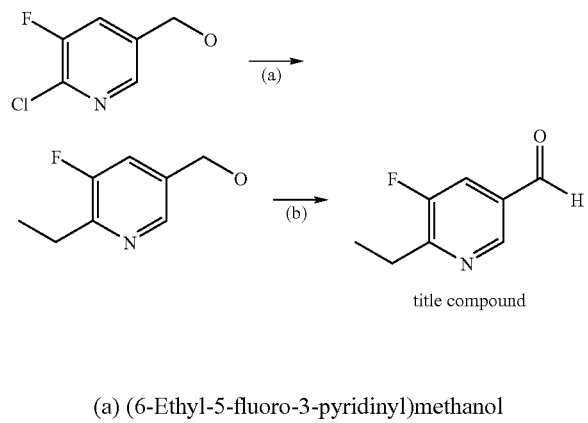

(a) (6-Ethyl-5-fluoro-3-pyridinyl)methanol

To a solution of (6-chloro-5-fluoro-3-pyridinyl)methanol (300 mg, 1.857 mmol) (see Preparation 5(b) above), K₂CO₃ (770 mg, 5.57 mmol), and [1,1'-Bis(diphenylphosphino) ferrocene]dichloro-palladium(II) (136 mg, 0.186 mmol) in THF (6 ml), was added diethylzinc (3.71 ml, 3.71 mmol). The mixture was stirred under reflux for 6 h in a pressure tube. The resulting mixture was quenched with saturated NH₄Cl solution and extracted with EtOAc. The combined organic layers were washed with brine, dried over MgSO₄, and concentrated under reduced pressure. The residue was purified by flash chromatography using Flashmaster II, a 10 g spherical silica gel cartridge BP-SUP 20-40μ, and DCM/MeOH 98:2 mixture as eluent to give 116 mg of desired compound as a yellow solid.

¹H-NMR (δ, ppm, CDCl₃): 8.30 (s, 1H), 7.54 (d, 1H), 4.77 (s, 2H), 2.76 (q, 2H), 2.12 (bs, 1H), 1.28 (t, 3H). [ES MS] m/z 156 (MH⁺).

(b) Title compound:
6-Ethyl-5-fluoro-3-pyridinecarbaldehyde

CrO₂ (Magtrieve) (796 mg, 9.48 mmol) was added to a solution of (6-ethyl-5-fluoro-3-pyridinyl)methanol (98 mg, 0.632 mmol) in DCM (5 ml) and the mixture was stirred at 40° C. for 6 h. TLC (10% DCM/MeOH) showed starting material remaining. An excess of CrO₂ (Magtrieve) (530 mg, 6.32 mmol) was added. After stirring for 12 h, TLC showed the reaction had been completed. The resulting suspension was filtered and washed with DCM. The filtrate was concentrated under reduced pressure to give 57.4 mg of the title compound as a colourless oil.

¹H-NMR (δ, ppm, CDCl₃): 10.35 (s, 1H), 8.60 (d, 1H), 7.82 (dd, 1H), 3.21 (q, 2H), 1.35 (t, 3H). [ES MS] m/z 154 (MH⁺).

Preparation 7

5-Bromo-6-methyl-3-pyridinecarbaldehyde (used to prepare Examples 12, 51 and 55)

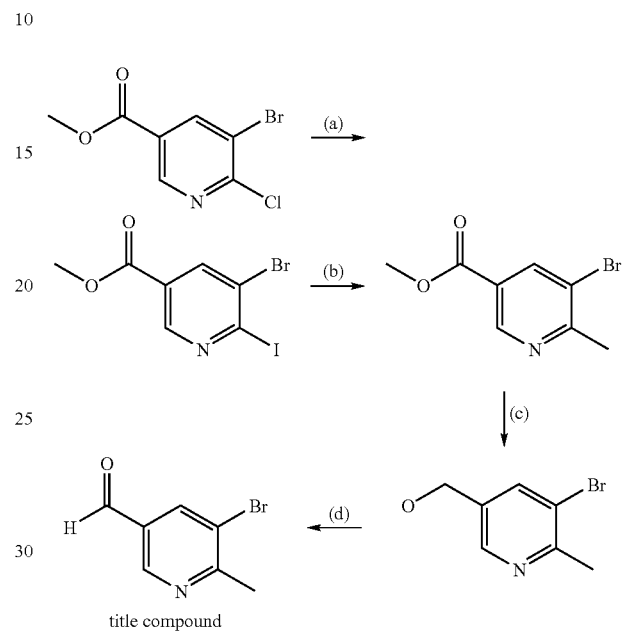

(a) Methyl 5-bromo-6-iodo-3-pyridinecarboxylate

To a mixture of methyl 5-bromo-6-chloro-3-pyridinecarboxylate (1 g, 3.99 mmol) in propionitrile (30 ml) was added iodotrimethylsilane (0.689 ml, 3.99 mmol) and then sodium iodide (1.795 g, 11.98 mmol). The mixture was stirred at room temperature for 30 min. Solvent was evaporated and the obtained solid was dissolved in H₂O. pH was adjusted to basic with 2M NaOH and DCM was added. The organic phase was extracted, dried over Na₂SO₄, filtered and concentrated to give 1.2 g (79%) of desired compound as a yellow solid.

¹H-NMR (δ, ppm, CDCl₃): 8.84 (s, 1H), 8.35 (s, 1H), 3.96 (s, 3H).

(b) Methyl 5-bromo-6-methyl-3-pyridinecarboxylate

Method A
To a mixture of methyl 5-bromo-6-iodo-3-pyridinecarboxylate (232 mg, 0.679 mmol), tetrakis(triphenylphosphine)palladium (0) (39.2 mg, 0.034 mmol), and K₂CO₃ (281 mg, 2.036 mmol) in dioxane (5 ml), trimethylboroxin (0.095 ml, 0.679 mmol) was added under N₂. The reaction mixture was heated at 110° C. and more tetrakis(triphenylphosphine) palladium (0) was added in several portions until starting material was not detected by HPLC. The reaction mixture was diluted with water and extracted three times with EtOAc. The combined organic phases were washed with brine, dried over anhydrous Na₂SO₄ and concentrated under reduced pressure. The crude of reaction was purified by flash chromatography using Flashmaster II, a 5 g silica gel cartridge, and mixtures of hexane and EtOAc to afford the title compound (75 mg, 48%) as a yellow solid.

¹H-NMR (δ, ppm, CDCl₃): 9.01 (s, 1H), 8.41 (s, 1H), 3.95 (s, 3H), 2.74 (s, 3H). [ES MS] m/z 230 (MH⁺).

Method B

To a mixture of methyl 5-bromo-6-chloro-3-pyridinecarboxylate (400 mg, 1.597 mmol), tetrakis(triphenylphosphine)palladium (0) (185 mg, 0.160 mmol), and K₂CO₃ (331 mg, 2.395 mmol) in dioxane (5 ml), trimethylboroxin (0.446 ml, 3.19 mmol) was added under argon. The reaction mixture was heated at 110° C. for 5 h. The reaction mixture was allowed to cool down, filtered through a pad of silica, and concentrated to give 176 mg of the crude material. Purification by flash chromatography using Flashmaster II, a 5 g spherical silica gel cartridge, and mixtures of hexane and DCM as eluent afforded 76 mg of desired compound and 84 mg of methyl 6-chloro-5-methyl-3-pyridinecarboxylate as by-product.

[ES MS] m/z 230 (MH⁺).

(c) (5-Bromo-6-methyl-3-pyridinyl)methanol

To a solution of methyl 5-bromo-6-methyl-3-pyridinecarboxylate (76 mg, 0.330 mmol) in DCM (1.5 ml), DIBAL-H (1.5 M solution in toluene, 0.661 ml, 0.991 mmol) was added dropwise at −78° C. under N₂. The reaction mixture was allowed to warm to rt and stirred overnight. To this solution was added saturated, aqueous NaK-tartrate solution followed by DCM. The organic phase was separated, dried and concentrated to afford 56 mg of (5-bromo-6-methyl-3-pyridinyl)methanol (56 mg, 84%) pure enough to be used in the next step.

¹H-NMR (δ, ppm, CDCl₃): 8.45 (s, 1H), 7.97 (s, 1H), 4.73 (s, 2H), 2.70 (s, 3H).

(d) Title compound: 5-Bromo-6-methyl-3-pyridinecarbaldehyde

To a solution of (5-bromo-6-methyl-3-pyridinyl)methanol (56 mg, 0.277 mmol) in DCM (2 ml), MnO₂ (193 mg, 2.217 mmol) was added. After stirring overnight, an excess of MnO₂ (120 mg, 1.386 mmol) was added and then the mixture was stirred for 3 h more. The reaction mixture was filtrated and evaporated to afford 30 mg of title compound pure enough to be used in the next step.

¹H-NMR (δ, ppm, CDCl₃): 10.05 (s, 1H), 8.87 (s, 1H), 8.25 (s, 1H), 2.75 (s, 3H).

Preparation 8

5-Chloro-6-(hydroxymethyl)-3-pyridinecarbaldehyde
(Used to prepare Example 56)

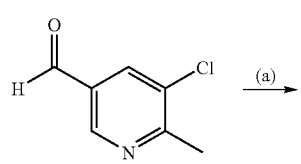

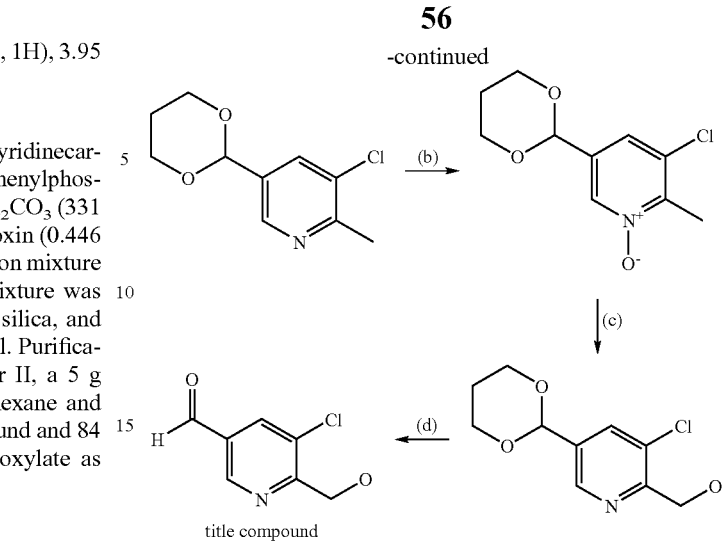

(a) 3-Chloro-5-(1,3-dioxolan-2-yl)-2-methylpyridine p-Toluenesulfonic acid (5.53 mg, 0.032 mmol) was added to a mixture of 5-chloro-6-methyl-3-pyridinecarbaldehyde (for a synthesis see WO20006/137485 A1 Example 256) (250 mg, 1.607 mmol), ethylene glycol (179 μl, 3.21 mmol), and toluene (8 ml) and the mixture was heated under reflux as water was azeotropically removed (Dean-Stark). The progression was monitored by TLC (50% hexane:EtOAc) and HPLC. More ethylene glycol (180 μl) and TsOH (3 mg) were added and after 46 hr full conversion was observed by HPLC. 10% Na₂CO₃ and EtOAc were added. Extraction, drying (MgSO₄), and filtration afforded 3-chloro-5-(1,3-dioxolan-2-yl)-2-methylpyridine (274.3 mg, 86%) pure enough to be used in the next step.

¹H-NMR (δ, ppm, CDCl₃): 8.46 (s, 1H), 7.76 (s, 1H), 5.83 (s, 1H), 4.16-4.02 (s, 4H), 2.65 (s, 3H). [ES MS] m/z 200 (MH⁺).

(b) 3-Chloro-5-(1,3-dioxolan-2-yl)-2-methylpyridine 1-oxide m-CPBA (626 mg, 2.72 mmol) was added to a suspension of 3-chloro-5-(1,3-dioxolan-2-yl)-2-methylpyridine (271.4 mg, 1.359 mmol) and NaHCO₃ (343 mg, 4.08 mmol) in DCM (3 ml) and stirred at room temperature. After 21 h, HPLC showed full conversion. DCM and 1M NaOH were added. It was extracted, dried (MgSO₄), filtered, and concentrated yielding 3-chloro-5-(1,3-dioxolan-2-yl)-2-methylpyridine 1-oxide (228 mg, 78%) as a pale yellow oil pure enough to be used in the next step.

¹H-NMR (δ, ppm, CDCl₃): 8.33 (s, 1H), 7.38 (s, 1H), 5.80 (s, 1H), 4.05 (s, 4H), 2.64 (s, 3H). [ES MS] m/z 216 (MH⁺).

(c) [3-Chloro-5-(1,3-dioxolan-2-yl)-2-pyridinyl]methanol

Trifluoroacetic anhydride (231 μl, 1.635 mmol) was added to a solution of 3-chloro-5-(1,3-dioxolan-2-yl)-2-methylpyridine 1-oxide (225 mg, 1.043 mmol) in DCM (4 ml) at 0° C. and the mixture was stirred at room temperature for 48 h. Full conversion was observed by HPLC. MeOH (0.5 ml, 12.36 mmol) was added and, after stirring for 10 min, DCM and 10% Na₂CO₃ solution were added. Extraction, drying (MgSO₄), and filtration afforded 223.2 mg of crude material.

Purification by flash chromatography using Flashmaster II, a 5 g silica gel cartridge, and mixtures of hexane and EtOAc as eluent afforded [3-chloro-5-(1,3-dioxolan-2-yl)-2-pyridinyl]methanol (142.7 mg, 63%) as a yellow oil.

$^1$H-NMR (δ, ppm, CDCl$_3$): 8.57 (s, 1H), 7.82 (s, 1H), 5.88 (s, 1H), 4.82 (s, 2H), 4.18-4.04 (m, 4H). [ES MS] m/z 216 (MH$^+$).

(d) Title compound:
5-Chloro-6-(hydroxymethyl)-3-pyridinecarbaldehyde

Oxalic acid (415 mg, 3.29 mmol) was added to a mixture of [3-chloro-5-(1,3-dioxolan-2-yl)-2-pyridinyl]methanol (142 mg, 0.659 mmol), acetone (7.5 ml), and water (7.5 ml) at room temperature and heated under reflux. After 2.5 h, HPLC showed full conversion. Cooled to rt, basified with 1M NaOH, extracted with TBME, dried (MgSO$_4$), filtered and concentrated to give 139 mg of crude material. Purification by flash chromatography using Flashmaster II, a 5 g silica gel cartridge, and mixtures of DCM and MeOH as eluent afforded impure product. Repurification by manual flash chromatography using a 1 g silica gel cartridge, and mixtures of hexane and EtOAc as eluent afforded 5-chloro-6-(hydroxymethyl)-3-pyridinecarbaldehyde (11.3 mg, 10%) as a white solid.

$^1$H-NMR (δ, ppm, CDCl$_3$): 10.12 (s, 1H), 8.95 (s, 1H), 8.17 (s, 1H), 4.90 (s, 2H), [ES MS] m/z 172 (MH$^+$), Preparation 9

5,6-Dimethyl-3-pyridinecarbaldehyde (Used to prepare Examples 13 and 14)

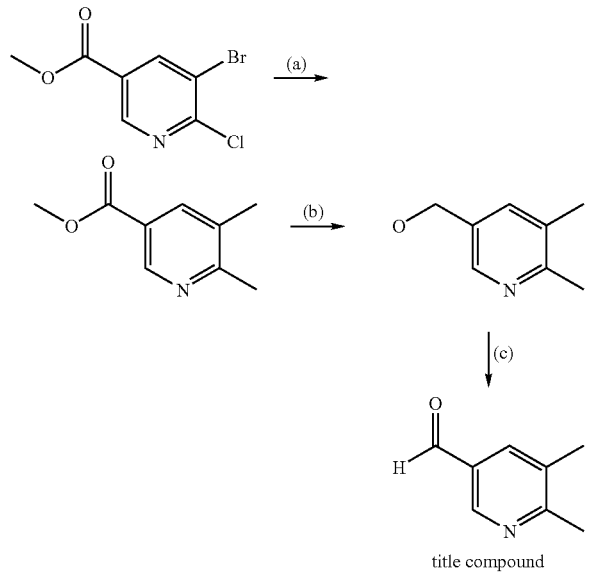

title compound (a) Methyl 5,6-dimethyl-3-pyridinecarboxylate

To a mixture of methyl 5-bromo-6-chloro-3-pyridinecarboxylate (595 mg, 2.375 mmol), tetrakis(triphenylphosphine)palladium (0) (275 mg, 0.238 mmol) and K$_2$CO$_3$ (492 mg, 3.56 mmol) in dioxane (6.5 ml), trimethylboroxin (1.328 ml, 9.50 mmol) was added under argon. The reaction mixture was heated at 110° C. for 16 h. The reaction mixture was allowed to cool down, filtered through a pad of silica, and concentrated to give 857 mg of the crude material. Purification by flash chromatography using Flashmaster II, a 20 g silica gel cartridge, and mixtures of hexane and EtOAc as eluent afforded 276 mg of desired compound.

(b) (5,6-Dimethyl-3-pyridinyl)methanol

To a solution of methyl 5,6-dimethyl-3-pyridinecarboxylate (276 mg, 1.671 mmol) in DCM (6 ml), DIBAL-H (1.5 M solution in toluene, 3.34 ml, 5.01 mmol) was added dropwise at −78° C. under N$_2$. The reaction mixture was allowed to warm to rt and stirred overnight. To this solution was added saturated, aqueous NaK-tartrate solution followed by DCM. The organic phase was separated, dried and concentrated to afford 175 mg of the crude material. Purification by flash chromatography using Flashmaster II, a 5 g silica gel cartridge, and mixtures of DCM/MeOH as eluent afforded 105 mg of desired compound.

(c) Title compound:
5,6-Dimethyl-3-pyridinecarbaldehyde

To a solution of (5,6-dimethyl-3-pyridinyl)methanol (105 mg, 0.765 mmol) in DCM (4 ml), MnO$_2$ (532 mg, 6.12 mmol) was added. After stirring overnight, an excess of MnO$_2$ (333 mg, 3.83 mmol) was added and then the mixture was stirred for 3 h more. The reaction mixture was filtrated and evaporated to afford 51 mg of title compound.

$^1$H-NMR (δ, ppm, CDCl$_3$): 10.05 (s, 1H), 8.75 (s, 1H), 7.87 (s, 1H), 2.60 (s, 3H), 2.30 (s, 3H).

Preparation 10

5-Chloro-6-ethyl-3-pyridinecarbaldehyde (Used to prepare Example 58)

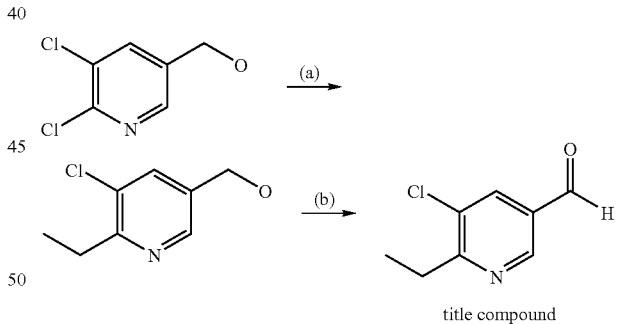

title compound (a) (5-Chloro-6-ethyl-3-pyridinyl)methanol

To a solution of (5,6-dichloro-3-pyridinyl)methanol (500 mg, 2.81 mmol), K$_2$CO$_3$ (1165 mg, 8.43 mmol), and [1,1'-Bis(diphenylphosphino) ferrocene]dichloro-palladium(II) (206 mg, 0.281 mmol) in THF (17 ml), was added diethylzinc (5.67 ml, 5.67 mmol). The mixture was stirred under reflux for 16 h in a pressure tube. The resulting mixture was quenched upon the addition of aqueous HCl until pH 7 and extracted with EtOAc. The combined organic layers were washed with brine, dried over MgSO$_4$, and concentrated under reduced pressure. The residue was purified by flash chromatography using Flashmaster II, spherical silica gel cartridge BP-SUP 20-40µ, and mixtures of EtOAc and hexane as eluents to give 103 mg of desired compound.

¹H-NMR (δ, ppm, CDCl₃): 8.34 (s, 1H), 7.69 (s, 1H), 4.68 (s, 2H), 2.94 (q, 2H), 2.49 (bs, 1H), 1.27 (t, 3H). [ES MS] m/z 172 (MH⁺).

(b) Title compound:
5-Chloro-6-ethyl-3-pyridinecarbaldehyde

MnO₂ (620 mg, 7.13 mmol) was added to a solution of (5-chloro-6-ethyl-3-pyridinyl)methanol (103 mg, 0.600 mmol) in DCM (4 ml) and the mixture was stirred at room temperature overnight. TLC (10% DCM/MeOH) showed starting material remaining. An excess of MnO₂ (261 mg, 3.00 mmol) was added. After stirring for 3 h, the reaction went to completion. The resulting suspension was filtered and washed with DCM. The filtrate was concentrated under reduced pressure to give 52 mg of the title compound as colourless oil.

¹H-NMR (δ, ppm, CDCl₃): 10.10 (s, 1H), 8.75 (s, 1H), 8.10 (s, 1H), 3.15 (q, 2H), 1.35 (t, 3H).

Preparation 11

N-[(5-Chloro-6-methyl-3-pyridinyl)methyl]-4-piperidinamine (used to prepare Example 2 compound via Scheme 4)

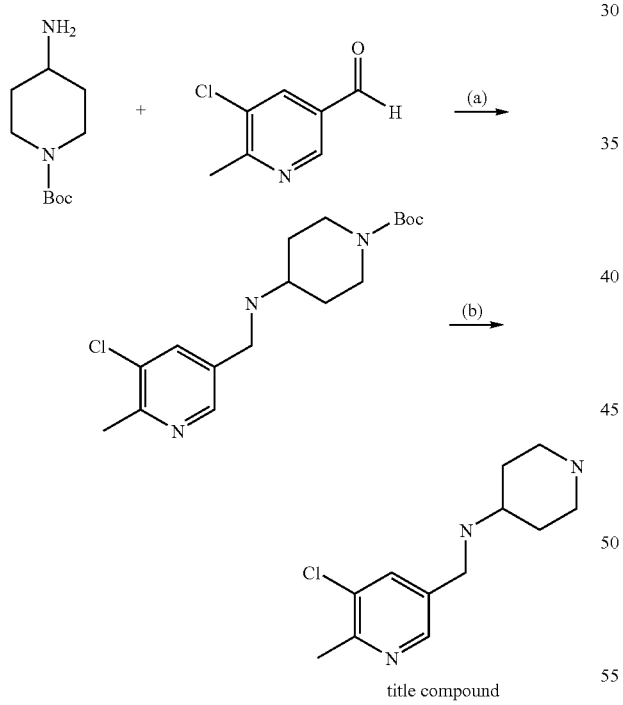

title compound (a) 1,1-Dimethylethyl 4-{[(5-chloro-6-methyl-3-pyridinyl)methyl]amino}-1-piperidinecarboxylate A solution of 1,1-dimethylethyl 4-amino-1-piperidinecarboxylate (11.19 g, 55.9 mmol), 5-chloro-6-methyl-3-pyridinecarbaldehyde (for a synthesis see WO2006/137485 A1 Example 256) (7.82 g, 50.3 mmol) and Na₂SO₄ (8.73 g, 61.5 mmol) in DCE (200 ml) was stirred at 90° C. for 4.5 h and at room temperature overnight. NaBH(OAc)₃ (35.5 g, 168 mmol) was added portionwise for 7 h until imine was not detected by LCMS analysis. 10% NaHCO₃ was added and the organic phase was extracted twice with DCM, washed with brine, dried (MgSO₄), filtered and concentrated under reduced pressure to give 1,1-dimethylethyl 4-{[(5-chloro-6-methyl-3-pyridinyl)methyl]amino}-1-piperidinecarboxylate (18.7 g, 94%) as a yellow oil.

¹H-NMR (δ, ppm, CDCl₃): 8.30 (d, 1H), 7.64 (s, 1H), 4.01 (bs, 2H), 3.78 (s, 2H), 2.79 (t, 2H), 2.67-2.59 (m, 1H), 2.59 (s, 3H), 1.83 (bd, 2H), 1.44 (s, 9H), 1.33-1.20 (m, 2H). [ES MS] m/z 340 (MH⁺).

(b) Title compound: N-[(5-Chloro-6-methyl-3-pyridinyl)methyl]-4-piperidinamine

A solution of 1,1-dimethylethyl 4-{[(5-chloro-6-methyl-3-pyridinyl)methyl]amino}-1-piperidinecarboxylate (65.58 g, 193 mmol) in DCM (800 ml) at 0° C. was treated with HCl (4M solution in 1,4-dioxane, 386 ml, 1544 mmol) and stirred at room temperature overnight. The resulting white suspension was filtered, washed with DCM and hexane and dried to obtain N-[(5-chloro-6-methyl-3-pyridinyl)methyl]-4-piperidinamine dihydrochloride (62.3 g) as a white solid. The crude product was dissolved in DCM/MeOH 5% (800 ml) and 2N NaOH (500 ml) was added until pH 13.8. Organic phase was extracted and aqueous phase was extracted again with DCM/MeOH 10% (650 ml×2). Combined organic phases were washed with brine, dried (MgSO₄), filtered and concentrated under vacuum to give N-[(5-chloro-6-methyl-3-pyridinyl)methyl]-4-piperidinamine (44.82 g, 97%).

¹H-NMR (δ, ppm, CDCl₃): 8.31 (s, 1H), 7.66 (s, 1H), 3.79 (s, 2H), 3.13 (dt, 2H), 2.68-2.56 (m, 3H), 2.60 (s, 3H), 2.02-1.83 (m, 2H), 1.38-1.26 (m, 2H). [ES MS] m/z 240 (MH⁺).

Preparation 12

5-Methyl-6-(trifluoromethyl)-3-pyridinecarbaldehyde (Used to prepare Examples 60 and 75)

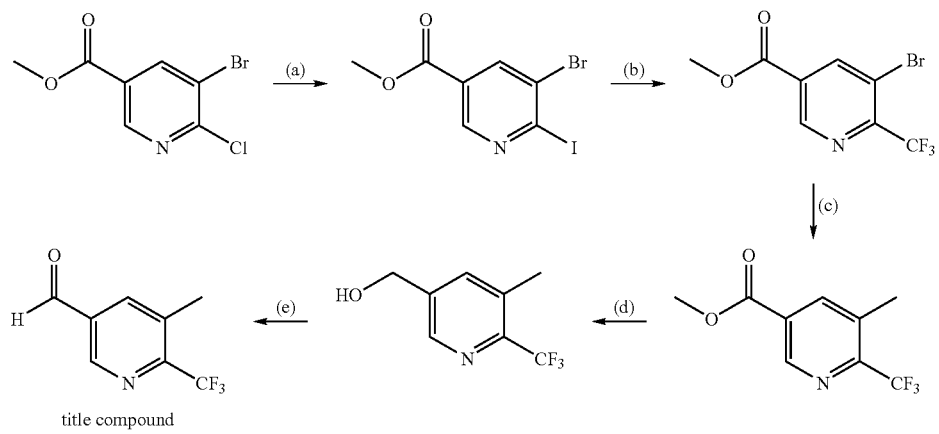

title compound

(a) Methyl 5-bromo-6-iodo-3-pyridinecarboxylate

To a solution of methyl 5-bromo-6-chloro-3-pyridinecarboxylate (4500 mg, 17.97 mmol) in HI (30 ml) was added NaI (3501 mg, 23.36 mmol). The mixture was stirred at 50° C. overnight. Reaction was cooled at 0° C. and the precipitated solid was isolated by filtration and washed with 15 ml of MeOH. The obtained solid was suspended in 25 ml of water and pH was adjusted to 9 with NaOH 6N (1.5 ml). The aqueous phase was extracted twice with DCM and once with DCM/MeOH (5%). Organic layers were dried over $Na_2SO_4$. Volatiles were removed under vacuum to afford 2.505 g (40%) of the desired compound as a white solid. The solution of HI and MeOH was dissolved in water and pH was adjusted to 9 with NaOH 6N. The organic phase was extracted twice with DCM and once with DCM/MeOH (5%). Organic layers were dried over $Na_2SO_4$. Volatiles were removed under vacuum to afford an additional quantity of the desired compound (649 mg, 10%) as beige solid.

$^1$H-NMR (δ, ppm, $CDCl_3$): 8.85 (1H, s), 8.37 (1H, s), 3.97 (3H, s).

(b) Methyl 5-bromo-6-(trifluoromethyl)-3-pyridinecarboxylate

To a solution of methyl 5-bromo-6-iodo-3-pyridinecarboxylate (3140 mg, 9.18 mmol) and CuI (2274 mg, 11.94 mmol) in dry DMF (25 ml) stirred under Ar, methyl 2,2-difluoro-2-(fluorosulfonyl)acetate (5.84 ml, 45.9 mmol) and hexamethylphosphoramide (7.99 ml, 45.9 mmol) were added. The reaction mixture was stirred at 80° C. in a pressure tube overnight. HPLC showed starting material remaining, more CuI was added until starting material was not detected by HPLC. The reaction mixture was evaporated and the residue was dissolved in 1N $NH_4Cl$ and EtOAc. The organic layer was separated, washed with $NH_4Cl$ and sat. NaCl, dried over anhydrous $Na_2SO_4$, filtered and evaporated under reduced pressure. Purification by flash chromatography using a 50 g silica gel cartridge, and mixtures of hexane and EtOAc as eluent afforded methyl 5-bromo-6-(trifluoromethyl)-3-pyridinecarboxylate (1.8 g, 40%).

$^1$H-NMR (δ, ppm, $CDCl_3$): 9.18 (1H, s), 8.66 (1H, s), 4.02 (3H, s).

(c) Methyl 5-methyl-6-(trifluoromethyl)-3-pyridinecarboxylate

To a solution of methyl 5-bromo-6-(trifluoromethyl)-3-pyridinecarboxylate (1173 mg, 4.13 mmol) in 1,4-dioxane (25 ml) stirred under $N_2$ was added $K_2CO_3$ (1712 mg, 12.39 mmol), trimethylboroxine (0.866 ml, 6.19 mmol) and tetrakis(triphenylphosphine)palladium (0) (239 mg, 0.206 mmol). The reaction mixture was stirred heating under reflux for 24 h. HPLC showed starting material remaining, more tetrakis(triphenylphosphine)palladium (0) was added until starting material was not detected by HPLC. The reaction mixture was diluted with water and extracted with EtOAc. The combined organic phases were washed with sat. NaCl, dried over anhydrous $Na_2SO_4$, filtered and concentrated under reduced pressure. Purification by flash chromatography using a 40 g Merck silica gel cartridge, and mixtures of hexane and EtOAc as eluent afforded methyl 5-methyl-6-(trifluoromethyl)-3-pyridinecarboxylate (304 mg, 32%).

$^1$H-NMR (δ, ppm, $CDCl_3$): 9.08 (1H, s), 8.27 (1H, s), 4.00 (3H, s), 2.57 (3H, s).

(d) [5-Methyl-6-(trifluoromethyl)-3-pyridinyl]methanol

To a solution of methyl 5-methyl-6-(trifluoromethyl)-3-pyridinecarboxylate (552 mg, 2.52 mmol) in DCM (30 ml) stirred under $N_2$ at 0° C. was added a solution of DIBAL-H (1.5 M solution in toluene, 5.04 ml, 7.56 mmol) dropwise. The reaction mixture was stirred at 0° C. for 2 h and at room temperature overnight. The reaction mixture was diluted with MeOH and concentrated under reduced pressure. The residue was treated with a 1N HCl solution and extracted twice with EtOAc. The combined organic phases were dried over anhydrous $Na_2SO_4$ and concentrated under reduced. Purification by flash chromatography using a 10 g silica gel cartridge, and mixtures of DCM and MeOH as eluent afforded [5-methyl-6-(trifluoromethyl)-3-pyridinyl]methanol (297 mg, 54%).

$^1$H-NMR (δ, ppm, $CDCl_3$): 8.48 (1H, s), 7.70 (1H, s), 4.81 (2H, s), 2.53 (3H, s).

(e) Title compound: 5-Methyl-6-(trifluoromethyl)-3-pyridinecarbaldehyde

To a solution of [5-methyl-6-(trifluoromethyl)-3-pyridinyl]methanol (152 mg, 0.795 mmol) in DCM (10 mL) was added $CrO_2$ (Magtrieve) (1336 mg, 15.90 mmol). The suspension was heated at 40° C. in a pressure tube overnight. The suspension was filtered over nylon membrane 0.45 μm and it was rinsed with DCM. The filtrate was evaporated to afford 120 mg (80%) of title compound pure enough to be used in the next step.

$^1$H-NMR (δ, ppm, CDCl$_3$): 10.19 (1H, s), 8.97 (1H, s), 8.14 (1H, s), 2.62 (3H, s).

Preparation 13

5-Chloro-6-(1-hydroxy-1-methylethyl)-3-pyridinecarbaldehyde (Used to prepare Example 62)

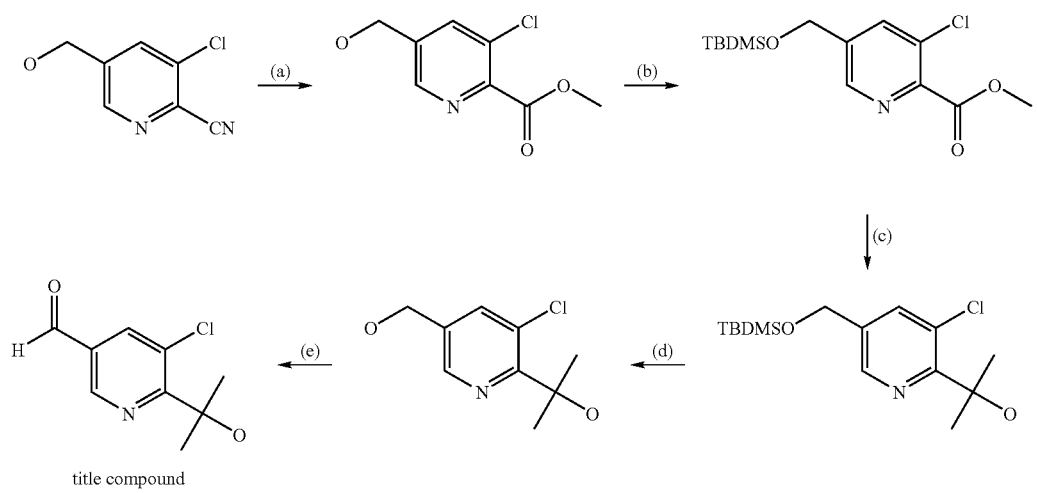

title compound

(a) Methyl 3-chloro-5-(hydroxymethyl)-2-pyridinecarboxylate

HCl (gas) was bubbled through a solution of 3-chloro-5-(hydroxymethyl)-2-pyridinecarbonitrile (for a synthesis see Preparation 4(a)) (400 mg, 2.373 mmol) in MeOH (25 mL) in ice bath. The mixture was refluxed overnight. HCl gas was bubbled through the solution for a few minutes. The mixture was refluxed overnight. HPLC showed starting material and desired compound. HCl gas was bubbled through the solution for a few minutes. The mixture was refluxed for two days. The mixture was concentrated in vacuo and dissolved with DCM. The organic layer was washed with saturated NaHCO$_3$ solution and brine, dried over Na$_2$SO$_4$, filtered and concentrated to give the title compound (332.6 mg, 66%) as brown oil pure enough to be used in the next step.

[ES MS] m/z 202 (MH$^+$).

(b) Methyl 3-chloro-5-({[(1,1-dimethylethyl)(dimethyl)silyl]oxy}methyl)-2-pyridinecarboxylate A solution of methyl 3-chloro-5-(hydroxymethyl)-2-pyridinecarboxylate (332.6 mg, 1.650 mmol), Et$_3$N (0.345 ml, 2.475 mmol), and tert-butyldimethylsilyl chloride (261 mg, 1.732 mmol) in DMF (4 ml) was stirred at room temperature for 3 h. The crude was diluted with TBME (40 ml) and organic phase was washed with water and brine. Combined organic phases were washed with sat NH$_4$Cl, dried over Na$_2$SO$_4$, filtered, and concentrated under reduced pressure to give the title compound (488 mg, 84% yield) as yellow oil pure enough to be used in the next step.

[ES MS] m/z 316 (MH$^+$).

(c) 2-[3-Chloro-5-({[(1,1-dimethylethyl)(dimethyl)silyl]oxy}methyl)-2-pyridinyl]-2-propanol To a solution of methyl 3-chloro-5-({[(1,1 dimethylethyl)(dimethyl)silyl]oxy}methyl)-2-pyridinecarboxylate (488 mg, 1.545 mmol) in THF (5 ml) at −23° C. was added methylmagnesium bromide (4.12 ml, 12.36 mmol) dropwise. After addition, the solution was allowed to warm to rt and stirred for 5 h. Saturated NH$_4$Cl was added after cooling the solution to 0° C. Water and EtOAc were added and the aqueous phase was extracted with EtOAc. The solution was dried over Na$_2$SO$_4$, filtered, and concentrated under reduced pressure. The crude material was purified by Flashmaster chromatography on a 10 g silica gel cartridge using hexane/EtOAc 95:5 as eluent to obtain 2-[3-chloro-5-({[(1,1-dimethylethyl)(dimethyl)silyl]oxy}methyl)-2-pyridinyl]-2-propanol (328 mg, 60% yield) as colourless oil.

[ES MS] m/z 316 (MH$^+$).

(d) 2-[3-Chloro-5-(hydroxymethyl)-2-pyridinyl]-2-propanol

To a solution of 2-[3-chloro-5-({[(1,1-dimethylethyl)(dimethyl)silyl]oxy}methyl)-2-pyridinyl]-2-propanol (328 mg, 1.038 mmol) in THF (10 ml) was added TBAF (1.557 ml, 1.557 mmol). The solution was stirred at room temperature for 3 h. The mixture was concentrated under vacuum and the residue was purified by Flashmaster chromatography on a 40 g Merk silica gel cartridge using DCM/MeOH 95:5 as eluent to obtain 2-[3-chloro-5-(hydroxymethyl)-2-pyridinyl]-2-propanol (210 mg, 95%) as colourless oil.

[ES MS] m/z 202 (MH$^+$).

(e) Title compound: 5-Chloro-6-(1-hydroxy-1-methylethyl)-3-pyridinecarbaldehyde CrO$_2$ (Magtrieve) (1749 mg, 20.83 mmol) was added to a solution of 2-[3-chloro-5-(hydroxymethyl)-2-pyridinyl]-2-propanol (210 mg, 1.041 mmol) in DCM (10 mL) and the mixture was stirred at 40° C. overnight. The suspension was filtered over nylon membrane and it was rinsed with DCM. The process was repeated several times. The combined filtrates were concentrated to afford 5-chloro-6-(1-hydroxy-1-methylethyl)-3-pyridinecarbaldehyde (179 mg, 82%) as yellow solid. It was used in the next step without further purification.

$^1$H-NMR (δ, ppm, CDCl$_3$): 10.11 (1H, s), 8.89 (1H, s), 8.19 (1H, s), 5.87 (1H, s), 1.72 (6H, s). [ES MS] m/z 200 (MH$^+$).

Preparation 14

Used to Prepare Example 72

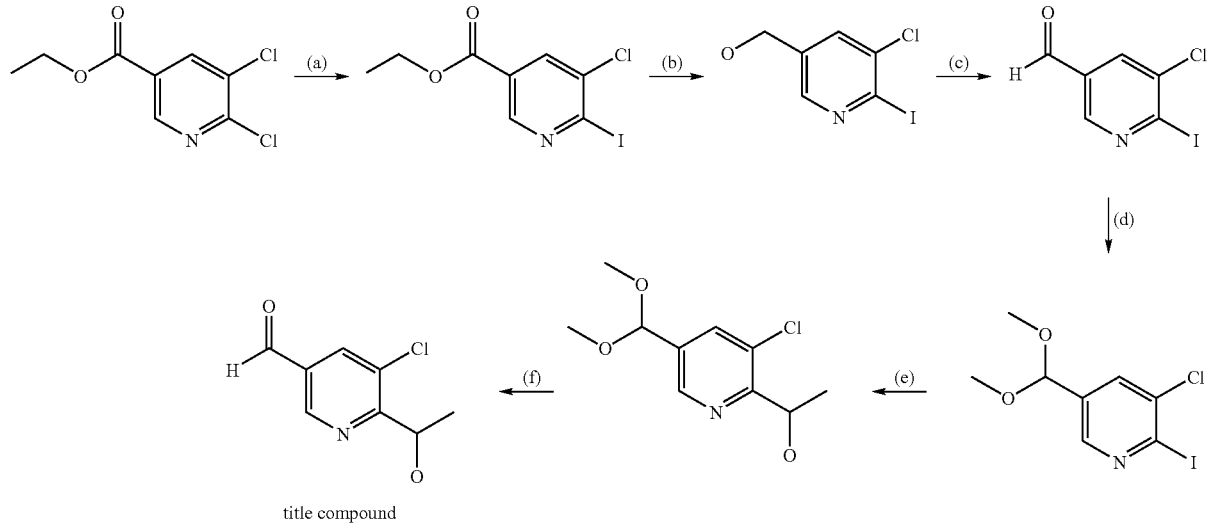

(a) Ethyl 5-chloro-6-iodo-3-pyridinecarboxylate

To a solution of ethyl 5,6-dichloro-3-pyridinecarboxylate (1.00 g, 4.54 mmol) in propionitrile (30 ml) stirred under nitrogen at room temperature was added sodium iodide (2.044 g, 13.63 mmol) and iodotrimethylsilane (0.784 ml, 4.54 mmol). After stirring for 30 min, solvent was evaporated to dryness. The obtained brown oil was dissolved in water and pH was adjusted to basic with 2N NaOH. The aqueous phase was extracted with DCM, dried over anhydrous $MgSO_4$ and concentrated under reduced pressure. Purification by flash chromatography using Flashmaster II, a 10 g silica gel cartridge, and mixtures of DCM/MeOH as eluent afforded a mixture of final product and ethyl 5-chloro-3-pyridinecarboxylate. The mixture was repurification by flash chromatography using Flashmaster II, a 50 g Merck silica gel cartridge, and mixtures of DCM/MeOH as eluent afforded the expected product ethyl 5-chloro-6-iodo-3-pyridinecarboxylate as a white solid.

$^1$H-NMR (δ, ppm, $CDCl_3$): 8.82 (s, 1H), 8.21 (s, 1H), 4.46-4.39 (q, 2H), 1.44-1.40 (t, 3H). [ES MS] m/z 174 ($MH^+$).

(b) (5-Chloro-6-iodo-3-pyridinyl)methanol

DIBAL-H (3.37 ml, 3.37 mmol) was slowly added to a solution of ethyl 5-chloro-6-iodo-3-pyridinecarboxylate (500 mg, 1.605 mmol) in THF (10 ml) at −78° C. The solution turned yellow and was stirred at that temperature for 3 h and then still in the dry-ice bath allowed to slowly attain room temperature overnight. Next morning, TLC showed starting material remaining. The solution was cooled to −78° C. and DIBAL-H (3.37 ml, 3.37 mmol) was added. 3 h later it was allowed to warm to room temperature and after 2 h starting material was still observed. More DIBAL-H (6.74 ml) was added and the solution stirred at room temperature overnight. Full conversion was observed. Saturated, aqueous NaK-tartrate solution and EtOAc were added. Extraction, drying ($MgSO_4$), filtration, and concentration afforded (5-chloro-6-iodo-3-pyridinyl)methanol (393 mg, 91%) as a brown solid pure enough to be used in the next step.

$^1$H-NMR (δ, ppm, $CDCl_3$): 8.24 (s, 1H), 7.71 (s, 1H), 4.71 (s, 2H), 2.12 (bs, 1H). [ES MS] m/z 270 ($MH^+$).

(c) 5-Chloro-6-iodo-3-pyridinecarbaldehyde

A mixture of (5-chloro-6-iodo-3-pyridinyl)methanol (392 mg, 1.455 mmol), $CrO_2$ (Magtrieve) (2.444 g, 29.1 mmol), and DCM (20 ml) was stirred at 40° C. for 24 h. Some starting material was still observed by TLC. More $CrO_2$ (0.61 g) was added and the suspension stirred at 40° C. overnight. TLC showed full conversion. Filtration and concentration afforded 5-chloro-6-iodo-3-pyridinecarbaldehyde (261 mg, 67%) as a brown solid pure enough to be used in the next step.

$^1$H-NMR (δ, ppm, $CDCl_3$): 10.08 (s, 1H), 8.68 (s, 1H), 8.07 (s, 1H). [ES MS] m/z 267 ($MH^+$).

(d) 5-[Bis(methyloxy)methyl]-3-chloro-2-iodopyridine

A mixture of 5-chloro-6-iodo-3-pyridinecarbaldehyde (260 mg, 0.972 mmol), trimethyl orthoformate (1.064 ml, 9.72 mmol), HCl (3M in MeOH) (0.778 ml, 2.333 mmol), DCM (1.5 ml) and MeOH (1.5 ml) was stirred at 50° C. for 3 h. TLC showed full conversion. The solution was cooled to room temperature and concentrated under vacuum. The residue was diluted with sat. $NaHCO_3$ and EtOAc. Extraction, drying ($MgSO_4$), filtration, and concentration afforded 271.5 mg of crude material. Purification by flash chromatography using Flashmaster II, a 5 g silica gel cartridge, and mixtures of hexane and EtOAc as eluent afforded 5-[bis(methyloxy)methyl]-3-chloro-2-iodopyridine (239.9 mg, 79%) as a yellow oil. It will be used in the next step without further purification.

$^1$H-NMR (δ, ppm, $CDCl_3$): 8.35 (s, 1H), 7.75 (s, 1H), 5.45 (s, 1H), 3.34 (s, 6H). [ES MS] m/z 314 ($MH^+$).

(e) 1-{5-[Bis(methyloxy)methyl]-3-chloro-2-pyridinyl}ethanol

A solution of 5-[bis(methyloxy)methyl]-3-chloro-2-iodopyridine (239 mg, 0.762 mmol) in THF (1.5 ml) was slowly added to a solution of i-PrMgCl (400 μl, 0.800 mmol) in THF (1.5 ml) at −20° C. under $N_2$ and the mixture was stirred at that temperature. After 30 min a small amount of starting material was still observed by LCMS. After 2 h, LCMS still showed some starting material. More i-PrMgCl (60 μl) was added and after 40 min disappearance of the starting material was observed by LCMS. Acetaldehyde (47 μl, 0.841 mmol) was added and the mixture stirred at −20° C. for 10 min. Partial conversion was observed by LCMS and no evolution was observed after 1 h. Excess acetaldehyde was added but no changes were observed after 30 min by LCMS. Then, it was quenched with saturated NH$_4$Cl, extracted with EtOAc, dried (MgSO$_4$), filtered, and concentrated to afford 177.4 mg of crude material as a brown oil. The mixture was purified by flash chromatography using Flashmaster II, a 10 g Merck silica gel cartridge, and mixtures of hexane and EtOAc as eluent. 1-{5-[bis(methyloxy)methyl]-3-chloro-2-pyridinyl}ethanol (67 mg, 38%) was isolated as a yellow oil.

$^1$H-NMR (δ, ppm, CDCl$_3$): 8.52 (s, 1H), 7.78 (s, 1H), 5.45 (s, 1H), 5.20-5.11 (m, 1H), 4.40-4.37 (d, 1H), 3.34 (s, 6H), 1.47-1.45 (d, 3H). [ES MS] m/z 232 (MH$^+$).

(f) Title compound:
5-Chloro-6-(1-hydroxyethyl)-3-pyridinecarbaldehyde

1-{5-[Bis(methyloxy)methyl]-3-chloro-2-pyridinyl}ethanol (66 mg, 0.285 mmol) was dissolved in EtOAc and washed with 1M HCl. The phases were separated and the aqueous one was taken to basic pH with 10% Na$_2$CO$_3$ and extracted with EtOAc, dried (MgSO$_4$), filtered, and concentrated to give 54.4 mg of a brown oil. By $^1$H-NMR, partial hydrolysis of the acetal (~20%) was observed. The crude was dissolved in EtOAc (5 ml), and stirred with 1 M HCl (5 ml, 5.00 mmol) at room temperature overnight. Basification with 10% Na$_2$CO$_3$, extraction with EtOAc, drying (MgSO$_4$), filtration, and concentration afforded 5-chloro-6-(1-hydroxyethyl)-3-pyridinecarbaldehyde (49.5 mg, 94%) as a brown oil impurified with ca. 6% starting material. It will be used for the next step without further purification.

$^1$H-NMR (δ, ppm, CDCl$_3$): 10.12 (s, 1H), 8.96 (s, 1H), 8.17 (s, 1H), 5.35-5.15 (m, 1H), 4.25 (d, 1H), 1.5 (d, 3H). [ES MS] m/z 185 (MH$^+$).

Preparation 15

Used to Prepare Example 61

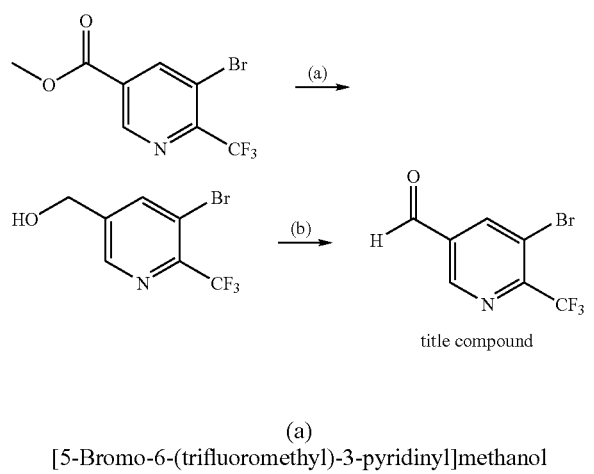

(a)
[5-Bromo-6-(trifluoromethyl)-3-pyridinyl]methanol

To a solution of methyl 5-bromo-6-(trifluoromethyl)-3-pyridinecarboxylate (for a synthesis see Preparation 12(b)) (698 mg, 2.457 mmol) in DCM (20 ml) stirred under N$_2$ at 0° C. was added DIBAL-H (1.5 M solution in toluene, 4.91 ml, 7.37 mmol) dropwise. The reaction mixture was stirred at 0° C. for 3 h and at room temperature overnight. The reaction mixture was diluted with MeOH and concentrated under reduced pressure. The residue was treated with a 1N HCl solution and extracted twice with EtOAc. The combined organic phases were dried over anhydrous Na$_2$SO$_4$ and concentrated under reduced. The crude material was purified by Flashmaster chromatography on a 10 g silica gel cartridge using hexane/EtOAc 95:5 as eluent to afford [5-bromo-6-(trifluoromethyl)-3-pyridinyl]methanol (297 mg, 54%) no pure enough to be used in the next step. The title compound was re-purified by preparative HPLC (column XTerra 30×150 mm, gradient elution: 30 to 80% CH$_3$CN/H$_2$O, uv detection 254 nm) to give the title compound (157 mg, 24%).
[ES MS] m/z 256 (MH$^+$).

(b) Title compound:
5-Bromo-6-(trifluoromethyl)-3-pyridinecarbaldehyde

To a solution of [5-bromo-6-(trifluoromethyl)-3-pyridinyl]methanol (155 mg, 0.605 mmol) in DCM (10 mL) was added CrO$_2$ (Magtrieve) (1017 mg, 12.11 mmol). The suspension was heated at 40° C. in a pressure tube overnight. TLC showed starting material remaining, an excess of CrO$_2$ (254 mg, 3.03 mmol) was added. The reaction mixture was heated at 40° C. for 4 h. The suspension was filtered over nylon membrane 0.45 μm and it was rinsed with DCM. The filtrate was evaporated under vacuum to afford 120 mg (78%) of title compound pure enough to be used in the next step.

$^1$H-NMR (δ, ppm, CDCl$_3$): 10.18 (1H, s), 9.07 (1H, s), 8.53 (1H, s).

Preparation 16

6-Chloro-5-methyl-3-pyridazinecarbaldehyde (Used to prepare Example 73)

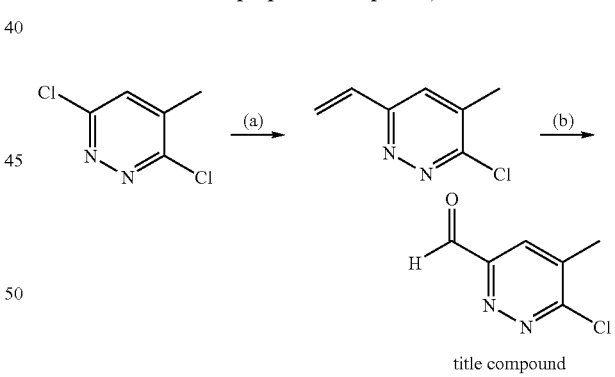

(a) 3-Chloro-6-ethenyl-4-methylpyridazine

An orange solution of tributyl(vinyl)tin (0.359 ml, 1.227 mmol), bis(triphenylphosphine)palladium(II) chloride (43.1 mg, 0.061 mmol), and 3,6-dichloro-4-methylpyridazine (200 mg, 1.227 mmol) in DMF (2 ml) was stirred at room temperature under argon overnight. Some starting material was still present so it was stirred at room temperature all the weekend. No further evolution was observed. KF (80 mg, 1.377 mmol), TBME (4 ml) and water (4 ml) were added and the mixture was stirred at room temperature for 30 min. The solids were filtered off. Extraction, drying (MgSO$_4$), filtration, and concentration afforded 437.7 mg of crude material. Purification by flash chromatography using Flashmaster II, a 20 g Merck gel cartridge, and mixtures of hexane and EtOAc (0-30%) as eluant afforded 3-chloro-6-ethenyl-4-methylpyridazine (34.8 mg, 18%), as white solid.

$^1$H-NMR (δ, ppm, CDCl$_3$): 7.45 (s, 1H); 7.05-6.95 (dd, 1H); 6.26-6.20 (d, 1H); 5.72-5.68 (d, 1H); 2.43 (s, 3H). [ES MS] m/z 154 (MH$^+$).

(b) Title compound:
6-Chloro-5-methyl-3-pyridazinecarbaldehyde

To a white suspension of 3-chloro-6-ethenyl-4-methylpyridazine (34.1 mg, 0.221 mmol), NaIO$_4$ (189 mg, 0.882 mmol), 4-methylmorpholine N-oxide (28.4 mg, 0.243 mmol) in CH$_3$CN (3 mL) and water (1.5 mL) was added OsO$_4$ (0.013 mL, 2.206 µmol), and the mixture was stirred at room temperature for 3 days. The reaction was monitored by LCMS and starting material was observed. The reaction mixture was heated at 60° C. overnight and no more starting material was observed. Solvents were evaporated in vacuo and the residue was partitioned between EtOAc and water. The aqueous layer was extracted with additional EtOAc. The combined organic phases were washed with water, dried with over anhydrous MgSO$_4$, filtered and concentrated under reduced pressure to give 31.1 mg of the title compound as a white solid. It will be used in the next step without prior purification.

$^1$H-NMR (δ, ppm, CDCl$_3$): 10.33 (s, 1H), 7.89 (s, 1H), 2.52 (s, 3H). [ES MS] m/z 156 (MH$^+$).

Preparation 17

6-Chloro-5-methyl-3-pyridinecarbaldehyde (Used to prepare Example 74)

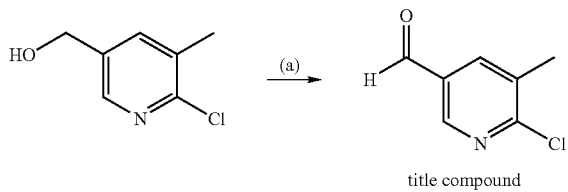

A mixture of (6-chloro-5-methyl-3-pyridinyl)methanol (300 mg, 1.904 mmol), CrO$_2$ (Magtrieve) (2.398 g, 28.5 mmol), and DCM (15 ml) was stirred at 40° C. in a closed tube overnight. TLC showed some starting material remaining. Additional CrO$_2$ (0.8 g) was added. After heating 4 additional hours, TLC showed full conversion. Filtration and concentration afforded 6-chloro-5-methyl-3-pyridinecarbaldehyde (204.8 mg, 69%) as a white solid.

$^1$H-NMR (δ, ppm, CDCl$_3$): 10.07 (s, 1H), 8.70 (s, 1H), 8.02 (s, 1H), 2.48 (s, 3H). [ES MS] m/z 156 (MH$^+$).

Preparation 18

Used to Prepare Example 71

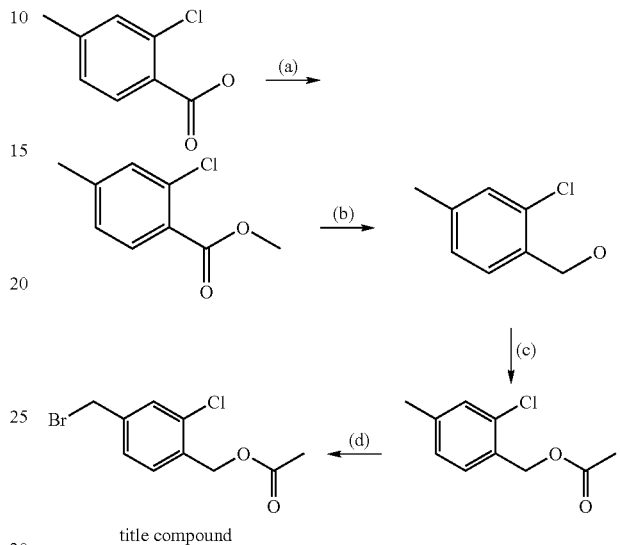

(a) methyl 2-chloro-4-methylbenzoate 2-chloro-4-methylbenzoic acid (500 mg, 2.93 mmol) was dissolved in Methanol (7 mL) and SOCl$_2$ (0.215 mL, 2.93 mmol) was slowly added to the mixture and the reaction was left at room temperature overnight. Next morning HPLC showed completion. Volatiles were removed under vacuum to afford 526 mg of the title compound as brown oil.

$^1$H-NMR (δ ppm, DMSO): 7.71 (d, 1H), 7.40 (s, 1H), 7.25 (s, 1H), 3.81 (s, 3H), 2.33 (s, 3H).

(a) (2-chloro-4-methylphenyl)methanol

Methyl 2-chloro-4-methylbenzoate (520 mg, 2.82 mmol) was dissolved in Dichloromethane (DCM) (15 mL) and at 0° C. Dibal-H (4.694 ml, 7.04 mmol) was slowly added. The mixture was left at 0° C. for 2H and then at room temperature overnight. Next morning HPLC showed no starting material remaining, reaction was quenched with Rochelle salt, and leaving under stirring for 1 hour and then it was extracted with DCM, dried and concentrated to afford 365 mg of the final compound, pure enough to be used in the next step.

$^1$H-NMR (δ ppm, CDCl$_3$): 7.35-7.07 (m, 3H), 4.74 (s, 2H), 2.33 (s, 2H).

(b) (2-chloro-4-methylphenyl)methyl acetate

To a solution of (2-chloro-4-methylphenyl)methanol (365 mg, 2.331 mmol) and Et$_3$N (0.390 mL, 2.80 mmol) in Dichloromethane (DCM) (10 mL) at 0° C. AcOCl (0.331 mL, 4.66 mmol) was slowly added and the mixture was left under stirring at 0° C. for 1 hour then at room temperature overnight. Next morning HPLC showed no starting material remaining volatiles were removed under vacuum and resulting crude was dissolved in DCM washed several times with water.

Organic layers were dried over Na$_2$SO$_4$ and volatiles removed to afford 453 mg of the final compound as a brown oil.

$^1$H-NMR (δ ppm, CDCl$_3$): 7.30 (d, 1H), 7.06 (s, 1H), 5.11 (s, 2H), 2.33 (s, 3H), 2.11 (s, 3H).

(c) [4-(bromomethyl)-2-chlorophenyl]methyl acetate (2-chloro-4-methylphenyl)methyl acetate (453 mg, 2.280 mmol) was dissolved in Chloroform (20 mL) and AIBN (18.72 mg, 0.114 mmol) and NBS (406 mg, 2.280 mmol) were added under Ar atmosphere. The reaction was left under reflux for 5 hours. HPLC showed a new pick which we thought it was the desired product and a bit of starting material and the reaction was stopped. The mixture was allowed to reach room temperature, succinimide was filtered, and volatiles removed under vacuum. Corresponding crude was purified by using flash master chromatography Si II MERCK, 20 g Hexane-acetate (0-30%).

When purification was done, it was found out that main compound was starting material (210 mg), and just 35 mg of the desired compound were obtained.

$^1$H-NMR (δ ppm, CDCl$_3$): 7.44-7.20 (m, 3H), 5.2011 (s, 2H), 4.43 (s, 2H), 2.13 (s, 3H).

Preparation 19

5-Chloro-6-[2-(methyloxy)ethyl]-3-pyridinecarbaldehyde (Used to prepare Example 65)

(1.174 ml, 8.43 mmol) were added. The mixture reaction was stirred overnight. The crude was diluted with TBME (175 mL) and water. The organic phase was washed with solution sat. NaCl. Combined organics were washed with sat NH$_4$Cl and dried over Na$_2$SO$_4$, filtered, and concentrated under reduced pressure. Purification by flash chromatography using Flashmaster II, a 50 g silica gel cartridge, and mixtures of hexane and EtOAc as eluent afforded 2,3-Dichloro-5-({[(1,1-dimethylethyl)(dimethyl)silyl]oxy}methyl)pyridine 2.5 g (72%) of a yellow oil.

[ES MS] m/z 292 (MH$^+$).

(b) 3-Chloro-5-({[(1,1-dimethylethyl)(dimethyl)silyl]oxy}methyl)-2-ethenylpyridine In a sealed tube charged with a solution of 2,3-dichloro-5-({[(1,1-dimethylethyl)(dimethyl)silyl]oxy}methyl)pyridine (1500 mg, 5.13 mmol) in 1,4-dioxane (20 ml) was added K$_2$CO$_3$ (2128 mg, 15.40 mmol). The mixture was degassed with N$_2$, then vinylboronic anhydride pyridine complex (1235 mg, 5.13 mmol) and tetrakis(triphenylphosphine)palladium (0) (178 mg, 0.154 mmol) were added. The reaction mixture was stirred at reflux temperature overnight. The crude was diluted with water and extracted twice with EtOAc. The combined organic phases were washed with water and with sat. NaCl, dried over anhydrous MgSO$_4$ and concentrated under vacuum. Purification by flash chromatography using Flashmaster II, a 50 g Merck silica gel cartridge, and

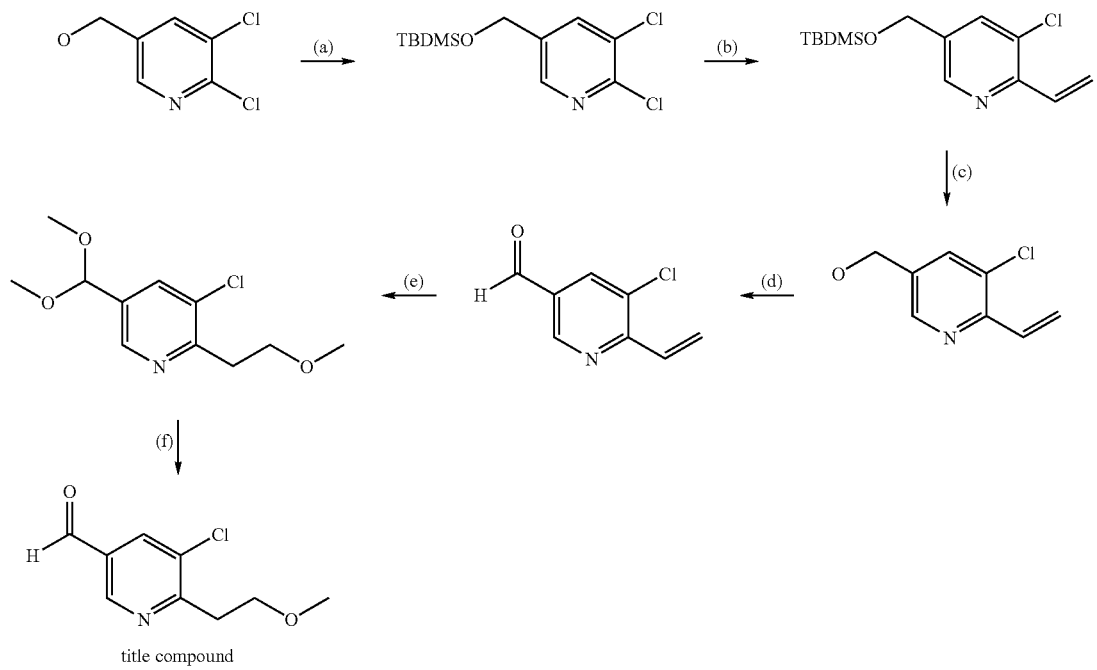

mixtures of hexane and EtOAc as eluent afforded 3-chloro-5-({[(1,1-dimethylethyl)(dimethyl)silyl]oxy}methyl)-2-ethenylpyridine (754 mg, 49%).

[ES MS] m/z 284 (MH$^+$).

(c) (5-Chloro-6-ethenyl-3-pyridinyl)methanol

A solution of 3-chloro-5-({[(1,1-dimethylethyl)(dimethyl)silyl]oxy}methyl)-2-ethenylpyridine (707 mg, 2.491 mmol)

(a) 2,3-Dichloro-5-({[(1,1-dimethylethyl)(dimethyl)silyl]oxy}methyl)pyridine

A mixture of (5,6-dichloro-3-pyridinyl)methanol (2000 mg, 11.23 mmol), Et$_3$N (2.349 ml, 16.85 mmol), and tert-butyldimethylsilyl chloride (1778 mg, 11.80 mmol) in DMF (20 ml) was stirred at room temperature for 4 h. HPLC analyse showed starting material remaining, an excess of tert-butyldimethylsilyl chloride (847 mg, 5.62 mmol) and Et$_3$N and TBAF (3.74 ml, 3.74 mmol) in THF (20 ml) was stirred at room temperature overnight. The mixture was concentrated and purified by flash chromatography using Flashmaster II, a 68 g Merck silica gel cartridge, and mixtures of DCM and MeOH as eluent to afford (5-chloro-6-ethenyl-3-pyridinyl) methanol (405 mg, 94%).

[ES MS] m/z 170 (MH$^+$).

(d) 5-Chloro-6-ethenyl-3-pyridinecarbaldehyde

To a solution of 5-chloro-6-ethenyl-3-pyridinyl)methanol (394 mg, 2.323 mmol) in DCM (20 mL) was added $CrO_2$ (Magtrieve) (3902 mg, 46.5 mmol). The suspension was stirred and heated at 40° C. in a pressure tube overnight. After overnight, TLC showed starting material remaining. More $CrO_2$ (1951 mg, 23.23 mmol) was added and the mixture was stirred for 5 h more. The suspension was filtered over nylon membrane 0.45 µm and the solvent was removed in vacuo to give 5-chloro-6-ethenyl-3-pyridinecarbaldehyde (222 mg, 55%).

[ES MS] m/z 168 MH$^+$).

(e) 5-[Bis(methyloxy)methyl]-3-chloro-2-[2-(methyloxy)ethyl]pyridine

In a sealed tube charged with a solution of 5-chloro-6-ethenyl-3-pyridinecarbaldehyde (114 mg, 0.680 mmol) in MeOH (2.5 ml) and DCM (1 ml) was added trimethyl orthoformate (0.074 ml, 0.680 mmol) and HCl (4M in dioxane) (0.408 ml, 1.633 mmol). The reaction mixture was stirred at 70° C. for 5 h and at rt overnight. The solution was concentrated under vacuum. The residue was diluted with sat. $NaHCO_3$ and was extracted with DCM and EtOAc. The combined organic phase was dried over anhydrous $Na_2SO_4$ and concentrated under reduced pressure. The crude was purification by flash chromatography using a 2 g silica gel cartridge, and EtOAc/Hexane 4:6 as eluent to give a mixture of 5-[bis(methyloxy)methyl]-3-chloro-2-[2-(methyloxy)ethyl] pyridine and 5-chloro-6-[2-(methyloxy)ethyl]-3-pyridinecarbaldehyde (2.5:1) (46.2 mg).

(f) 5-Chloro-6-[2-(methyloxy)ethyl]-3-pyridinecarbaldehyde

A mixture of 5-[bis(methyloxy)methyl]-3-chloro-2-[2-(methyloxy)ethyl]pyridine and 5-chloro-6-[2-(methyloxy) ethyl]-3-pyridinecarbaldehyde (2.5:1) (46.2 mg, 0.104 mmol) and 1M HCl (2 ml, 2.000 mmol) in DCM (2 mL) was stirred at rt for 2 days. DCM and 1M NaOH solution were added. Extraction, drying ($MgSO_4$), and filtration afforded 5-chloro-6-[2-(methyloxy)ethyl]-3-pyridinecarbaldehyde (38 mg, 9%) pure enough to be used in the next step.

$^1$H-NMR (δ, ppm, $CDCl_3$): 10.06 (1H, s), 8.90 (1H, s), 8.12 (1H, s), 3.87 (2H, t), 3.38 (3H, s), 3.33 (2H, t). [ES MS] m/z 200 (MH$^+$).

Alternative Oxidations to Obtain 5-chloro-6-methyl-3-pyridinecarbaldehyde (Formula (IIB))

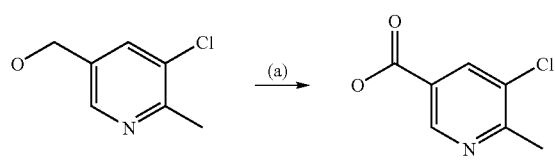

The preparation of this compound is known from WO2006/137485. Two further methods of preparing it were investigated.

Method A

A solution of 5-chloro-6-methyl-3-pyridinyl)methanol (for a synthesis see WO2006/137485 A1 Example 255) (10 g, 63.5 mmol) in DCM (500 ml) at room temperature was treated with $CrO_2$ (Magtrieve) (107 g, 1269 mmol) and stirred at 40° C. for 1 day. The reaction mixture was filtered through celite and the filtrate was evaporated under reduced pressure to give 5-chloro-6-methyl-3-pyridinecarbaldehyde (8.3 g, 85%) as a beige solid.

$^1$H-NMR (δ, ppm, $CDCl_3$): 10.05 (s, 1H), 8.83 (s, 1H), 8.09 (s, 1H), 2.73 (s, 3H).

Method B

Sulphur trioxide pyridene complex (1010 mg, 6.35 mmol) was suspended in dry DMSO (1.126 ml, 15.87 mmol). Then pyridine (0.513 ml, 6.35 mmol) was added and after 15 min under stirring, this solution was slowly added to other containing a mixture of (5-chloro-6-methyl-3-pyridinyl)methanol (for a synthesis see WO2006/137485 A1 Example 255) (500 mg, 3.17 mmol) and N,N-diisopropylethylamine (1.939 ml, 11.10 mmol) in a mixture of DMSO (1.12 ml) and DCM (4 ml) at 0° C. After 1 h under stirring, the ice bath was removed and the reaction was left at room temperature overnight. DCM was evaporated under vacuum, $H_2O$ and $Et_2O$ (1:1) were added and the aqueous layer was extracted several times with $Et_2O$. Organic layers were washed with brine, dried ($Na_2SO_4$), filtered and concentrated to afford 5-chloro-6-methyl-3-pyridinecarbaldehyde (435 mg, 88%) as a yellow solid.

$^1$H-NMR (δ, ppm, $CDCl_3$): 10.05 (s, 1H), 8.83 (s, 1H), 8.09 (s, 1H), 2.73 (s, 3H).

Biological Activity

Antimicrobial Activity Assay:

Whole-cell antimicrobial activity was determined by broth microdilution using the Clinical Laboratory Standards Institute (CLSI) recommended procedure, Document M7-A7, "Methods for Dilution Susceptibility Tests for Bacteria that Grow Aerobically".

Compounds were evaluated against Gram-positive organisms, including *Staphylococcus aureus, Streptococcus pneumoniae,* and *Enterococcus faecalis.*

In addition, compounds were evaluated against a panel of Gram-negative organisms including *Haemophilus influenzae, Moraxella catarrhalis, Escherichia coli,*

The minimum inhibitory concentration (MIC) was determined as the lowest concentration of compound that inhibited visible growth. A mirror reader was used to assist in determining the MIC endpoint.

Each of the compounds of the listed Examples 1-31 and 33-59 as identified in Table 1 of the present application, had a MIC <2 µg/ml against at least one of the organisms listed above. For at least one strain of every organism listed above, at least one Example had a MIC <2 µg/ml. The lowest MIC shown by the compound of Example 32 was 4 µg/ml against the organism *E. coli* 120 AcrAB-.

Examples were tested in the *Mycobacterium tuberculosis* H37Rv inhibition assay.

*Mycobacterium tuberculosis* H37Rv Inhibition Assay

The measurement of the minimum inhibitory concentration (MIC) for each tested compound was performed in 96 wells flat-bottom, polystyrene microtiter plates. Ten two-fold drug dilutions in neat DMSO starting at 400 µM were performed. Five µl of these drug solutions were added to 95 µl of Middlebrook 7H9 medium. (Lines A-H, rows 1-10 of the plate layout). Isoniazid was used as a positive control, 8 two-fold dilution of Isoniazid starting at 160 μgml[−1] was prepared and 5 μl of this control curve was added to 95 μl of Middlebrook 7H9 medium (Difco catalogue ref 271310). (Row 11, lines A-H). Five μl of neat DMSO were added to row 12 (growth and Blank controls).

The inoculum was standardised to approximately 1×10[7] cfu/ml and diluted 1 in 100 in Middlebrook 7H9 broth (Middlebrook ADC enrichment, a dehydrated culture media which supports growth of mycobacterial species available from Becton Dickinson Catalogue Ref. 211887), to produce the final inoculum of H37Rv strain (ATCC25618). One hundred μl of this inoculum was added to the entire plate but G-12 and H-12 wells (Blank controls). All plates were placed in a sealed box to prevent drying out of the peripheral wells and they were incubated at 37° C. without shaking for six days. A resazurin solution was prepared by dissolving one tablet of resazurin (Resazurin Tablets for Milk Testing; Ref 330884Y VWR International Ltd) in 30 ml sterile PBS (phosphate buffered saline). 25 μl of this solution was added to each well. Fluorescence was measured (Spectramax M5 Molecular Devices, Excitation 530 nm, Emission 590 nm) after 48 h to determine the MIC value.

All examples were tested in the *Mycobacterium tuberculosis* H37Rv inhibition assay except for examples 45 (tested as HCl salt), 58, 66, 67, 69. All tested Examples showed an MIC value of 2.42 μg/ml or lower. All tested Examples except Examples 13, 14, 22, 27, 35, 39, 40, 48, 52, 63, 64, 65 and 71 64 showed an MIC value of 1.0 μg/ml or lower.

TABLE 1

| Ex | Structure | Chemical name |
|---|---|---|
| 1 & 1A | 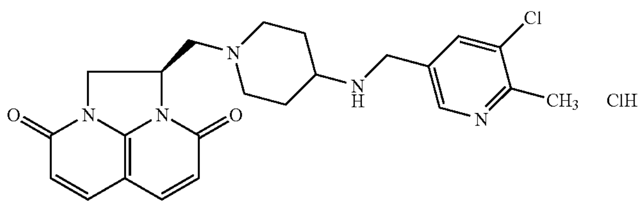 | (1R)-1-[4-{[(5-chloro-6-methyl-3-pyridinyl)methyl]amino}-1-piperidinyl)methyl]-1,2-dihydro-4H,9H-imidazo[1,2,3-ij]-1,8-naphthyridine-4,9-dione hydrochloride |
| 2 | 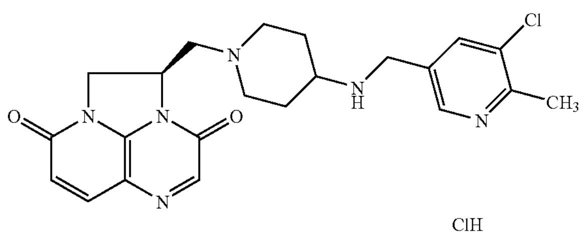 | (2R)-2-[(4-{[(5-chloro-6-methyl-3-pyridinyl)methyl]amino}-1-piperidinyl)methyl]-1,2-dihydro-3H,8H-2a,5,8a-triazaacenaphthylene-3,8-dione hydrochloride |
| 3 | 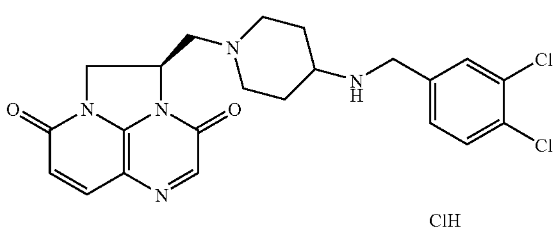 | (2R)-2-[(4-{[(3,4-dichlorophenyl)methyl]amino}-1-piperidinyl)methyl]-1,2-dihydro-3H,8H-2a,5,8a-triazaacenaphthylene-3,8-dione ClH |
| 4 | 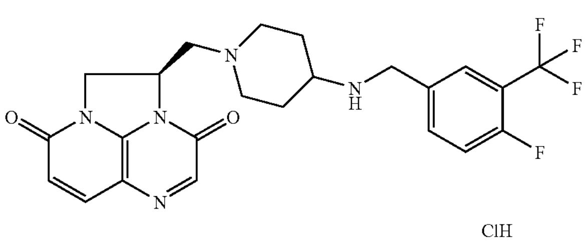 | (2R)-2-{[4-({[4-fluoro-3-(trifluoromethyl)phenyl]methyl}amino)-1-piperidinyl]methyl}-1,2-dihydro-3H,8H-2a,5,8a-triazaacenaphthylene-3,8-dione hydrochloride |
| 5 | 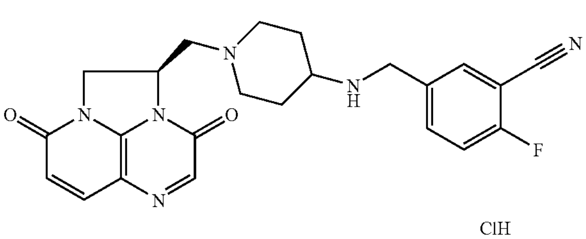 | 5-{[(1-{[(2R)-3,8-dioxo-1,2-dihydro-3H,8H-2a,5,8a-triazaacenaphthylen-2-yl]methyl}-4-piperidinyl)amino]methyl}-2-fluorobenzonitrile hydrochloride |

TABLE 1-continued

| | | |
|---|---|---|
| 6 | | (2R)-2-[(4-{[(4-fluoro-3-methylphenyl)methyl]amino}-1-piperidinyl)methyl]-1,2-dihydro-3H,8H-2a,5,8a-triazaacenaphthylene-3,8-dione hydrochloride |
| 7 | | (1R)-1-[(4-{[(5-chloro-4-methyl-2-pyridinyl)methyl]amino}-1-piperidinyl)methyl]-1,2-dihydro-4H,9H-imidazo[1,2,3-ij]-1,8-naphthyridine-4,9-dione hydrochloride |
| 8 | | (1R)-1-[(4-{[(5-chloro-6-methyl-3-pyridinyl)methyl]amino}-1-piperidinyl)methyl]-1,2-dihydro-3H,8H-2a,5,8a-triazaacenaphthylene-3,8-dione hydrochloride |
| 9 | | (1R)-1-{[4-({[6-(trifluoromethyl)-3-pyridinyl]methyl}amino)-1-piperidinyl]methyl}-1,2-dihydro-4H,9H-imidazo[1,2,3-ij]-1,8-naphthyridine-4,9-dione |
| 10 | | (1R)-1-[(4-{[(3,4-dichlorophenyl)methyl]amino}-1-piperidinyl)methyl]-1,2-dihydro-3H,8H-2a,5,8a-triazaacenaphthylene-3,8-dione |
| 11 | | (1R)-1-{[4-({[6-(trifluoromethyl)-3-pyridinyl]methyl}amino)-1-piperidinyl]methyl}-1,2-dihydro-3H,8H-2a,5,8a-triazaacenaphthylene-3,8-dione |

TABLE 1-continued

| | | |
|---|---|---|
| 12 | 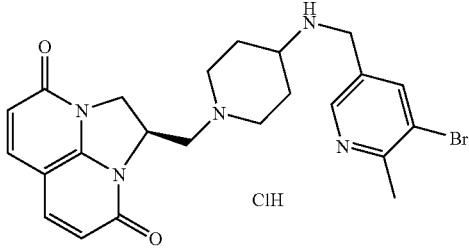 | (1R)-1-[(4-{[(5-bromo-6-methyl-3-pyridinyl)methyl]amino}-1-piperidinyl)methyl]-1,2-dihydro-4H,9H-imidazo[1,2,3-ij]-1,8-naphthyridine-4,9-dione hydrochloride |
| 13 | 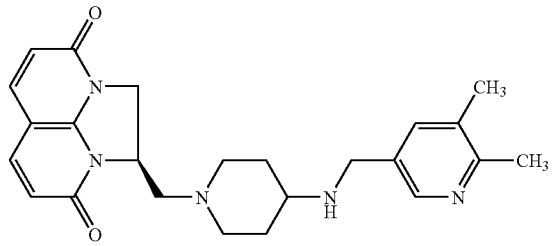 | (1R)-1-[(4-{[(5,6-dimethyl-3-pyridinyl)methyl]amino}-1-piperidinyl)methyl]-1,2-dihydro-4H,9H-imidazo[1,2,3-ij]-1,8-naphthyridine-4,9-dione |
| 14 | 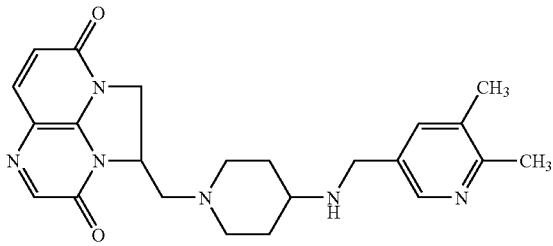 | 2-[(4-{[(5,6-dimethyl-3-pyridinyl)methyl]amino}-1-piperidinyl)methyl]-1,2-dihydro-3H,8H-2a,5,8a-triazaacenaphthylene-3,8-dione |
| 15 | 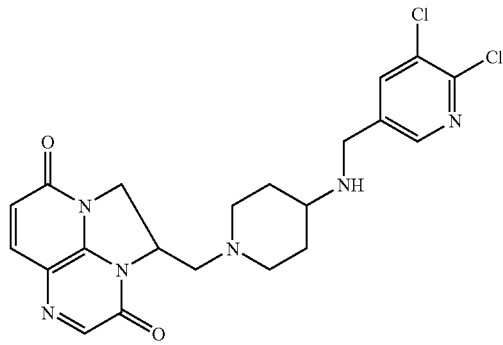 | 2-[(4-{[(5,6-dichloro-3-pyridinyl)methyl]amino}-1-piperidinyl)methyl]-1,2-dihydro-3H,8H-2a,5,8a-triazaacenaphthylene-3,8-dione |
| 16 | 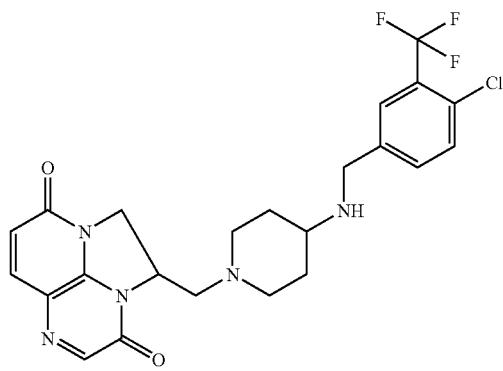 | 2-{[4-({[4-chloro-3-(trifluoromethyl)phenyl]methyl}amino)-1-piperidinyl]methyl}-1,2-dihydro-3H,8H-2a,5,8a-triazaacenaphthylene-3,8-dione |

TABLE 1-continued

| # | Structure | Name |
|---|---|---|
| 17 | 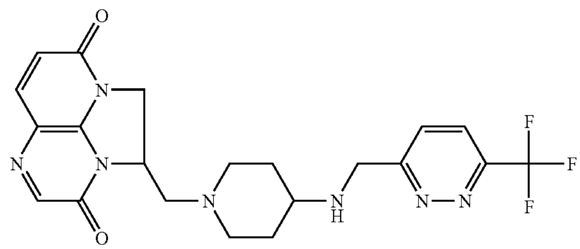 | 2-{[4-({[6-(trifluoromethyl)-3-pyridazinyl]methyl}amino)-1-piperidinyl]methyl}-1,2-dihydro-3H,8H-2a,5,8a-triazaacenaphthylene-3,8-dione |
| 18 | 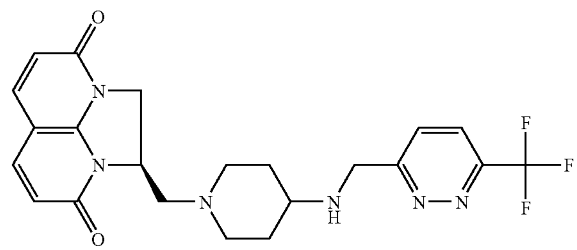 | (1R)-1-{[4-({[6-(trifluoromethyl)-3-pyridazinyl]methyl}amino)-1-piperidinyl]methyl}-1,2-dihydro-4H,9H-imidazo[1,2,3-ij]-1,8-naphthyridine-4,9-dione |
| 19 | Free base of 20 (below) | 2-{[4-({[6-(trifluoromethyl)-3-pyridinyl]methyl}amino)-1-piperidinyl]methyl}-1,2-dihydro-3H,8H-2a,5,8a-triazaacenaphthylene-3,8-dione |
| 20 | 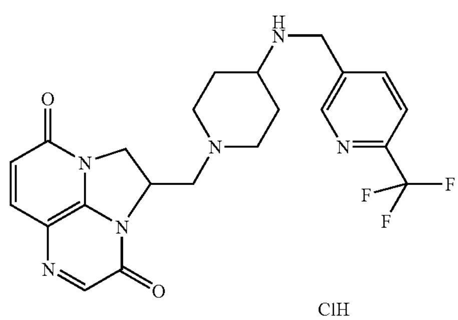 | 2-{[4-({[6-(trifluoromethyl)-3-pyridinyl]methyl}amino)-1-piperidinyl]methyl}-1,2-dihydro-3H,8H-2a,5,8a-triazaacenaphthylene-3,8-dione hydrochloride |
| 21 | 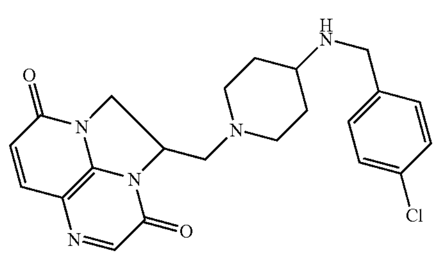 | 2-[(4-{[(4-chlorophenyl)methyl]amino}-1-piperidinyl)methyl]-1,2-dihydro-3H,8H-2a,5,8a-triazaacenaphthylene-3,8-dione |
| 22 | 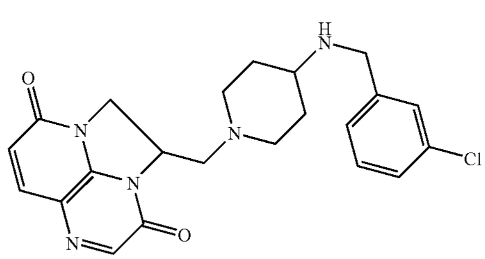 | 2-[(4-{[(3-chlorophenyl)methyl]amino}-1-piperidinyl)methyl]-1,2-dihydro-3H,8H-2a,5,8a-triazaacenaphthylene-3,8-dione |

TABLE 1-continued

| 23 | 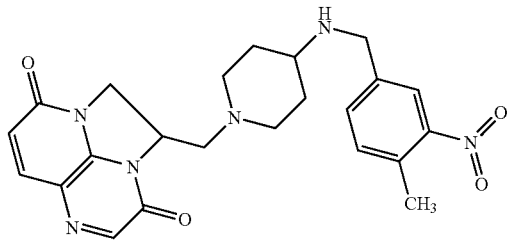 | 2-[(4-{[(4-methyl-3-nitrophenyl)methyl]amino}-1-piperidinyl)methyl]-1,2-dihydro-3H,8H-2a,5,8a-triazaacenaphthylene-3,8-dione |
| --- | --- | --- |
| 24 | 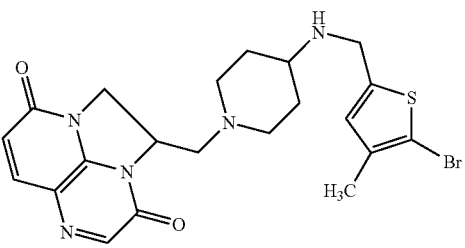 | 2-[(4-{[(5-bromo-4-methyl-2-thienyl)methyl]amino}-1-piperidinyl)methyl]-1,2-dihydro-3H,8H-2a,5,8a-triazaacenaphthylene-3,8-dione |
| 25 | 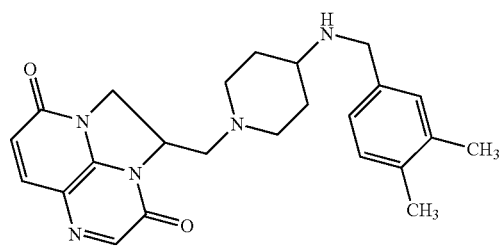 | 2-[(4-{[(3,4-dimethylphenyl)methyl]amino}-1-piperidinyl)methyl]-1,2-dihydro-3H,8H-2a,5,8a-triazaacenaphthylene-3,8-dione |
| 26 | 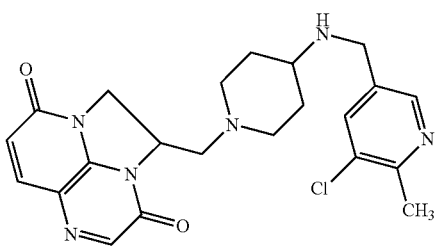 | 2-[(4-{[(5-chloro-6-methyl-3-pyridinyl)methyl]amino}-1-piperidinyl)methyl]-1,2-dihydro-3H,8H-2a,5,8a-triazaacenaphthylene-3,8-dione |
| 27 | 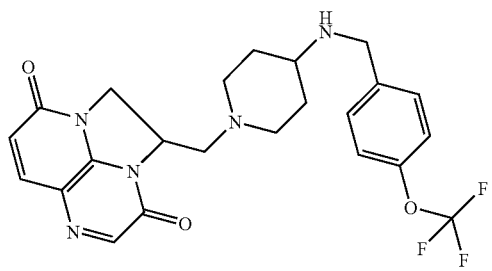 | 2-({4-[({4-[(trifluoromethyl)oxy]phenyl}methyl)amino]-1-piperidinyl}methyl)-1,2-dihydro-3H,8H-2a,5,8a-triazaacenaphthylene-3,8-dione |
| 28 | 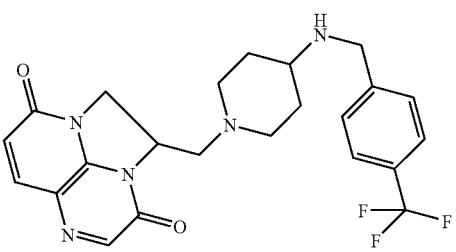 | 2-{[4-({[4-(trifluoromethyl)phenyl]methyl}amino)-1-piperidinyl]methyl}-1,2-dihydro-3H,8H-2a,5,8a-triazaacenaphthylene-3,8-dione |

TABLE 1-continued

| 29 | 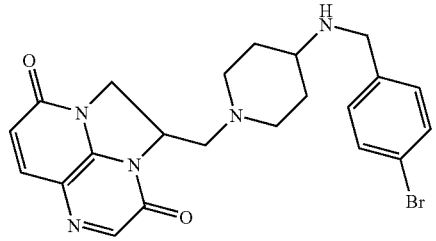 | 2-[(4-{[(4-bromophenyl)methyl]amino}-1-piperidinyl)methyl]-1,2-dihydro-3H,8H-2a,5,8a-triazaacenaphthylene-3,8-dione |
| --- | --- | --- |
| 30 | Hydrochloride of 26 above | 2-[(4-{[(5-chloro-6-methyl-3-pyridinyl)methyl]amino}-1-piperidinyl)methyl]-1,2-dihydro-3H,8H-2a,5,8a-triazaacenaphthylene-3,8-dione hydrochloride |
| 31 | 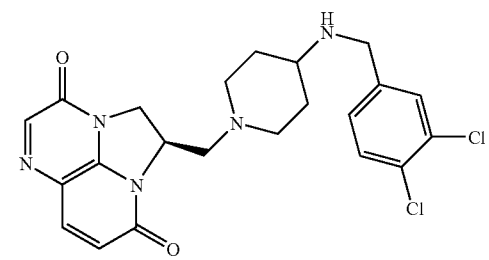 | (1R)-1-[(4-{[(3,4-dichlorophenyl)methyl]amino}-1-piperidinyl)methyl]-1,2-dihydro-4H,9H-imidazo[1,2,3-ij]-1,8-naphthyridine-4,9-dione hydrochloride |
| 32 | 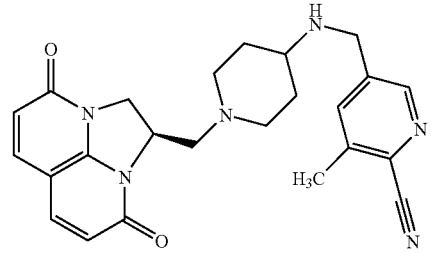 | 5-{[(1-{[(1R)-4,9-dioxo-1,2-dihydro-4H,9H-imidazo[1,2,3-ij]-1,8-naphthyridin-1-yl]methyl}-4-piperidinyl)amino]methyl}-3-methyl-2-pyridinecarbonitrile |
| 33 | 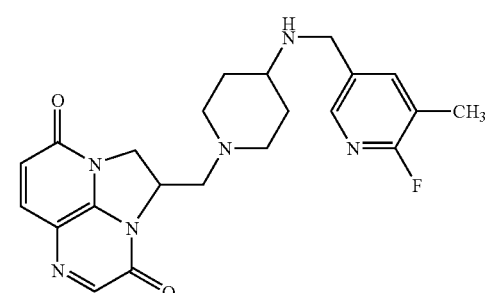 | 2-[(4-{[(6-fluoro-5-methyl-3-pyridinyl)methyl]amino}-1-piperidinyl)methyl]-1,2-dihydro-3H,8H-2a,5,8a-triazaacenaphthylene-3,8-dione |
| 34 | 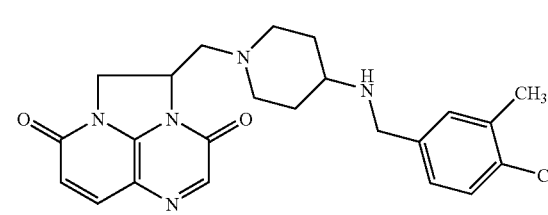 | 2-[(4-{[(4-chloro-3-methylphenyl)methyl]amino}-1-piperidinyl)methyl]-1,2-dihydro-3H,8H,2a,5,8a-triazaacenaphthylene-3,8-dione |

TABLE 1-continued

| | | | |
|---|---|---|---|
| 35 | 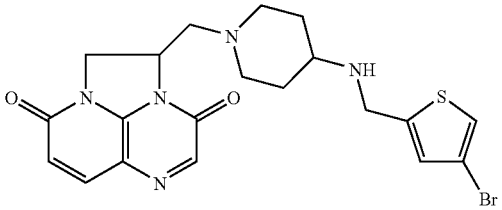 | | 2-[(4-{[(4-bromo-2-thienyl)methyl]amino}-1-piperidinyl)methyl]-1,2-dihydro-3H,8H-2a,5,8a-triazaacenaphthylene-3,8-dione |
| 36 | 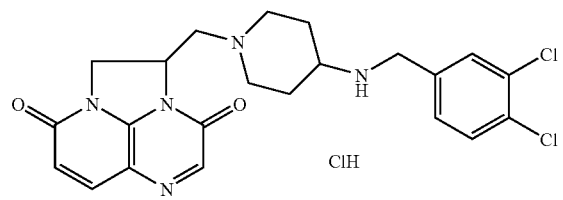 | ClH | 2-[(4-{[(3,4-dichlorophenyl)methyl]amino}-1-piperidinyl)methyl]-1,2-dihydro-3H,8H-2a,5,8a-triazaacenaphthylene-3,8-dione |
| 37 | 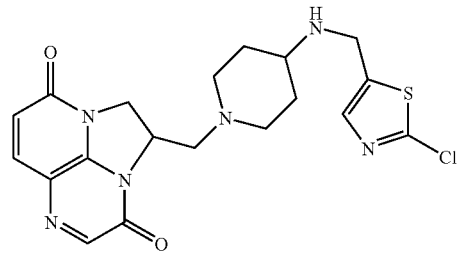 | | 2-[(4-{[(2-chloro-1,3-thiazol-5-yl)methyl]amino}-1-piperidinyl)methyl]-1,2-dihydro-3H,8H-2a,5,8a-triazaacenaphthylene-3,8-dione |
| 38 | 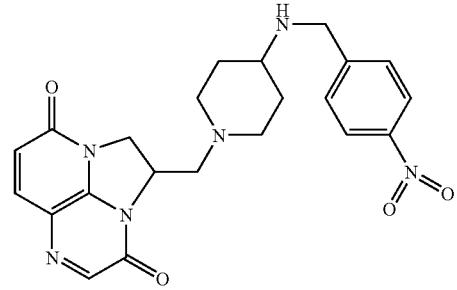 | | 2-[(4-{[(4-nitrophenyl)methyl]amino}-1-piperidinyl)methyl]-1,2-dihydro-3H,8H-2a,5,8a-triazaacenaphthylene-3,8-dione |
| 39 | 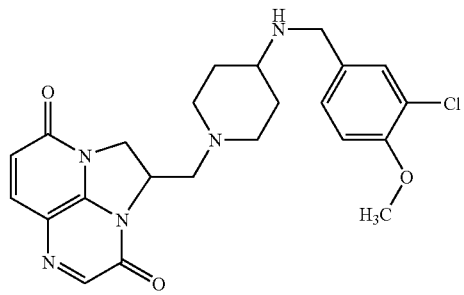 | | 2-{[4-({[3-chloro-4-(methyloxy)phenyl]methyl}amino)-1-piperidinyl]methyl}-1,2-dihydro-3H,8H-2a,5,8a-triazaacenaphthylene-3,8-dione |
| 40 | 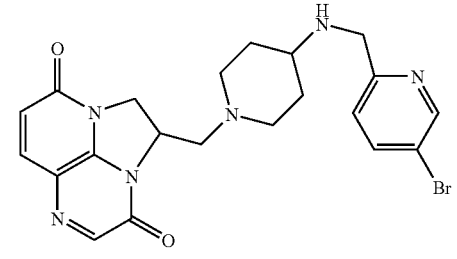 | | 2-[(4-{[(5-bromo-2-pyridinyl)methyl]amino}-1-piperidinyl)methyl]-1,2-dihydro-3H,8H-2a,5,8a-triazaacenaphthylene-3,8-dione |

TABLE 1-continued

| | | |
|---|---|---|
| 41 | | 2-[(4-{[(5-bromo-3-pyridinyl)methyl]amino}-1-piperidinyl)methyl]-1,2-dihydro-3H,8H-2a,5,8a-triazaacenaphthylene-3,8-dione |
| 42 | | 2-[(4-{[(5-chloro-3-pyridinyl)methyl]amino}-1-piperidinyl)methyl]-1,2-dihydro-3H,8H-2a,5,8a-triazaacenaphthylene-3,8-dione |
| 43 | | 2-[(4-{[(3-fluoro-4-methylphenyl)methyl]amino}-1-piperidinyl)methyl]-1,2-dihydro-3H,8H-2a,5,8a-triazaacenaphthylene-3,8-dione |
| 44 | | 2-[(4-{[(3,4-difluorophenyl)methyl]amino}-1-piperidinyl)methyl]-1,2-dihydro-3H,8H-2a,5,8a-triazaacenaphthylene-3,8-dione |
| 45 | | (2R)-2-{[4-({[6-(trifluoromethyl)-3-pyridinyl]methyl}amino)-1-piperidinyl]methyl}-1,2-dihydro-3H,8H-2a,5,8a-triazaacenaphthylene-3,8-dione |
| 46 | | (2R)-2-{[4-({[6-(trifluoromethyl)-3-pyridinyl]methyl}amino)-1-piperidinyl]methyl}-1,2-dihydro-3H,8H-2a,5,8a-triazaacenaphthylene-3,8-dione hydrochloride |

TABLE 1-continued

| | | |
|---|---|---|
| 47 | 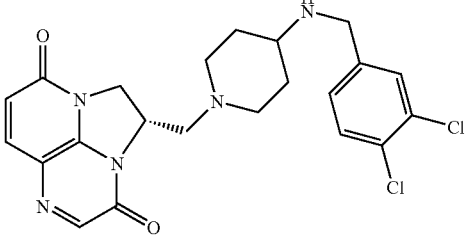 | (2S)-2-[(4-{[(3,4-dichlorophenyl)methyl]amino}-1-piperidinyl)methyl]-1,2-dihydro-3H,8H-2a,5,8a-triazaacenaphthylene-3,8-dione |
| 48 | 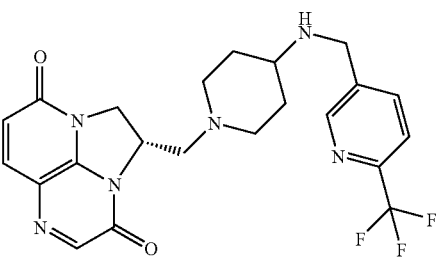 | (2S)-2-{[4-({[6-(trifluoromethyl)-3-pyridinyl]methyl}amino)-1-piperidinyl]methyl}-1,2-dihydro-3H,8H-2a,5,8a-triazaacenaphthylene-3,8-dione |
| 49 | 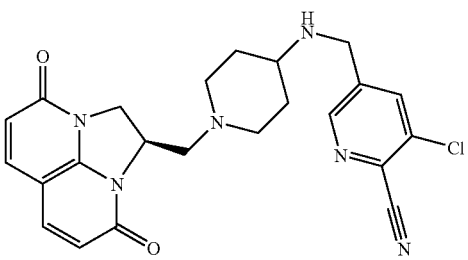 | 3-chloro-5-{[(1-{[(1R)-4,9-dioxo-1,2-dihydro-4H,9H-imidazo[1,2,3-ij]-1,8-naphthyridin-1-yl]methyl}-4-piperidinyl)amino]methyl}-2-pyridinecarbonitrile |
| 50 | 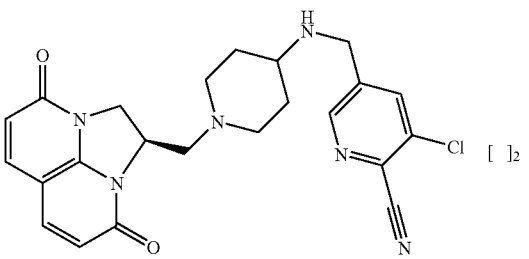 | 3-chloro-5-{[(1-{[(1R)-4,9-dioxo-1,2-dihydro-4H,9H-imidazo[1,2,3-ij]-1,8-naphthyridin-1-yl]methyl}-4-piperidinyl)amino]methyl}-2-pyridinecarbonitrile dihydrochloride |
| 51 | 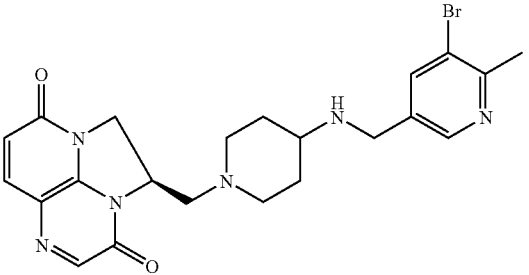 | (2R)-2-[(4-{[(5-bromo-6-methyl-3-pyridinyl)methyl]amino}-1-piperidinyl)methyl]-1,2-dihydro-3H,8H-2a,5,8a-triazaacenaphthylene-3,8-dione hydrochloride |

TABLE 1-continued

| 52 | 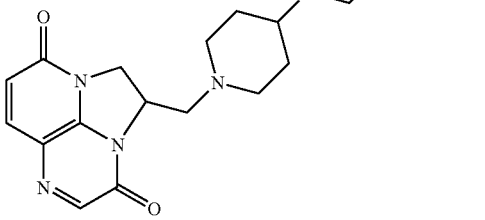 | 2-[(4-{[(5-fluoro-6-methyl-3-pyridinyl)methyl]amino}-1-piperidinyl)methyl]-1,2-dihydro-3H,8H-2a,5,8a-triazaacenaphthylene-3,8-dione |
| 53 | 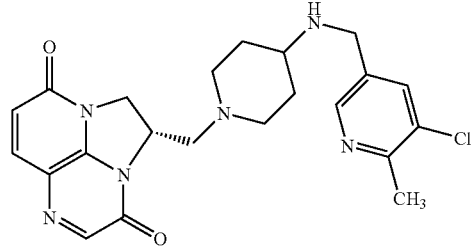 | (2S)-2-[(4-{[(5-chloro-6-methyl-3-pyridinyl)methyl]amino}-1-piperidinyl)methyl]-1,2-dihydro-3H,8H-2a,5,8a-triazaacenaphthylene-3,8-dione |
| 54 | 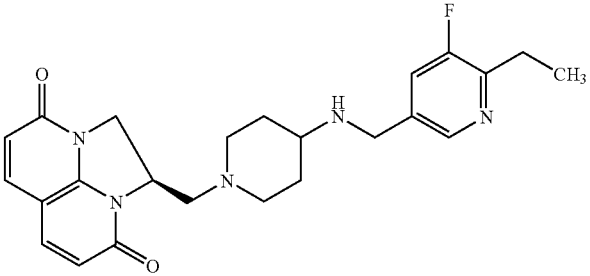 | (1R)-1-[(4-{[(6-ethyl-5-fluoro-3-pyridinyl)methyl]amino}-1-piperidinyl)methyl]-1,2-dihydro-4H,9H-imidazo[1,2,3-ij]-1,8-naphthyridine-4,9-dione |
| 55 | 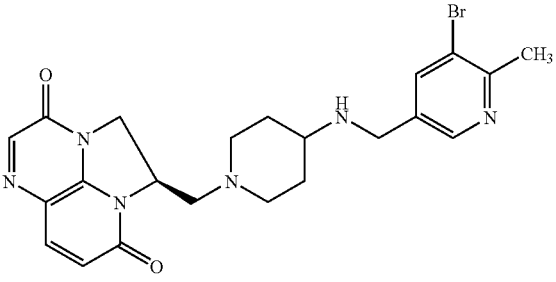 | (1R)-1-[(4-{[(5-bromo-6-methyl-3-pyridinyl)methyl]amino}-1-piperidinyl)methyl]-1,2-dihydro-3H,8H-2a,5,8a-triazaacenaphthylene-3,8-dione hydrochloride |
| 56 | 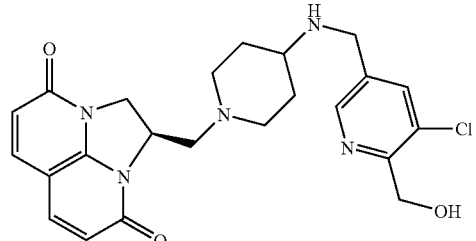 | (1R)-1-{[4-({[5-chloro-6-(hydroxymethyl)-3-pyridinyl]methyl}amino)-1-piperidinyl]methyl}-1,2-dihydro-4H,9H-imidazo[1,2,3-ij]-1,8-naphthyridine-4,9-dione |

TABLE 1-continued

| 57 | 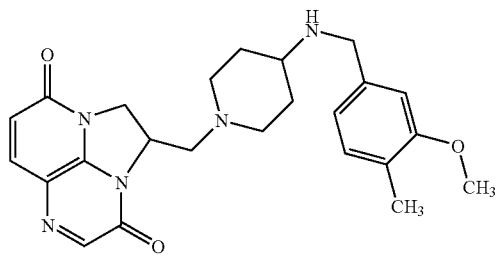 | 2-{[4-({[4-methyl-3-(methyloxy)phenyl]methyl}amino)-1-piperidinyl]methyl}-1,2-dihydro-3H,8H-2a,5,8a-triazaacenaphthylene-3,8-dione |
| --- | --- | --- |
| 58 | 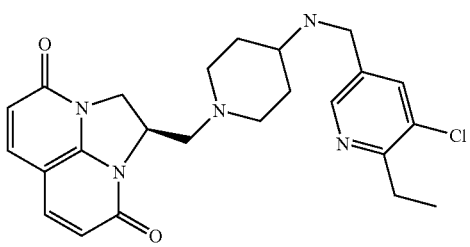 | (1R)-1-[(4-{[(5-chloro-6-ethyl-3-pyridinyl)methyl]amino}-1-piperidinyl)methyl]-1,2-dihydro-4H,9H-imidazo[1,2,3-ij]-1,8-naphthyridine-4,9-dione |
| 59 | 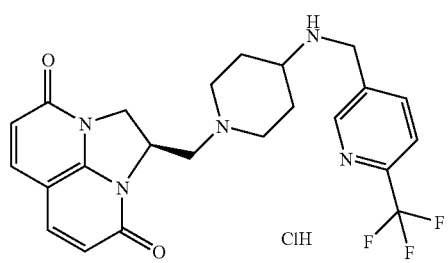 | (1R)-1-{[4-({[6-(trifluoromethyl)-3-pyridinyl]methyl}amino)-1-piperidinyl]methyl}-1,2-dihydro-4H,9H-imidazo[1,2,3-ij]-1,8-naphthyridine-4,9-dione hydrochloride. (hydrochloride salt of Example 9 compound) |
| 60 | 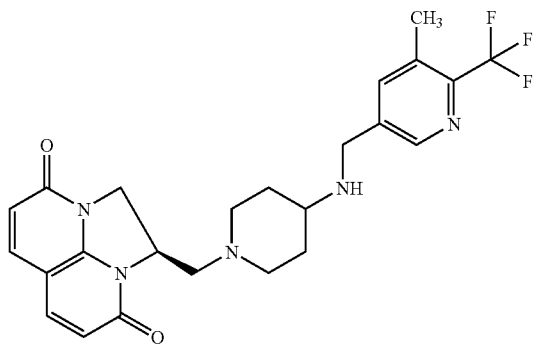 | (1R)-1-{[4-({[5-methyl-6-(trifluoromethyl)-3-pyridinyl]methyl}amino)-1-piperidinyl]methyl}-1,2-dihydro-4H,9H-imidazo[1,2,3-ij]-1,8-naphthyridine-4,9-dione |
| 61 | 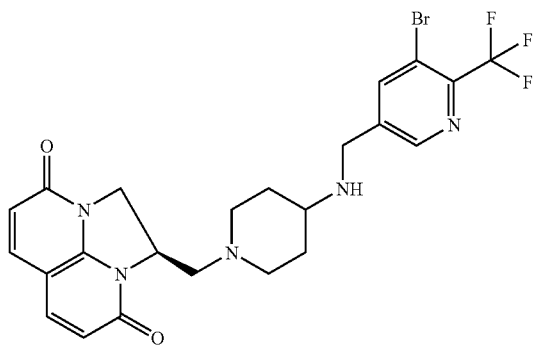 | (1R)-1-{[4-({[5-bromo-6-(trifluoromethyl)-3-pyridinyl]methyl}amino)-1-piperidinyl]methyl}-1,2-dihydro-4H,9H-imidazo[1,2,3-ij]-1,8-naphthyridine-4,9-dione |

TABLE 1-continued

| | | |
|---|---|---|
| 62 | 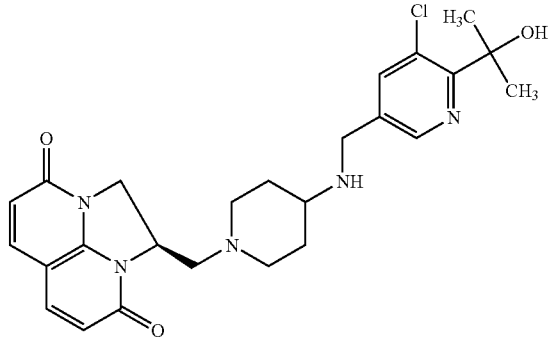 | (1R)-1-{[4-({[5-chloro-6-(1-hydroxy-1-methylethyl)-3-pyridinyl]methyl}amino)-1-piperidinyl]methyl}-1,2-dihydro-4H,9H-imidazo[1,2,3-ij]-1,8-naphthyridine-4,9-dione |
| 63 | 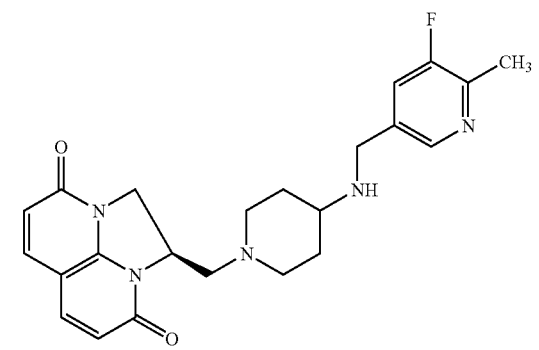 | (1R)-1-[(4-{[(5-fluoro-6-methyl-3-pyridinyl)methyl]amino}-1-piperidinyl)methyl]-1,2-dihydro-4H,9H-imidazo[1,2,3-ij]-1,8-naphthyridine-4,9-dione |
| 64 | 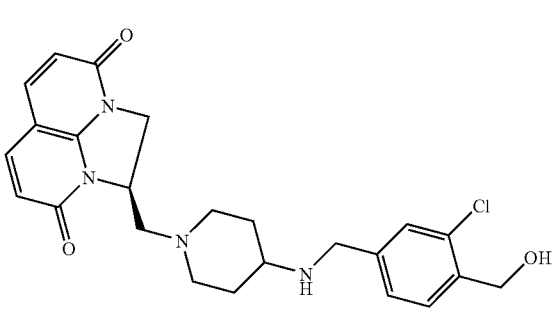 | (1R)-1-{[4-({[3-chloro-4-(hydroxymethyl)phenyl]methyl}amino)-1-piperidinyl]methyl}-1,2-dihydro-4H,9H-imidazo[1,2,3-ij]-1,8-naphthyridine-4,9-dione |
| 65 | 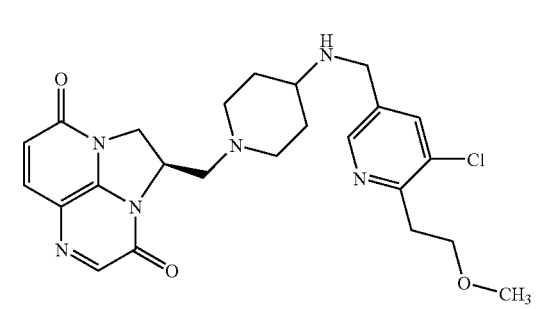 | (2R)-2-({4-[({5-chloro-6-[2-(methyloxy)ethyl]-3-pyridinyl}methyl)amino]-1-piperidinyl}methyl)-1,2-dihydro-3H,8H-2a,5,8a-triazaacenaphthylene-3,8-dione |
| 66 | 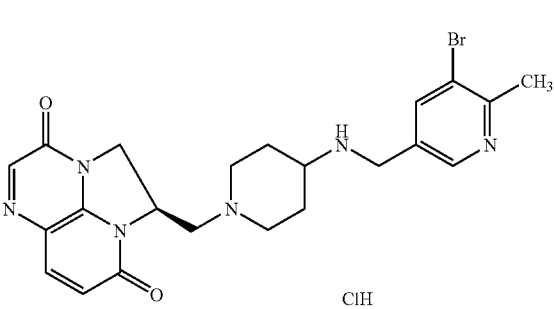 | (1R)-1-[(4-{[(5-bromo-6-methyl-3-pyridinyl)methyl]amino}-1-piperidinyl)methyl]-1,2-dihydro-3H,8H-2a,5,8a-triazaacenaphthylene-3,8-dione hydrochloride |

TABLE 1-continued

| | | | |
|---|---|---|---|
| 67 | 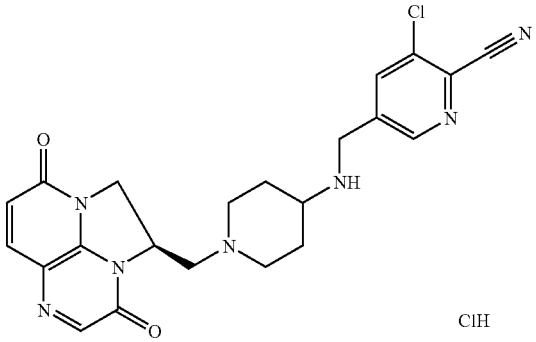 ClH | [ ]2 | 3-chloro-5-{[(1-{[(2R)-3,8-dioxo-1,2-dihydro-3H,8H-2a,5,8a-triazaacenaphthylen-2-yl]methyl}-4-piperidinyl)amino]methyl}-2-pyridine carbonitrile dihydrochloride |
| 68 | 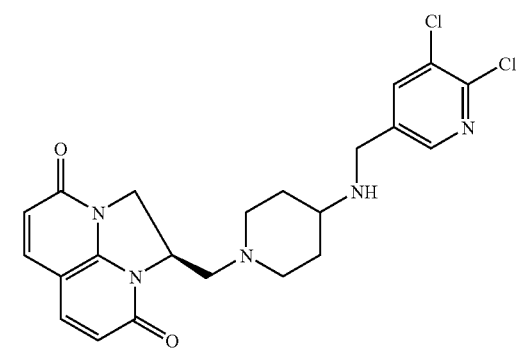 ClH | | (1R)-1-[(4-{[(5,6-dichloro-3-pyridinyl)methyl]amino}-1-piperidinyl)methyl]-1,2-dihydro-4H,9H-imidazo[1,2,3-ij]-1,8-naphthyridine-4,9-dione |
| 69 | 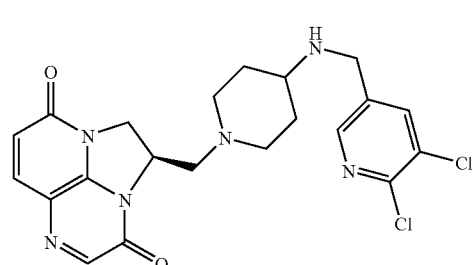 | | (2R)-2-[(4-{[(5,6-dichloro-3-pyridinyl)methyl]amino}-1-piperidinyl)methyl]-1,2-dihydro-3H,8H-2a,5,8a-triazaacenaphthylene-3,8-dione |
| 70 | 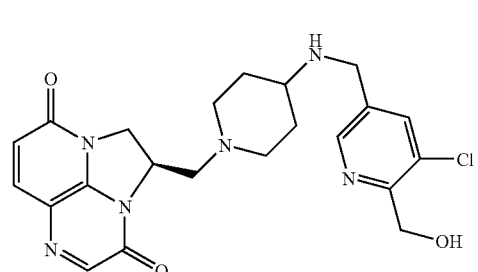 | | (2R)-2-{[4-({[5-chloro-6-(hydroxymethyl)-3-pyridinyl]methyl}amino)-1-piperidinyl]methyl}-1,2-dihydro-3H,8H2a,5,8a-triazaacenaphthylene-3,8-dione |
| 71 | 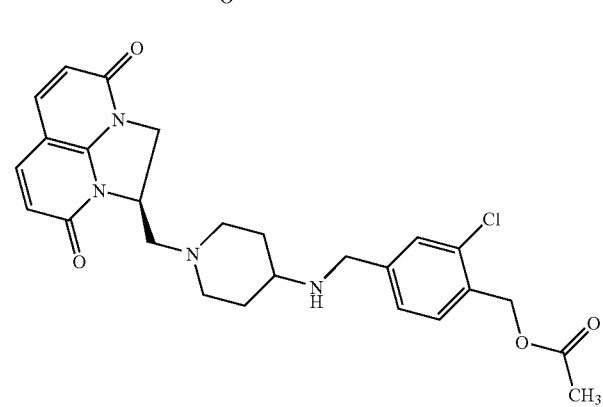 | | (2-chloro-4-{[(1-{[(1R)-4,9-dioxo-1,2-dihydro-4H,9H-imidazo[1,2,3-ij]-1,8-naphthyridin-1-yl]methyl}-4-piperidinyl)amino]methyl}phenyl) methyl acetate |

TABLE 1-continued

| | | |
|---|---|---|
| 72 | 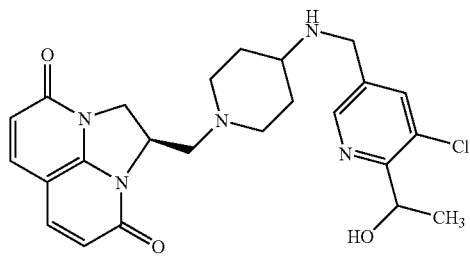 | (1R)-1-{[4-({[5-chloro-6-(1-hydroxyethyl)-3-pyridinyl]methyl}amino)-1-piperidinyl]methyl}-1,2-dihydro-4H,9H-imidazo[1,2,3-ij]-1,8-naphthyridine-4,9-dione |
| 73 | 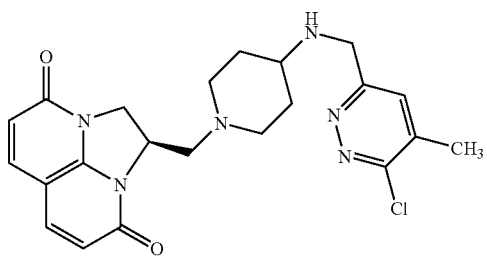 | (1R)-1-[(4-{[(6-chloro-5-methyl-3-pyridazinyl)methyl]amino}-1-piperidinyl)methyl]-1,2-dihydro-4H,9H-imidazo[1,2,3-ij]-1,8-naphthyridine-4,9-dione |
| 74 | 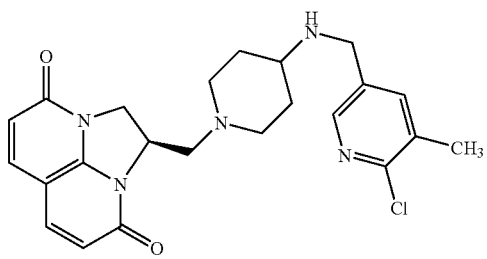 | (1R)-1-[(4-{[(6-chloro-5-methyl-3-pyridinyl)methyl]amino}-1-piperidinyl)methyl]-1,2-dihydro-4H,9H-imidazo[1,2,3-ij]-1,8-naphthyridine-4,9-dione |
| 75 | 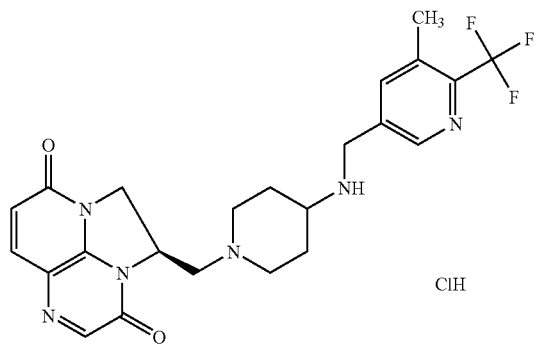 | (2R)-2-{[4-({[5-methyl-6-(trifluoromethyl)-3-pyridinyl]methyl}amino)-1-piperidinyl]methyl}-1,2-dihydro-3H,8H-2a,5,8a-triazaacenaphthylene-3,8-dione hydrochloride |

| Ex | Physical data | Method analogous to which Scheme. (amine confign.) | Starting compound of Formula (IIB) W-UR[5] and source | MtB MIC μg/ml |
|---|---|---|---|---|

TABLE 1-continued

| | | | | |
|---|---|---|---|---|
| 1 & 1A | ¹H-NMR (δ, ppm, CDCl₃ + CD₃OD): 8.33 (d, 1 H); 8.05 (d, 1 H); 7.53 (d, 1 H); 7.52 (d, 1 H); 6.28 (d, 1 H); 6.24 (d, 1 H); 5.05-4.93 (m, 1 H); 4.48 (dd, 1 H); 4.35 (dd, 1 H); 3.99 (s, 2 H); 3.07 (dd, 1 H); 3.03-2.78 (m, 2 H); 2.77-2.62 (m, 2 H); 2.58 (s, 3 H); 2.37-2.17 (m, 2 H); 2.12-1.97 (m, 2 H); 1.70-1.46 (m, 2 H). [ES MS] m/z 440 (MH⁺). | Scheme 3 (2N) | 5-chloro-6-methyl-3-pyridinecarbaldehyde WO20006/137485 A1 | 0.04 |
| 2 | ¹H-NMR (δ, ppm, CDCl₃ + CD₃OD): 8.36 (d, 1 H); 8.10 (d, 1 H); 7.79 (s, 1 H); 7.77 (d, 1 H); 6.35 (d, 1 H); 5.07-4.97 (m, 1 H); 4.45 (dd, 1 H); 4.39 (dd, 1 H); 4.04 (s, 2 H); 3.15 (dd, 1 H); 3.10-3.00 (m, 1 H); 2.84-2.75 (m, 1 H); 2.68 (dd, 2 H); 2.59 (s, 3 H); 2.39-2.18 (m, 2 H); 2.15-2.01 (m, 2 H); 1.77-1.59 (m, 2 H). [ES MS] m/z 441 (MH⁺). | Scheme 1 (3N-r) | 5-chloro-6-methyl-3-pyridinecarbaldehyde WO20006/137485 A1 | 0.04 |
| 3 | ¹H-NMR (δ, ppm, CDCl₃): 7.83 (s, 1 H); 7.77 (d, 1 H); 7.44-7.43 (m, 1 H); 7.38 (d, 1 H); 7.17-7.14 (m, 1 H); 6.39 (d, 1 H); 5.06-4.99 (m, 1 H); 4.55 (dd, 1 H); 4.38 (dd, 1 H); 3.75 (s, 2 H); 3.14 (dd, 1 H); 2.96-2.90 (m, 1 H); 2.72-2.64 (m, 2 H); 2.53-2.44 (m, 1 H); 2.36-2.30 (m, 1 H); 2.27-2.21 (m, 1 H); 1.89-1.78 (m, 2 H); 1.39-1.25 (m, 2 H). [ES MS] m/z 460 (MH⁺). | Scheme 1 (3N-r) | 3,4-dichlorobenzaldehyde Fluka 35270 | 0.04 |
| 4 | ¹H-NMR (δ, ppm, CDCl₃): 7.82 (s, 1 H); 7.77 (d, 1 H); 7.57 (d, 1 H); 7.53-7.49 (m, 1 H); 7.16-7.11 (m, 1 H); 6.38 (d, 1 H); 5.06-5.00 (m, 1 H); 4.57-4.52 (m, 1 H); 4.38 (dd, 1 H); 3.80 (s, 2 H); 3.14 (dd, 1 H); 2.95-2.92 (m, 1 H); 2.72-2.66 (m, 2 H); 2.52-2.47 (m, 1 H); 2.37-2.30 (m, 1 H); 2.28-2.22 (m, 1 H); 1.88-1.81 (m, 2 H); 1.39-1.25 (m, 2 H). [ES MS] m/z 478 (MH⁺). | Scheme 1 (3N-r) | 4-fluoro-3-(trifluoromethyl)benzaldehyde Aldrich 469335 | 0.04 |

TABLE 1-continued

| | | | | |
|---|---|---|---|---|
| 5 | ¹H-NMR (δ, ppm, CDCl₃): 7.84 (s, 1 H); 7.78 (d, 1 H); 7.64-7.55 (m, 2 H); 7.20-7.13 (m, 1 H); 6.40 (d, 1 H); 5.09-4.99 (m, 1 H); 4.57 (dd, 1 H); 4.39 (dd, 1 H); 3.80 (s, 2 H); 3.16 (dd, 1 H); 2.99-2.90 (m, 1 H); 2.75-2.64 (m, 2 H); 2.53-2.44 (m, 1 H); 2.39-2.20 (m, 2 H); 1.91-1.78 (m, 2 H); 1.41-1.25 (m, 2 H). [ES MS] m/z 435 (MH⁺). | Scheme 1 (3N-r) | 2-fluoro-5-formylbenzonitrile Aldrich 494089 | 0.11 |
| 6 | ¹H-NMR (δ, ppm, CDCl₃): 7.80 (s, 1 H); 7.75 (d, 1 H); 7.18-7.06 (m, 2 H); 6.98-6.89 (m, 1 H); 6.36 (d, 1 H), 5.07-4.96 (m, 1 H); 4.59-4.49 (m, 2 H); 4.37 (dd, 1 H); 3.72 (s, 2 H); 3.12 (dd, 1 H); 2.96-2.91 (m, 1 H); 2.73-2.64 (m, 2 H); 2.58-2.47 (m, 1 H); 2.36-2.17 (m, 4 H); 1.90-1.81 (m, 2 H); 1.47-1.31 (m, 2 H). [ES MS] m/z 424 (MH⁺). | Scheme 1 (3N-r) | 4-fluoro-3 methylbenzaldehyde Aldrich 515132 | 0.29 |
| 7 | ¹H-NMR (δ, ppm, CD₃OD): 8.38 (s, 1 H); 7.73-7.71 (m, 2 H); 7.33 (s, 1 H); 6.27-6.21 (m, 2 H); 5.08-5.02 (m, 1 H); 4.45-4.36 (m, 2 H); 3.87 (s, 2 H); 3.01-2.95 (m, 2 H); 2.86-2.81 (m, 1 H); 2.62-2.50 (m, 2 H); 2.37 (s, 3 H); 2.26-2.16 (m, 2 H); 1.90-1.80 (m, 2 H); 1.43-1.22 (m, 2 H). [ES MS] m/z 440 (MH⁺). | Scheme 3 (2N) | 5-chloro-4-methyl-2-pyridinecarbaldehyde Anichem P20471 | 0.30 |
| 8 | ¹H-NMR (δ, ppm, CDCl₃ + CD₃OD): 8.32 (d, 1 H); 8.06 (d, 1 H); 7.80 (s, 1 H); 7.74 (d, 1 H); 6.29 (d, 1 H); 5.05-4.92 (m, 1 H); 4.47 (dd, 1 H); 4.40 (dd, 1 H); 4.01 (s, 2 H); 3.10 (dd, 1 H); 3.08-2.97 (m, 1 H); 2.97-2.84 (dd, 1 H); 2.80-2.60 (m, 2 H); 2.56 (s, 3 H); 2.38-2.16 (m, 2 H); 2.12-1.96 (m, 2 H); 1.74-1.53 (m, 2 H). [ES MS] m/z 441 (MH⁺). | Scheme 2 (3N-l) | 5-chloro-6-methyl-3-pyridinecarbaldehyde WO20006/137485 A1 | 0.08 |

TABLE 1-continued

| | | | | |
|---|---|---|---|---|
| 9 | $^1$H-NMR (δ, ppm, CDCl$_3$): 8.67 (bs, 1 H); 7.89 (bd, 1 H); 7.66 (d, 1 H); 7.51 (d, 1 H); 7.50 (d, 1 H); 6.32 (d, 1 H); 6.26 (d, 1 H); 5.07-4.96 (m, 1 H); 4.58 (dd, 1 H); 4.36 (dd, 1 H); 3.90 (s, 2 H); 3.11 (dd, 1 H); 3.01-2.90 (m, 1 H); 2.68 (dd, 1 H); 2.55-2.43 (m, 1 H); 2.55-2.43 (m, 1 H); 2.37-2.16 (m, 2 H); 1.92-1.76 (m, 2 H); 1.39-1.18 (m, 2 H). [ES MS] m/z 460 (MH$^+$). | Scheme 3 (2N) | 6-(trifluoromethyl)-3-pyridinecarbaldehyde Fluorochem 009397 | 0.14 |
| 10 | $^1$H-NMR (δ, ppm, CDCl$_3$): 7.88 (s, 1 H); 7.76 (d, 1 H); 7.44 (d, 1 H); 7.39 (d, 1 H); 7.16 (dd, 1 H); 6.35 (d, 1 H); 5.07-4.96 (m, 1 H); 4.60 (dd, 1 H); 4.40 (dd, 1 H); 3.75 (s, 2 H); 3.12 (dd, 1 H); 2.97-2.88 (m, 1 H); 2.72 (dd, 1 H); 2.67-2.58 (m, 1 H); 2.53-2.41 (m, 1 H); 2.38-2.20 (m, 2 H); 1.90-1.74 (m, 2 H); 1.40-1.20 (m, 2 H). [ES MS] m/z 461 (MH$^+$). | Scheme 2 (3N-1) | 3,4-dichlorobenzaldehyde Fluka 35270 | <0.02 |
| 11 | $^1$H-NMR (δ, ppm, CDCl$_3$): 8.67 (s, 1 H); 7.93-7.84 (m, 2 H); 7.77 (d, 1 H); 7.66 (d, 1 H); 6.35 (d, 1 H); 5.09-4.96 (m, 1 H); 4.60 (dd, 1 H); 4.41 (dd, 1 H); 3.90 (s, 2 H); 3.13 (dd, 1 H); 2.99-2.86 (m, 1 H); 2.73 (dd, 1 H); 2.69-2.58 (m, 1 H); 2.56-2.43 (m, 1 H); 2.39-2.19 (m, 2 H); 1.93-1.76 (m, 2 H); 1.42-1.20 (m, 2 H). [ES MS] m/z 461 (MH$^+$). | Scheme 2 (3N-l) | 6-(trifluoromethyl)-3-pyridinecarbaldehyde Fluorochem 009397 | 0.14 |
| 12 | $^1$H-NMR (δ, ppm, DMSO-d$_6$): 8.40 (s, 1 H), 8.01 (s, 1 H), 7.72 (d, 2 H), 6.12 (t, 2 H), 5.01-4.89 (m, 1 H), 4.35-4.19 (m, 2 H), 3.80 (bs, 2 H), 2.89 (bd, 2 H), 2.76 (bt, 1 H), 2.54 (s, 3 H), 2.52-2.41 (m, 2 H), 2.21-1.98 (m, 2 H), 1.78 (bt, 2 H), 1.35-1.09 (m, 2 H). [ES MS] m/z 484 (MH$^+$). | Scheme 3 (2N) | 5-bromo-6-methyl-3-pyridinecarbaldehyde (Preparation 7 above) | <0.019 |

TABLE 1-continued

| | | | | |
|---|---|---|---|---|
| 13 | $^1$H-NMR (δ, ppm, CDCl$_3$): 8.23 (d, 1 H); 7.51 (d, 1 H); 7.48 (d, 1 H); 7.39 (d, 1 H); 6.31 (d, 1 H); 6.25 (d, 1 H); 5.05-4.97 (m, 1 H); 4.58 (dd, 1 H); 4.36 (dd, 1 H); 3.73 (s, 2 H); 3.09 (dd, 1 H); 2.99-2.92 (m, 1 H); 2.71-2.61 (m, 2 H); 2.52-2.44 (m, 1 H); 2.48 (s, 3 H); 2.35-2.19 (m, 2 H); 2.28 (s, 3 H); 1.90-1.76 (m, 2 H); 1.41-1.28 (m, 2 H). [ES MS] m/z 420 (MH$^+$). | Scheme 3 (2N) | 5,6-dimethyl-3-pyridinecarbaldehyde (Preparation 9 above) | 1.049 |
| 14 | $^1$H-NMR (δ, ppm, CDCl$_3$): 8.23 (d, 1 H); 7.83 (s, 1 H); 7.77 (d 1 H); 7.40 (d, 1 H); 6.39 (d, 1 H); 5.08-4.99 (m, 1 H); 4.56 (dd, 1 H); 4.3 8 (dd, 1 H); 3.74 (s, 2 H); 3.14 (dd, 1 H); 2.97-2.91 (m, 1 H); 2.74-2.64 (m, 2 H); 2.54-2.50 (m, 1 H); 2.48 (s, 3 H); 2.38-2.21 (m, 2 H); 2.28 (s, 3 H); 1.91-1.79 (m, 2 H); 1.41-1.30 (m, 2 H). [ES MS] m/z 421 (MH$^+$). | Scheme 1 (3N-r) | 5,6-dimethyl-3-pyridinecarbaldehyde (Preparation 9 above) | 2.103 |
| 15 | $^1$H-NMR (δ, ppm, CDCl$_3$): 8.23 (d, 1 H); 7.82 (d, 1 H); 7.78 (d, 1 H); 7.77 (d, 1 H); 6.40 (d, 1 H); 5.08-4.99 (m, 1 H); 4.56 (dd, 1 H); 4.39 (dd, 1 H); 3.80 (s, 2 H); 3.15 (dd, 1 H); 2.97-2.91 (m, 1 H); 2.74-2.66 (m, 2 H); 2.53-2.44 (m, 1 H); 2.38-2.21 (m, 2 H); 1.90-1.79 (m, 2 H); 1.38-1.24 (m, 2 H). [ES MS] m/z 461 (MH$^+$). | Scheme 1 (3N-r) | 5,6-dichloro-3-pyridinecarbaldehyde (Preparation 2 above) | <0.018 |
| 16 | $^1$H-NMR (δ, ppm, CDCl$_3$): 7.84 (s, 1 H); 7.78 (d, 1 H); 7.66 (b s, 1 H); 7.45 (d, 2 H); 6.40 (d, 1 H); 5.08-4.99 (m, 1 H); 4.56 (dd, 1 H); 4.39 (dd, 1 H); 3.82 (s, 2 H); 3.15 (dd, 1 H); 2.97-2.91 (m, 1 H); 2.74-2.65 (m, 2 H); 2.54-2.44 (m, 1 H); 2.39-2.21 (m, 2 H); 1.90-1.80 (m, 2 H); 1.37-1.26 (m, 2 H). [ES MS] m/z 494 (MH$^+$). | Scheme 1 (3N-r) | 4-chloro-3-(trifluoromethyl)benzaldehyde Aldrich 481785 | 0.077 |

TABLE 1-continued

| | | | | |
|---|---|---|---|---|
| 17 | ¹H-NMR (δ, ppm, CDCl₃): 7.84-7.75 (m, 4 H); 6.39 (d, 1 H); 5.08-4.99 (m, 1 H); 4.56 (dd, 1 H); 4.39 (dd, 1 H); 4.24 (s, 2 H); 3.16 (dd, 1 H); 2.97-2.91 (m, 1 H); 2.74-2.65 (m, 2 H); 2.61-2.51 (m, 1 H); 2.39-2.22 (m, 2 H); 1.93-1.82 (m, 2 H); 1.43-1.33 (m, 2 H). [ES MS] m/z 462 (MH⁺). | Scheme 1 (3N-r) | 3-(bromomethyl)-6-(trifluoromethyl)pyridazine (See Preparation 1 above) | 0.865 |
| 18 | ¹H-NMR (δ, ppm, CDCl₃): 7.83 (d, 1 H); 7.79 (d, 1 H); 7.51 (d, 1 H); 7.48 (d, 1 H); 6.31 (d, 1 H); 6.26 (d, 1 H); 5.06-4.97 (m, 1 H); 4.59 (dd, 1 H); 4.36 (dd, 1 H); 4.24 (s, 2 H); 3.12 (dd, 1 H); 3.00-2.93 (m, 1 H); 2.71-2.63 (m, 2 H); 2.59-2.49 (m, 3 H); 2.36-2.20 (m, 2 H); 1.92-1.80 (m, 2 H); 1.43-1.26 (m, 2 H). [ES MS] m/z 461 (MH⁺). | Scheme 3 (2N) | 3-(bromomethyl)-6-(trifluoromethyl)pyridazine (See Preparation 1 above) | 0.432 |
| 19 | ¹H-NMR (δ, ppm, DMSO-d₆): 8.68 (s, 1 H); 8.02-7.99 (m, 1 H); 7.85 (m, 2 H); 7.72 (s, 1 H); 6.24 (d, 1 H); 5.05-4.96 (m, 1 H); 4.34-4.19 (m, 2 H); 3.80 (s, 2 H); 2.96-2.85 (m, 2 H); 2.80-2.73 (m, 1 H); 2.60-2.53 (m, 1 H); 2.35-2.24 (m, 1 H); 2.20-2.12 (m, 1 H); 2.07-1.99 (m, 1 H); 1.78-1.69 (m, 2 H); 1.22-1.13 (m, 2 H). [ES MS] m/z 461 (MH⁺). | Scheme 1 (3N-r) | 6-(trifluoromethyl)-3-pyridinecarbaldehyde Fluorochem 009397 | |
| 20 | ¹H-NMR (δ, ppm, DMSO-d₆): 9.45-9.14 (m, 1 H); 8.87 (s, 1 H); 8.26-8.23 (m, 1 H); 8.00-7.97 (d, 1 H); 7.85 (d, 1 H); 7.73 (s, 1 H); 6.24 (d, 1 H); 5.08-4.99 (m, 1 H); 4.36-4.20 (m, 4 H); 3.04-2.96 (m, 3 H); 2.85-2.78 (m, 1 H); 2.74-2.69 (m, 1 H); 2.25-2.07 (m, 2 H); 2.03-1.92 (m, 2 H); 1.54-1.42 (m, 2 H). [ES MS] m/z 461 (MH⁺). | Scheme 1 (3N-r) | 6-(trifluoromethyl)-3-pyridinecarbaldehyde Fluorochem 009397 | 0.311 |

TABLE 1-continued

| | | | | | |
|---|---|---|---|---|---|
| 21 | ¹H-NMR (δ, ppm, DMSO-d₆): 7.83 (d, 1 H); 7.71 (s, 1 H); 7.33 (s, 4 H); 6.24 (d, 1 H); 5.03-4.98 (m, 1 H); 4.34-4.20 (m, 2 H); 3.66 (s, 2 H); 2.96-2.87 (m, 2 H); 2.80-2.73 (m, 1 H); 2.60-2.53 (m, 1 H); 2.35-2.27 (m, 1 H); 2.18-2.10 (m, 1 H); 2.05-1.99 (m, 1 H); 1.76-1.66 (m, 2 H); 1.22-1.12 (m, 2 H). [ES MS] m/z 426 (MH⁺). | Scheme 1 (3N-r) | 4-chlorobenzaldehyde Fluka 23491 | | 0.266 |
| 22 | ¹H-NMR (δ, ppm, CDCl₃): 7.83 (d, 1 H); 7.76 (d, 1 H); 7.31 (s, 1 H); 7.24-7.16 (m, 3 H); 6.34 (d, 1 H); 5.07-4.98 (m, 1 H); 4.57-4.51 (dd, 1 H); 4.41-4.33 (m, 1 H); 3.76 (s, 2 H); 3.16-3.10 (dd, 1 H); 2.95-2.91 (m, 1 H); 2.73-2.65 (m, 2 H); 2.53-2.45 (m, 1 H); 2.36-2.20 (m, 2 H); 1.68-1.79 (m, 2 H); 1.39-1.27 (m, 2 H). [ES MS] m/z 426 (MH⁺). | Scheme 1 (3N-r) | 3-chlorobenzaldehyde Aldrich C2, 340-3 | | 1.065 |
| 23 | ¹H-NMR (δ, ppm, CDCl₃): 7.93 (s, 1 H); 7.83 (s, 1 H); 7.76 (d, 1 H); 7.48-7.45 (m, 1 H); 7.30 (s, 1 H); 6.39 (d, 1 H); 5.07-4.98 (m, 1 H); 4.58-4.52 (m, 1 H); 4.41-4.34 (m, 1 H); 3.83 (s, 2 H); 3.16-3.11 (m, 1 H); 2.95-2.91 (m, 1 H); 2.73-2.66 (m, 2 H); 2.58 (s, 3 H); 2.54-2.45 (m, 1 H); 2.37-2.21 (m, 2 H); 1.89-1.80 (m, 2 H); 1.37-1.29 (m, 2 H). [ES MS] m/z 451 (MH⁺). | Scheme 1 (3N-r) | 4-methyl-3-nitrobenzaldehyde Alfaaesar L 13454 | | 0.036 |
| 24 | ¹H-NMR (δ, ppm, CDCl₃): 7.82 (s, 1 H); 7.76 (d, 1 H); 6.58 (s, 1 H); 6.39 (d, 1 H); 5.07-4.98 (m, 1 H); 4.57-4.52 (m, 1 H); 4.41-4.34 (m, 1 H); 3.87 (s, 2 H); 3.16-3.10 (m, 1 H); 2.95-2.88 (m, 1 H); 2.72-2.63 (m, 2 H); 2.56-2.48 (m, 1 H); 2.37-2.20 (m, 2 H); 2.12 (s, 3 H); 1.87-1.76 (m, 2 H); 1.34-1.25 (m, 2 H). [ES MS] m/z 490 (MH⁺). | Scheme 1 (3N-r) | 2-bromo-3-methyl-5-formylthiophene Frontier B 1644 | | 0.077 |

TABLE 1-continued

| 25 | ¹H-NMR (δ, ppm, CDCl₃): 7.82 (s, 1 H); 7.76 (d, 1 H); 7.09-7.02 (m, 3 H); 6.38 (d, 1 H); 5.07-4.98 (m, 1 H); 4.57-4.52 (m, 1 H); 4.41-4.34 (m, 1 H); 3.73 (s, 2 H); 3.15-3.10 (m, 1 H); 2.96-2.92 (m, 1 H); 2.73-2.66 (m, 1 H); 2.57-2.48 (m, 1 H); 2.37-2.28 (m, 2 H); 2.25 (s, 3 H); 2.24 (s, 3 H); 1.91-1.81 (m, 2 H); 1.41-1.34 (m, 2 H). [ES MS] m/z 420 (MH⁺). | Scheme 1 (3N-r) | 4-Dimethylbenzaldehyde Aldrich 493856 | 0.262 |
|---|---|---|---|---|
| 26 | ¹H-NMR (δ, ppm, CDCl₃): 8.30 (d, 1 H); 7.82 (s, 1 H); 7.76 (d, 1 H); 7.65 (d, 1 H); 6.38 (d, 1 H); 5.07-4.98 (m, 1 H); 4.58-4.52 (m, 1 H); 4.41-4.34 (m, 1 H); 3.76 (s, 2 H); 3.16-3.11 (m, 1 H); 2.95-2.91 (m, 1 H); 2.73-2.66 (m, 2 H); 2.60 (s, 3 H); 2.53-2.44 (m, 1 H); 2.37-2.20 (m, 2 H); 1.89-1.80 (m, 2 H); 1.36-1.25 (m, 2 H). [ES MS] m/z 441 (MH⁺). | Scheme 1 (3N-r) | 5-chloro-6-methyl-3-pyridinecarbaldehyde WO20006/137485 A1 | 0.069 |
| 27 | ¹H-NMR (δ, ppm, CDCl₃): 8.30 (d, 1 H); 7.82 (s, 1 H); 7.76 (d, 1 H); 7.65 (d, 1 H); 6.38 (d, 1 H); 5.07-4.98 (m, 1 H); 4.58-4.52 (m, 1 H); 4.41-4.34 (m, 1 H); 3.76 (s, 2 H); 3.16-3.11 (m, 1 H); 2.95-2.91 (m, 1 H); 2.73-2.66 (m, 2 H); 2.60 (s, 3 H); 2.53-2.44 (m, 1 H); 2.37-2.20 (m, 2 H); 1.89-1.80 (m, 2 H); 1.36-1.25 (m, 2 H). [ES MS] m/z 441 (MH⁺). | Scheme 1 (3N-r) | 4-[(trifluoromethyl)oxy]benzaldehyde Matrix 29350-0100 | 2.377 |
| 28 | ¹H-NMR (δ, ppm, CDCl₃): 7.82 (s, 1 H); 7.76 (d, 1 H); 7.58 (d, 2 H); 7.43 (d, 2 H); 6.38 (d, 1 H); 5.07-4.98 (m, 1 H); 4.58-4.52 (m, 1 H); 4.41-4.34 (m, 1 H); 3.85 (s, 2 H); 3.16-3.11 (m, 1 H); 2.95-2.91 (m, 1 H); 2.73-2.66 (m, 2 H); 2.55-2.45 (m, 1 H); 2.37-2.21 (m, 2 H); 1.89-1.80 (m, 2 H); 1.37-1.30 (m, 2 H). [ES MS] m/z 460 (MH⁺). | Scheme 1 (3N-r) | 4-(trifluoromethyl)benzaldehyde Aldrich 22, 494-4 | 0.144 |

TABLE 1-continued

| | | | | |
|---|---|---|---|---|
| 29 | $^1$H-NMR (δ, ppm, CDCl$_3$): 7.82 (s, 1 H); 7.76 (d, 1 H); 7.43 (d, 2 H); 7.19 (d, 2 H); 6.38 (d, 1 H); 5.06-4.98 (m, 1 H); 4.57-4.52 (m, 1 H); 4.41-4.33 (m, 1 H); 3.74 (s, 2 H); 3.15-3.10 (m, 1 H); 2.94-2.90 (m, 1 H); 2.73-2.65 (m, 2 H); 2.51-2.45 (m, 1 H); 2.35-2.20 (m, 2 H); 1.87-1.80 (m, 2 H); 1.39-1.26 (m, 2 H). [ES MS] m/z 470 (MH$^+$). | Scheme 1 (3N-r) | 4-bromobenzaldehyde Aldrich B57400 | 0.147 |
| 30 | $^1$H-NMR (δ, ppm, DMSO-d$_6$): 8.46 (s, 1 H); 7.99 (s, 1 H); 7.85 (d, 1 H); 7.73 (s, 1 H); 6.24 (d, 1 H); 5.07-4.99 (m, 1 H); 4.36-4.21 (m, 2 H); 4.03-3.97 (m, 2 H); 3.00-2.95 (m, 2 H); 2.84-2.66 (m, 3 H); 2.53 (s, 3 H); 2.25-2.06 (m, 2 H); 1.95-1.87 (m, 2 H); 1.43-1.34 (m, 2 H). [ES MS] m/z 441 (MH$^+$). | Scheme 1 (3N-r) | 5-chloro-6-methyl-3-pyridinecarbaldehyde WO20006/137485 A1 | |
| 31 | $^1$H-NMR (δ, ppm, DMSO-d$_6$): 9.12 (bs, 2 H); 7.89 (s, 1 H); 7.75-7.71 (m, 3 H); 7.55 (d, 1 H); 6.18-6.11 (m, 2 H); 5.04-4.91 (m, 1 H); 4.37-4.20 (m, 2 H); 4.15 (s, 2 H); 3.09-2.87 (m, 3 H); 2.86-2.75 (m, 1 H); 2.74-2.61 (m, 1 H); 2.28-1.89 (m, 4 H); 1.62-1.38 (m, 2 H). [ES MS] m/z 459 (MH$^+$). | Scheme 3 (2N) | 3,4-dichlorobenzaldehyde Fluka 35270 | 0.019 |
| 32 | $^1$H-NMR (δ, ppm, CDCl$_3$): 8.47 (bd, 1 H); 7.69 (bd, 1 H); 7.51 (d, 1 H); 7.50 (d, 1 H); 6.31 (d, 1 H); 6.27 (d, 1 H); 5.06-4.95 (m, 1 H); 4.59 (dd, 1 H); 4.36 (dd, 1 H); 3.85 (s, 2 H); 3.12 (dd, 1 H); 3.01-2.92 (m, 1 H); 2.74-2.61 (m, 2 H); 2.56 (s, 3 H); 2.53-2.42 (m, 1 H); 2.38-2.17 (m, 2 H); 1.92-1.75 (m, 2 H); 1.41-1.21 (m, 2 H). [ES MS] m/z 431 (MH$^+$). | Scheme 3 (2N) | 5-formyl-3-methyl-2-pyridinecarbonitrile (see Preparation 3 above) | 0.538 |

| 33 | ¹H-NMR (δ, ppm, CDCl₃): 7.92 (bs, 1 H); 7.83 (s, 1 H); 7.78 (d, 1 H); 7.60 (bd, 1 H); 6.40 (d, 1 H); 5.09-4.98 (m, 1 H); 4.56 (dd, 1 H); 4.39 (dd, 1 H); 3.75 (s, 2 H); 3.15 (dd, 1 H); 2.99-2.90 (m, 1 H); 2.73-2.63 (m, 1 H); 2.71 (dd, 1 H); 2.56-2.44 (m, 1 H); 2.40-2.19 (m, 2 H); 2.28 (s, 3 H); 1.93-1.77 (m, 2 H); 1.42-1.23 (m, 2 H). [ES MS] m/z 425 (MH⁺). | Scheme 1 (3N-r) | 6-fluoro-5-methyl-3-pyridinecarbaldehyde Asymchem | 0.531 |
|---|---|---|---|---|
| 34 | ¹H-NMR (δ, ppm, CDCl₃): 7.82 (s, 1 H); 7.76 (d, 1 H); 7.04-7.33 (m, 3 H); 4.95-5.09 (m, 1 H); 4.50-4.56 (dd, 1 H); 4.33-4.43 (m, 1 H); 3.74 (s, 2 H); 3.13 (dd, 1 H); 2.89-2.99 (m, 1 H); 2.62-2.75 (m, 2 H); 2.58-2.46 (m, 1 H); 2.36 (s, 3 H); 2.34-2.17 (m, 2 H); 1.94-1.80 (m, 3 H); 1.48-1.31 (m, 2 H). [ES MS] m/z 440 (MH⁺). | Scheme 1 (3N-r) | 4-chloro-3-methylbenzaldehyde Fluorochem 22358 | 0.069 |
| 35 | ¹H-NMR (δ, ppm, CDCl₃): 7.82 (s, 1 H); 7.76 (d, 1 H); 7.13-7.08 (m, 1 H); 6.85-6.81 (m, 1 H); 6.39 (d, 1 H); 4.97-5.08 (m, 1 H); 4.55 (dd, 1 H); 4.31-4.43 (m, 1 H); 3.95 (s, 2 H); 3.13 (dd, 1 H); 2.88-2.97 (m, 1 H); 2.61-2.75 (m, 2 H), 2.47-2.60 (m, 1 H), 2.16-2.39 (m, 2 H); 2.83 (t, 2 H); 1.27-1.39 (m, 2 H). [ES MS] m/z 476 (MH⁺). | Scheme 1 (3N-r) | 4-bromo-2-thiophenecarbaldehyde Aldrich 283452-25G | 1.191 |
| 36 | ¹H-NMR (δ, ppm, CDCl₃): 7.83 (s, 1 H); 7.76 (d, 1 H); 7.43 (d, 1 H); 7.38 (d, 1 H); 7.17-7.13 (m, 1 H); 6.39 (d, 1 H); 5.07-4.98 (m, 1 H); 4.58-4.52 (m, 1 H); 4.41-4.34 (m, 1 H); 3.74 (s, 2 H); 3.16-3.11 (m, 1 H); 2.95-2.91 (m, 1 H); 2.73-2.66 (m, 2 H); 2.53-2.43 (m, 1 H); 2.37-2.20 (m, 2 H); 1.88-1.78 (m, 2 H); 1.35-1.25 (m, 2 H). [ES MS] m/z 460 (MH⁺). | Scheme 1 (3N-r) | 4-dichlorobenzaldehyde Fluka 35270 | 0.015 |

TABLE 1-continued

| | | | | |
|---|---|---|---|---|
| 37 | ¹H-NMR (δ, ppm, CDCl₃): 7.83 (s, 1 H); 7.76 (d, 1 H); 7.34 (s, 1 H); 6.38 (d, 1 H); 5.07-4.98 (m, 1 H); 4.57-4.52 (m, 1 H); 4.41-4.34 (m, 1 H); 3.94 (s, 2 H); 3.17-3.11 (m, 1 H); 2.94-2.91 (m, 1 H); 2.73-2.65 (m, 2 H); 2.56-2.45 (m, 1 H); 2.38-2.20 (m, 2 H); 1.86-1.78 (m, 2 H); 1.33-1.25 (m, 2 H). [ES MS] m/z 433 (MH⁺). | Scheme 1 (3N-r) | 2-chloro-5-(chloromethyl)-1,3-thiazole AK Scientific 765295 | 2.165 |
| 38 | ¹H-NMR (δ, ppm, CDCl₃): 7.83 (s, 1 H); 7.76 (d, 1 H); 7.32 (s, 1 H); 7.21-7.12 (m, 1 H); 6.85 (d, 1 H); 6.37 (d, 1 H); 5.09-4.98 (m, 1 H); 4.55 (dd, 1 H); 4.39 (dd, 1 H); 3.87 (s, 3 H); 3.71 (s, 2 H); 3.12 (dd, 1 H); 2.97-2.87 (m, 1 H); 2.75-2.64 (m, 2 H); 2.55-2.44 (m, 1 H); 2.39-2.21 (m, 2 H); 1.95-1.76 (m, 2 H); 1.41-1.24 (m, 2 H). [ES MS] m/z 456 (MH⁺). | Scheme 1 (3N-r) | 4-nitrobenzaldehyde Fluka 72802 | 0.273 |
| 39 | ¹H-NMR (δ, ppm, CDCl₃): 7.83 (s, 1 H); 7.76 (d, 1 H); 7.32 (s, 1 H); 7.21-7.12 (m, 1 H); 6.85 (d, 1 H); 6.37 (d, 1 H); 5.09-4.98 (m, 1 H); 4.55 (dd, 1 H); 4.39 (dd, 1 H); 3.87 (s, 3 H); 3.71 (s, 2 H); 3.12 (dd, 1 H); 2.97-2.87 (m, 1 H); 2.75-2.64 (m, 2 H); 2.55-2.44 (m, 1 H); 2.39-2.21 (m, 2 H); 1.95-1.76 (m, 2 H); 1.41-1.24 (m, 2 H). [ES MS] m/z 456 (MH⁺). | Scheme 1 (3N-r) | 3-chloro-4-methoxybenzaldehyde Aldrich 565040 | 1.140 |
| 40 | ¹H-NMR (δ, ppm, CDCl₃): 8.57 (s, 1 H); 7.85 (s, 1 H); 7.80-7.70 (m, 2 H); 7.22 (d, 1 H); 6.37 (d, 1 H); 5.07-4.96 (m, 1 H); 4.55 (dd, 1 H); 4.39 (dd, 1 H); 3.82 (s, 2 H); 3.12 (dd, 1 H); 2.97-2.86 (m, 1 H); 2.75-2.64 (m, 2 H); 2.55-2.44 (m, 1 H); 2.38-2.22 (m, 2 H); 1.93-1.79 (m, 2 H); 1.44-1.27 (m, 2 H). [ES MS] m/z 471 (MH⁺). | Scheme 1 (3N-r) | 5-Bromopyridine-2-carbaldehyde Alfaaesar H50154 | 1.178 |

TABLE 1-continued

| | | | | |
|---|---|---|---|---|
| 41 | ¹H-NMR (δ, ppm, CDCl₃): 8.56 (s, 1 H); 8.45 (s, 1 H); 7.85 (s, 1 H); 7.81 (s, 1 H); 7.75 (d, 1 H); 6.37 (d, 1 H); 5.06-4.96 (m, 1 H); 4.55 (dd, 1 H); 4.39 (dd, 1 H); 3.74 (s, 2 H); 3.12 (dd, 1 H); 2.97-2.86 (m, 1 H); 2.75-2.64 (m, 2 H); 2.52-2.42 (m, 1 H); 2.38-2.22 (m, 2 H); 1.91-1.77 (m, 2 H); 1.42-1.25 (m, 2 H). [ES MS] m/z 471 (MH⁺). | Scheme 1 (3N-r) | 5-Bromo-3-pyridinecarboxaldehyde Aldrich 644102 | 0.884 |
| 42 | ¹H-NMR (δ, ppm, CDCl₃): 8.47 (d, 1 H); 8.43 (d, 1 H); 7.84 (s, 1 H), 7.78 (d, 1 H); 7.72 (bs, 1 H); 6.40 (d, 1 H); 5.08-4.99 (m, 1 H); 4.56 (dd, 1 H); 4.39 (dd, 1 H); 3.82 (s, 2 H); 3.15 (dd, 1 H); 2.99-2.90 (m, 1 H); 2.76-2.65 (m, 2 H); 2.56-2.46 (m, 1 H); 2.39-2.22 (m, 2 H); 1.92-1.81 (m, 2 H); 1.41-1.27 (m, 2 H). [ES MS] m/z 427 (MH⁺). | Scheme 1 (3N-r) | 5-chloro-3-pyridinecarbaldehyde Frontier C 10088 | 1.067 |
| 43 | ¹H-NMR (δ, ppm CDCl₃): 7.81 (s, 1 H); 7.76 (d, 1 H); 7.10 (t, 1 H); 6.98-6.92 (m, 1 H); 6.36 (d, 1 H), 5.07-4.96 (m, 1 H); 4.54 (dd, 1 H); 4.37 (dd, 1 H); 3.73 (s, 2 H); 3.12 (dd, 1 H); 2.96-2.91 (m, 1 H); 2.73-2.64 (m, 2 H); 2.58-2.47 (m, 1 H); 2.36-2.17 (m, 2 H); 2.24 (s, 3 H); 1.90-1.81 (m, 2 H); 1.47-1.31 (m, 2 H). [ES MS] m/z 424 (MH⁺). | Scheme 1 (3N-r) | 3-fluoro-4-methyl benzaldehyde Alfaaesar B23736 | 0.066 |
| 44 | ¹H-NMR (δ, ppm, CDCl₃): 7.82 (s, 1 H); 7.76 (d, 1 H); 6.94-7.21 (m, 3 H); 6.38 (d, 1 H); 5.09-4.97 (m, 1 H); 4.55 (dd, 2 H); 4.37 (dd, 1 H); 3.75 (s, 2 H); 3.13 (dd, 1 H); 2.98-2.88 (m, 1 H); 2.75-2.65 (m, 2 H) 2.55-2.43 (m, 1 H); 2.38-2.18 (m, 2 H); 1.91-1.76 (m, 2 H); 1.42-1.28 (m, 2 H). [ES MS] m/z 428 (MH⁺). | Scheme 1 (3N-r) | 3,4-difluorobenzaldehyde Aldrich 26, 516-0 | 0.267 |

TABLE 1-continued

| | | | | |
|---|---|---|---|---|
| 45 | $^1$H-NMR (δ, ppm, CDCl$_3$): 8.69 (s, 1 H); 7.94-7.91 (m, 1 H); 7.82 (s, 1 H); 7.77 (d, 1 H); 7.65 (d, 1 H); 6.38 (d, 1 H); 5.07-4.99 (m, 1 H); 4.57 (m, 1 H); 4.42-4.35 (m, 1 H); 3.91 (s, 2 H); 3.18 (m, 1 H); 2.98-2.93 (m, 1 H); 2.73-2.66 (m, 2 H); 2.58-2.49 (m, 1 H); 2.38-2.21 (m, 2 H); 1.93-1.83 (m, 2 H); 1.45-1.34 (m, 2 H). [ES MS] m/z 461 (MH$^+$). | Scheme 1 (3N-r) | 6-(trifluoromethyl)-3-pyridinecarbaldehyde Fluorochem 009397 | HCl salt tested below |
| 46 | $^1$H-NMR (δ, ppm, DMSO-d$_6$): 9.30-9.17 (m, 1 H); 8.89 (s, 1 H); 8.27 (d, 1 H); 8.01 (d, 1 H); 7.85 (d, 1 H); 7.73 (s, 1 H); 6.25 (d, 1 H); 5.07-5.01 (m, 1 H); 4.37-4.20 (m, 4 H); 3.06-2.96 (m, 3 H); 2.86-2.72 (m, 2 H); 2.26-1.98 (m, 4 H); 1.57-1.47 (m, 2 H). [ES MS] m/z 461 (MH$^+$). | As above | As above | 0.078 |
| 47 | $^1$H-NMR (δ, ppm, CDCl$_3$): 7.83 (s, 1 H); 7.77 (d, 1 H); 7.44 (d, 1 H); 7.38 (d, 1 H); 7.17-7.14 (m, 1 H); 6.39 (d, 1 H); 5.06-4.99 (m, 1 H); 4.55 (dd, 1 H); 4.38 (dd, 1 H); 3.75 (s, 2 H); 3.14 (dd, 1 H); 2.96-2.90 (m, 1 H); 2.72-2.64 (m, 2 H); 2.53-2.44 (m, 1 H); 2.36-2.30 (m, 1 H); 2.27-2.21 (m, 1 H); 1.89-1.78 (m, 2 H); 1.39-1.25 (m, 2 H). [ES MS] m/z 460 (MH$^+$). | Scheme 1 (3N-r) | 3,4-Dichlorobenzaldehyde Fluka 35270 | 0.072 |
| 48 | $^1$H-NMR (δ, ppm, CDCl$_3$): 8.66 (s, 1 H); 7.87 (d, 1 H); 7.82 (s, 1 H); 7.77 (d, 1 H); 7.65 (d, 1 H); 6.37 (d, 1 H); 5.09-4.96 (m, 1 H); 4.55 (dd, 1 H); 4.40 (dd, 1 H); 3.90 (s, 2 H); 3.13 (dd, 1 H); 2.96-2.86 (m, 1 H); 2.73 (dd, 1 H); 2.57-2.48 (m, 1 H); 2.38-2.31 (m, 1 H); 2.31-2.20 (m, 2 H); 1.93-1.76 (m, 2 H); 1.42-1.20 (m,, 2 H). [ES MS] m/z 461 (MH$^+$). | Scheme 1 (3N-r) | 6-(trifluoromethyl)pyridine-3-carboxaldehyde Apollo PC4333 | 2.302 |

TABLE 1-continued

| | | | | |
|---|---|---|---|---|
| 49 | ¹H-NMR (δ, ppm, CDCl₃ + CD₃OD): 8.49 (s, 1 H); 7.94 (s, 1 H); 7.52 (d, 1 H); 7.51 (d, 1 H); 6.29 (d, 1 H); 6.24 (d, 1 H); 5.05-4.93 (m, 1 H); 4.51 (dd, 1 H); 4.34 (dd, 1 H); 3.86 (s, 2 H); 3.11-2.89 (m, 2 H); 2.73-2.56 (m, 2 H); 2.53-2.40 (m, 1 H); 2.35-2.14 (m, 2 H); 1.91-1.73 (m, 2 H); 1.41-1.18 (m, 2 H). [ES MS] m/z 451 (MH⁺). | Scheme 3 (2N) | 3-chloro-5-formyl-2-pyridinecarbonitrile (Preparation 4 above) | 0.07 |
| 50 | [ES MS] m/z 451 (MH⁺). | Scheme 3 (2N) | As above | 0.082 |
| 51 | ¹H-NMR (δ, ppm, CD₃OD): 8.41 (s, 1 H), 8.07 (s, 1 H), 7.88 (d, 1 H), 7.78 (s, 1 H), 6.37 (d, 1 H), 5.16-5.10 (m, 1 H), 4.45-4.42 (m, 2 H), 3.93 (s, 2 H), 3.13-3.07 (m, 2 H), 2.86 (dd, 1 H), 2.78-2.73 (m, 2 H), 2.63 (s, 3 H), 2.36-2.21 (m, 2 H), 2.01-1.91 (m, 2 H), 1.47-1.38 (m, 2 H). [ES MS] m/z 485 (MH⁺). | Scheme 1 (3N-r) | 5-Bromo-6-methyl-3-pyridinecarbaldehyde (Preparation 7 above) | 0.015 |
| 52 | ¹H-NMR (δ, ppm, CDCl₃): 8.27 (bs, 1 H); 7.83-7.55 (m, 2 H); 7.61 (bs, 1 H); 6.37 (d, 1 H); 5.08-5.00 (m, 1 H); 4.57-4.52 (m, 1 H); 4.45-4.37 (m, 1 H); 3.84 (bs, 2 H); 3.21-3.15 (m, 1 H); 3.02-2.98 (m, 1 H); 2.74-2.67 (m, 3 H); 2.40-2.22 (m, 2 H); 1.94 (bs, 2 H); 1.52 (m, 2 H). [ES MS] m/z 425 (MH⁺). | Scheme 1 (3N-r) | 5-Fluoro-6-methyl-3-pyridinecarbaldehyde (Preparation 5 above) | >2.122 |
| 53 | ¹H-NMR (δ, ppm, CDCl₃): 8.32 (s, 1 H); 7.82-7.71 (m, 3 H); 6.38 (d, 1 H); 5.06-4.98 (m, 1 H); 4.57-4.51 (m, 1 H); 4.42-4.35 (m, 1 H); 3.80 (s, 2 H); 3.17-3.12 (m, 1 H); 2.97-2.93 (m, 1 H); 2.73-2.66 (m, 2 H); 2.60 (s, 3 H); 2.55-2.50 (m, 1 H); 2.37-2.21 (m, 2 H); 1.92-1.83 (m, 2 H); 1.44-1.35 (m, 2 H). [ES MS] m/z 441 (MH⁺). | Scheme 1 (3N-r) | The racemic Example 26 was resolved into its two enantiomers by preparative chiral HPLC to give Example 53 | 0.830 |

TABLE 1-continued

| | | | | |
|---|---|---|---|---|
| 54 | ¹H-NMR (δ, ppm, CDCl₃): 8.29 (d, 1 H); 7.54-7.47 (m, 3 H); 6.27 (dd, 2 H); 5.05-4.97 (m, 1 H); 4.57 (dd, 1 H); 4.36 (d, 1 H); 3.82 (s, 2 H); 3.12 (dd, 1 H); 3.01-2.97 (m, 1 H); 2.80 (q, 2 H); 2.71-2.64 (m, 2 H); 2.58-2.52 (m, 1 H); 2.37-2.21 (m, 2 H); 1.94-1.84 (m, 2 H); 1.48-1.36 (m, 2 H); 1.27 (t, 3 H). [ES MS] m/z 438 (MH⁺). | Scheme 3 (2N) | 6-ethyl-5-fluoro-3-pyridinecarbaldehyde (Preparation 6 above) | 2.188 |
| 55 | ¹H-NMR (δ, ppm, CD₃OD): 8.42 (d, 1 H); 8.09 (d, 1 H); 7.88 (d, 1 H); 7.81 (s, 1 H); 6.34 (d, 1 H); 5.14-5.06 (m, 1 H); 4.48-4.46 (m, 2 H); 3.99 (s, 2 H); 3.13-3.06 (m, 2 H); 2.92-2.72 (m, 3 H); 2.64 (s, 3 H); 2.35-2.24 (m, 2 H); 2.05-1.93 (m, 2 H); 1.55-1.37 (m, 2 H). [ES MS] m/z 485 (MH⁺). | Scheme 2 (3N-l) | 5-bromo-6-methyl-3-pyridinecarbaldehyde (Preparation 7 above) | 0.04 |
| 56 | 1H-NMR (δ, ppm, CDCl₃ + CD₃OD): 8.39 (s, 1 H); 7.72 (s, 1 H); 7.52 (d, 1 H); 7.50 (d, 1 H); 6.31 (d, 1 H); 6.26 (d, 1 H); 5.07-4.95 (m, 1 H); 4.76 (s, 2 H); 4.56 (dd, 1 H); 4.36 (dd, 1 H); 3.81 (s, 2 H); 3.09 (dd, 1 H); 2.96 (bd, 1 H); 2.73-2.59 (m, 2 H); 2.54-2.42 (m, 1 H); 2.36-2.16 (m, 2 H); 1.92-1.75 (m, 2 H); 1.42-1.21 (m, 2 H). ([ES MS] m/z 456 (MH⁺). | Scheme 3 (2N) | 5-Chloro-6-(hydroxymethyl)-3-pyridinecarbaldehyde. (Preparation 8 above) | 0.3 |
| 57 | ¹H-NMR (δ, ppm, CDCl₃): 7.83 (s, 1 H); 7.78 (d, 1 H); 7.08 (d, 1 H); 6.85 (s, 1 H); 6.79 (d, 1 H); 6.39 (d, 1 H); 5.08-4.96 (m, 1 H); 4.56 (dd, 1 H); 4.38 (dd, 1 H); 3.85 (s, 3 H); 3.78 (s, 2 H); 3.14 (dd, 1 H); 2.95 (bd, 1 H); 2.74-2.65 (m, 2 H); 2.64-2.50 (m, 1 H); 2.31 (m, 2 H); 2.20 (s, 3 H); 1.99-1.76 (m, 2 H); 1.49-1.34 (m, 2 H). [ES MS] m/z 436 (MH⁺). | Scheme 1 (3N-r) | 4-methyl-3-(methyloxy) benzaldehyde Apollo OR11329 | 1.089 |

TABLE 1-continued

| | | | | |
|---|---|---|---|---|
| 58 | $^1$H-NMR (δ, ppm, CDCl$_3$): 8.40 (s, 1 H); 7.87 (s, 1 H); 7.51-7.47 (dd, 2 H); 6.30-6.22 (dd, 2 H); 5.04-4.95 (m, 1 H); 4.57-4.51 (dd, 1 H); 4.41-4.33 (dd, 1 H); 3.87 (s, 2 H); 3.13-3.08 (dd, 1 H); 3.04-3.00 (bd, 1 H); 2.96-2.89 (dd, 2 H); 2.73-2.64 (m, 3 H); 2.34-2.19 (m, 2 H); 1.99-1.90 (bt, 2 H); 1.59-1.50 (m, 2 H); 1.29-1.24 (t, 3 H). [ES MS] m/z 453 (MH$^+$). | Scheme 3 (2N) | 5-chloro-6-ethyl-3-pyridinecarbaldehyde (Preparation 10 above) | |
| 59 | $^1$H-NMR (δ, ppm, DMSO-d$_6$): 10.21 (bs, 1 H), 9.01 (s, 1 H), 8.43 (d, 1 H), 8.02 (d, 1 H), 7.79 (dd, 2 H), 6.22 (d, 2 H), 5.40 (bs, 1 H), 4.50-4.36 (m, 4 H), 3.80-3.66 (m, 5 H), 3.17 (bs, 2 H), 2.17 (bs, 4 H). [ES MS] m/z 460 (MH$^+$). | Scheme 3 (2N) | 6-(trifluoromethyl)-3-pyridinecarbaldehyde Apollo PC4333 | 0.154 |
| 60 | $^1$H-NMR (d, ppm, CDCl3): 8.42 (s, 1 H); 7.65 (s, 1 H); 7.50 (dd, 2 H); 6.34-6.22 (m, 2 H); 5.06-4.97 (m, 1 H); 4.59 (dd, 1 H); 4.40-4.32 (m, 1 H); 3.85 (s, 2 H); 3.12 (dd, 1 H); 2.98-2.94 (m, 1 H); 2.71-2.64 (m, 2 H); 2.50 (d, 3 H); 2.36-2.20 (m, 2 H), 1.90-1.80 (m, 2 H); 1.41-1.24 (m, 3 H). ([ES MS] m/z 474 (MH+). | As Example 1 | 5-Methyl-6-(trifluoromethyl)-3-pyridinecarbaldehyde. (See preparation 12) | Summarised above |
| 61 | 1H-NMR (d, ppm, CDCl3): 8.54 (s, 1 H); 8.11 (s, 1 H); 7.50 (dd, 2 H); 6.32 (d, 1 H); 6.26 (d, 1 H); 5.06-4.97 (m, 1 H); 4.59 (dd, 1 H); 4.40-4.33 (m, 1 H); 3.88 (s, 2 H); 3.12 (dd, 1 H); 2.99-2.95 (m, 1 H); 2.71-2.64 (m, 2 H); 2.53-2.44 (m, 1 H); 2.37-2.20 (m, 2 H), 1.85 (bt, 2 H); 1.41-1.23 (m, 3 H). ([ES MS] m/z 538 (MH+). | As Example 1 (2N) | 5-bromo-6-(trifluoromethyl)-3-pyridinecarbaldehyde (see preparation 15) | Summarised above |

TABLE 1-continued

| | | | | |
|---|---|---|---|---|
| 62 | 1H-NMR (d, ppm, CDCl3): 8.34 (s, 1 H); 7.74 (s, 1 H); 7.49 (dd, 2 H); 6.34-6.22 (m, 2 H); 6.15 (s, 1 H); 5.07-4.94 (m, 1 H); 4.58 (dd, 1 H); 4.41-4.30 (m, 1 H); 3.81 (s, 2 H); 3.11 (dd, 1 H); 2.96 (bd, 1 H); 2.73-2.60 (m, 2 H); 2.56-2.43 (m, 1 H); 2.39-2.16 (m, 2 H); 1.85 (bt, 2 H); 1.67 (s, 6 H); 1.40-1.20 (m, 2 H). ([ES MS] m/z 484 (MH+). | As Example 1 (2N) | 5-chloro-6-(1-hydroxy-1-methylethyl)-3-pyridinecarbaldehyde. (See preparation 13) | Summarised above |
| 63 | 1H-NMR (d, ppm, CDCl3): 8.25 (d, 1 H); 7.53 (s, 1 H); 7.50 (dd, 2 H); 6.31 (d, 1 H); 6.26 (d, 1 H), 5.06-4.98 (m, 1 H); 4.58 (dd, 1 H); 4.42-4.35 (m, 1 H); 3.81 (s, 2 H); 3.14 (dd, 1 H); 3.03-2.99 (m, 1 H); 2.72-2.65 (m, 2 H); 2.53 (s, 3 H); 2.38-2.23 (m, 2 H); 1.96-1.88 (m, 2 H), 1.44 (bs, 3 H). ([ES MS] m/z 424 (MH+). | As Example 1 | 5-fluoro-6-methyl-3-pyridinecarbaldehyde (Preparation 5) | Summarised above |
| 64 | 1H-NMR (d, ppm, CDCl3): 7.49 (dd, 2 H); 7.41 (d, 1 H); 7.34 (s, 1 H); 7.24-7.18 (m, 1 H); 6.28 (dd, 2 H); 5,07-4.94 (m, 1 H); 4.76 (s, 2 H); 4, 57 (dd, 1 H); 4.34 (dd, 1 H); 3.76 (s, 2 H); 3.08 (dd, 1 H); 2.99-2.90 (m, 1 H); 2.70-2.58 (m, 2 H); 2.53-2.40 (m, 1 H); 2.36-2.15 (m, 2 H); 1.92-1.75 (m, 2 H); 1.41-1.22 (m, 2 H);. ([ES MS] m/z 455 (MH+). | | This compound was prepared by ester hydrolysis of the compound of Example 71 | Summarised above |
| 65 | $^1$H-NMR (δ, ppm, CDCl$_3$): 8.35 (s, 1 H); 7.81 (s, 1 H); 7.75 (d, 1 H); 7.67 (s, 1 H); 6.36 (d, 1 H); 5.06-4.99 (m, 1 H); 4.56-4.50 (m, 1 H); 4.40-4.33 (m, 1 H); 3.80-3.76 (m, 4 H); 3.36 (s, 3 H); 3.20 (t, 2 H); 3.15-3.10 (m, 1 H); 2.93 (bd, 1 H); 2.72-2.65 (m, 2 H); 2.53-2.46 (m, 1 H); 2.23 (dt, 2 H); 1.84 (t, 2 H); 1.37-1.27 (m, 2 H). [ES MS] m/z 485 (MH$^+$). | As Example 1 | 5-chloro-6-[2-(methyloxy)ethyl]-3-pyridinecarbaldehyde. (see preparation 19) | Summarised above |

TABLE 1-continued

| | | | | |
|---|---|---|---|---|
| 66 | 1H-NMR (δ, CD$_3$OD): 8.43 (s, 1 H); 8.09 (s, 1 H); 7.88 (d, 1 H); 7.81 (s, 1 H); 6.34 (d, 1 H); 5.14-5.06 (m,1 H); 4.48-4.46 (m, 2 H); 3.99 (s, 2 H); 3.13-3.05 (m, 2 H); 2.92-2.72 (m, 3 H); 2.64 (s, 3 H); 2.35-2.24 (m, 2 H); 2.05-1.93 (m, 2 H); 1.55-1.41 (m, 2 H). [ES MS] m/z 485 (MH$^+$). | As Example 1 | 5-bromo-6-methyl-3-pyridinecarbaldehyde (see preparation 7) | Summarised above |
| 67 | 1H-NMR (d, ppm, D2O): 8.71 (s, 1 H); 8.28 (s, 1 H); 8.02 (d, 2 H); 6.56 (d, 1 H); 5.73 (bs, 1 H); 4.48 (s, 2 H); 4.35-4.29 (m, 1 H); 4.24-4.18 (m, 1 H); 3.95-3.87 (m, 1 H); 3.78-3.68 (m, 3 H); 3.38-3.21 (m, 2 H), 2.58 (bt, 2 H); 2.19-2.01 (m, 2 H). ([ES MS] m/z 452 (MH+). | As Example 1 | Preparation 4 | Summarised above |
| 68 | 1H-NMR (d, ppm, CDCl3): 8.26 (s, 1 H); 8.17 (s, 1 H); 7.51 (dd, 2 H); 6.22 (dd, 2 H); 5.04-4.89 (m, 1 H); 4.49-4.26 (m, 2 H); 3.97 (s, 2 H); 3.11-2.97 (m, 2 H); 2.92-2.78 (m, 1 H); 2.76-2.59 (m, 2 H); 2.37-2.17 (m, 2 H); 2.08-1.93 (m, 2 H); 1.64-1.40 (m, 2 H). ([ES MS] m/z 460 (MH+). | As Example 1 | 5,6-dichloro-3-pyridinecarbaldehyde (see preparation 2) | Summarised above |
| 69 | 1H-NMR (d, ppm, CDCl3): 8.23-8.22 (d, 1 H); 7.83 (d, 1 H); 7.81 (s, 1 H); 7.78-7.75 (d, 1 H); 6.40-6.37 (d, 1 H); 5.07-4.98 (m, 1 H); 4.58-4.52 (dd, 1 H); 4.41-4.34 (dd, 1 H); 3.79 (s, 2 H); 3.17-3.12 (dd, 1 H); 2.95-2.91 (bd, 1 H); 2.73-2.66 (m, 2 H); 2.53-2.43 (m, 1 H); 2.38-2.20 (m, 2 H); 1.88-1.80 (bt, 2 H); 1.39-1.24 (m, 2 H). ([ES MS] m/z 461 (MH+). | As Example 1 | 5,6-dichloro-3-pyridinecarbaldehyde (See preparation 2) | Summarised above |

TABLE 1-continued

| | | | | | |
|---|---|---|---|---|---|
| | 70 | 1H-NMR (d, ppm, (CDCl3): 8.40 (s, 1 H); 7.83-7.72 (m, 3 H); 6.39 (d, 1 H); 5.07-4.99 (m, 1 H); 4.77 (s, 2 H); 4.58-4.52 (m, 1 H); 4.41-4.33 (m, 1 H); 3.82 (s, 2 H); 3.15 (dd, 1 H); 2.96-2.92 (m, 1 H); 2.74-2.66 (m, 2 H); 2.53-2.46 (m, 1 H); 2.38-2.21 (m, 2 H); 1.90-1.80 (m, 2 H); 1.36-1.28 (m, 2 H). ([ES MS] m/z 457 (MH+). | As Example 1 | 5-chloro-6-(hydroxymethyl)-3-pyridinecarbaldehyde (See Preparation 8) | Summarised above |
| | 71 | 1H-NMR (d, ppm, CDCl3): 7.49 (dd, 2 H); 7.42-7.33 (m, 2 H); 7.30-7.22 (m, 1 H); 6.26 (dd, 2 H); 5.19 (s, 2 H); 5.08-.92 (m, 1 H); 4.56 (dd, 1 H); 4.37 (dd, 1 H); 3.80 (s, 2 H); 3.10 (dd, 1 H); 3.02-2.91 (m, 1 H); 2.72-2.59 (m, 2 H); 2.61-2.45 (m, 1 H); 2.37-2.17 (m, 2 H); 2.12 (s, 3 H); 1.95-1.77 (m, 2 H); 1.46-1.31 (m, 2 H);. ([ES MS] m/z 497 (MH+). | | [4-(bromomethyl)-2-chlorophenyl]methyl acetate (see preparation 18) | Summarised above |
| | 72 | 1H-NMR (d, ppm, CDCl3): 8.38 (s, 1 H); 7.70 (s, 1 H); 7.51-7.47 (dd, 2 H); 6.32-6.23 (dd, 2 H); 5.16-5.09 (dd, 1 H); 5.05-4.96 (m, 1 H); 4.60-4.55 (dd, 1 H); 4.39-4.32 (dd, 1 H); 3.80 (s, 2 H); 3.13-3.08 (dd, 1 H); 2.98-2.94 (bd, 1 H); 2.70-2.63 (bdd, 2 H); 2.50-2.47 (m, 1 H); 2.35-2.20 (m, 2 H); 2.17 (s, 1 H); 1.89-1.79 (t, 2 H); 1.46-1.44 (d, 3 H); 1.35-1.27 (m, 2 H). ([ES MS] m/z 470 (MH+). | As Example 1 | 5-chloro-6-(1-hydroxyethyl)-3-pyridinecarbaldehyde (see preparation 14) | Summarised above |

TABLE 1-continued

| | | | | |
|---|---|---|---|---|
| 73 | 1H-NMR (d, ppm, CDCl3): 7.50-7.46 (dd, 2 H); 7.45 (s, 1 H); 6.31-6.23 (q, 2 H); 5.03-4.97 (m, 1 H); 4.60-4.54 (dd, 1 H); 4.38-4.34 (dd, 1 H); 4.05 (s, 2 H); 3.12-3.07 (dd, 1 H); 2.96-2.92 (bd, 1 H); 2.67-2.63 (m, 2 H); 2.56-2.46 (m, 1 H); 2.34-2.19 (m, 2 H); 1.89-1.73 (bt, 2 H); 1.41-1.25 (m, 2 H). ([ES MS] m/z 441 (MH+). | As Example 1 | 6-chloro-5-methyl-3-pyridazinecarbaldehyde (see preparation 16) | Summarised above |
| 74 | 1H-NMR (d, ppm, CDCl3): 8.14 (s, 1 H); 7.56 (s, 1 H); 7.51-7.47 (dd, 2 H); 6.31-6.23 (dd, 2 H); 5.04-4.96 (m, 1 H); 4.60-4.54 (dd, 1 H); 4.39-4.31 (dd, 1 H); 3.75 (s, 2 H); 3.12-3.07 (dd, 1 H); 2.97-2.93 (bd, 1 H); 2.70-2.63 (m, 2 H); 2.48-2.42 (m, 1 H); 2.37 (s, 3 H); 2.34-2.19 (m, 2 H); 1.88-1.77 (t, 2 H); 1.40-1.22 (m, 2 H). ([ES MS] m/z 440 4.9-diane (MH+). | As Example 1 | 6-chloro-5-methyl-3-pyridinecarbaldehyde (see preparation 17) | Summarised above |
| 75 | 1H-NMR (d, ppm, DMSO-d6): 9.63 (bs, 1 H); 8.73 (s, 1 H); 8.20 (s, 1 H); 7.83 (d, 1 H); 7.74 (s, 1 H); 6.26 (d, 1 H); 5.22 (bs, 1 H); 4.48-4.32 (m, 2 H); 4.27 (s, 2 H); 2.18 (bs, 2 H); 1.83 (bs, 2 H). ([ES MS] m/z 475 (MH+) | As Example 1 (3N) | 5-Methyl-6-(trifluoromethyl)-3-pyridinecarbaldehyde. (See preparation 12) | Summarised above |

The invention claimed is:

1. A compound of Formula (I) or a pharmaceutically acceptable salt or N-oxide thereof:

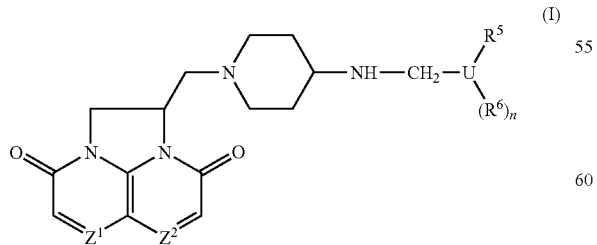

wherein:

one of $Z^1$ and $Z^2$ is CH or N and the other of $Z^1$ and $Z^2$ is CH;

U is selected from the group consisting of phenyl, pyridyl, pyridazinyl, pyrimidinyl, pyrazinyl, thiazolyl, furanyl, imidazolyl and thiophenyl;

n is 0 or 1;

$R^5$ and $R^6$ are independently selected from the group consisting of halo, $CF_3$, $OCF_3$, $C_{1-3}$ alkyl, $NHR^7$, $NR^{7A}R^{7B}$, $C_{1-3}$ alkoxy, nitro and cyano; or $R^5$ is —$C_mH_{2m}$-A where m is 1-5 and the moiety —$C_mH_{2m}$— is a straight or branched chain and A is selected from the group consisting of OH, $OR^7$, $OCOR^7$, $OCO_2R^7$, $OCONR^7$, $OPO_2R^7$ and $NH_2$, where $R^7$, $R^{7A}$ and $R^{7B}$ are each independently $C_{1-5}$ alkyl.

2. The compound of claim 1 or a pharmaceutically acceptable salt thereof or N-oxide thereof wherein the compound of Formula (I) is represented by the Formula (IA) or a pharmaceutically acceptable salt or N-oxide thereof:

(Formula IA)

wherein:
one of $Z^1$ and $Z^2$ is CH or N and the other of $Z^1$ and $Z^2$ is CH;
U is selected from the group consisting of phenyl, pyridyl, pyridazinyl, pyrimidinyl, pyrazinyl, thiazolyl, furanyl, imidazolyl and thiophenyl;
$R^5$ and $R^6$ are independently selected from the group consisting of halo, $CF_3$, $OCF_3$, $C_{1-3}$ alkyl, $C_{1-3}$ alkoxy, nitro and cyano, and n is 0 or 1.

3. The compound of claim 1 or a pharmaceutically acceptable salt thereof or N-oxide thereof wherein in Formula (I) U represents a group selected from the group consisting of phenyl, pyridyl, pyridazinyl, thiazolyl, and thiophenyl.

4. The compound of claim 1 or a pharmaceutically acceptable salt thereof or N-oxide thereof wherein when n is 0; and $R^5$ represents $CF_3$, $OCF_3$, Cl, Br, or $NO_2$.

5. The compound of claim 1 or a pharmaceutically acceptable salt thereof or N-oxide thereof wherein n=1; and one of $R^5$ and $R^6$ represents Cl and the other of $R^5$ and $R^6$ represents Cl, $CH_3$, $C_2H_5$, CN, $CF_3$ or $OCF_3$.

6. The compound of claim 1 or a pharmaceutically acceptable salt thereof or N-oxide thereof wherein n=1; and one of $R^5$ and $R^6$ represents F and the other of $R^5$ and $R^6$ represents Cl, $CF_3$, CN, or $CH_3$.

7. The compound of claim 1 or a pharmaceutically acceptable salt thereof or N-oxide thereof wherein n=1; and one of $R^5$ and $R^6$ represents $CH_3$ and the other of $R^5$ and $R^6$ represents Br, $CH_3$, $CF_3$, CN or $NO_2$.

8. The compound of claim 1 or a pharmaceutically acceptable salt thereof or N-oxide thereof wherein $R^5$ represents —$CH_2$—OH; n is 1; and $R^6$ is Cl.

9. The compound of claim 1 or a pharmaceutically acceptable salt thereof or N-oxide thereof wherein U is selected from the group consisting of phenyl, pyridyl and pyridazinyl; n is 0; and $R^5$ is in the para position of U relative to the bond between U and the $CH_2$ group to which it is bonded.

10. The compound of claim 1 or a pharmaceutically acceptable salt thereof or N-oxide thereof wherein U is selected from the group consisting of phenyl and pyridyl; n is 1; and one of $R^5$ and $R^6$ is in the para position, and the other of $R^5$ and $R^6$ is in the meta position of U relative to the bond between U and the $CH_2$ group to which it is bonded.

11. The compound of claim 1 or a pharmaceutically acceptable salt thereof or N-oxide thereof wherein the absolute stereochemistry of the compound of Formula (I) is indicated by the Formula (IB):

(IB)

12. A compound which is selected from the group consisting of:
(1R)-1-[(4-{[(5-chloro-6-methyl-3-pyridinyl)methyl]amino}-1-piperidinyl)methyl]-1,2-dihydro-4H,9H-imidazo[1,2,3-ij]-1,8-naphthyridine-4,9-dione;
(2R)-2-[(4-{[(5-chloro-6-methyl-3-pyridinyl)methyl]amino}-1-piperidinyl)methyl]-1,2-dihydro-3H,8H-2a,5,8a-triazaacenaphthylene-3,8-dione;
(1R)-1-{[4-({[6-(trifluoromethyl)-3-pyridinyl]methyl}amino)-1-piperidinyl]methyl}-1,2-dihydro-4H,9H-imidazo[1,2,3-ij]-1,8-naphthyridine-4,9-dione;
(2R)-2-[(4-{[(3,4-dichlorophenyl)methyl]amino}-1-piperidinyl)methyl]-1,2-dihydro-3H,8H-2a,5,8a-triazaacenaphthylene-3,8-dione;
(2R)-2-{[4-({[4-fluoro-3-(trifluoromethyl)phenyl]methyl}amino)-1-piperidinyl]methyl}-1,2-dihydro-3H,8H-2a,5,8a-triazaacenaphthylene-3,8-dione;
5-{[(1-{[(2R)-3,8-dioxo-1,2-dihydro-3H,8H-2a,5,8a-triazaacenaphthylen-2-yl]methyl}-4-piperidinyl)amino]methyl}-2-fluorobenzonitrile;
(2R)-2-[(4-{[(4-fluoro-3-methylphenyl)methyl]amino}-1-piperidinyl)methyl]-1,2-dihydro-3H,8H-2a,5,8a-triazaacenaphthylene-3,8-dione;
(1R)-1-[(4-{[(5-chloro-4-methyl-2-pyridinyl)methyl]amino}-1-piperidinyl)methyl]-1,2-dihydro-4H,9H-imidazo[1,2,3-ij]-1,8-naphthyridine-4,9-dione;
(1R)-1-[(4-{[(5-chloro-6-methyl-3-pyridinyl)methyl]amino}-1-piperidinyl)methyl]-1,2-dihydro-3H,8H-2a,5,8a-triazaacenaphthylene-3,8-dione;
(1R)-1-[(4-{[(5-bromo-6-methyl-3-pyridinyl)methyl]amino}-1-piperidinyl)methyl]-1,2-dihydro-4H,9H-imidazo[1,2,3-ij]-1,8-naphthyridine-4,9-dione;
(1R)-1-[(4-{[(5,6-dimethyl-3-pyridinyl)methyl]amino}-1-piperidinyl)methyl]-1,2-dihydro-4H,9H-imidazo[1,2,3-ij]-1,8-naphthyridine-4,9-dione;
2-[(4-{[(5,6-dimethyl-3-pyridinyl)methyl]amino}-1-piperidinyl)methyl]-1,2-dihydro-3H,8H-2a,5,8a-triazaacenaphthylene-3,8-dione;
2-[(4-{[(5,6-dichloro-3-pyridinyl)methyl]amino}-1-piperidinyl)methyl]-1,2-dihydro-3H,8H-2a,5,8a-triazaacenaphthylene-3,8-dione;
2-{[4-({[4-chloro-3-(trifluoromethyl)phenyl]methyl}amino)-1-piperidinyl]methyl}-1,2-dihydro-3H,8H-2a,5,8a-triazaacenaphthylene-3,8-dione;
2-{[4-({[6-(trifluoromethyl)-3-pyridazinyl]methyl}amino)-1-piperidinyl]methyl}-1,2-dihydro-3H,8H-2a,5,8a-triazaacenaphthylene-3,8-dione;
(1R)-1-{[4-({[6-(trifluoromethyl)-3-pyridazinyl]methyl}amino)-1-piperidinyl]methyl}-1,2-dihydro-4H,9H-imidazo[1,2,3-ij]-1,8-naphthyridine-4,9-dione;
2-{[4-({[6-(trifluoromethyl)-3-pyridinyl]methyl}amino)-1-piperidinyl]methyl}-1,2-dihydro-3H,8H-2a,5,8a-triazaacenaphthylene-3,8-dione;

2-[(4-{[(4-chlorophenyl)methyl]amino}-1-piperidinyl) methyl]-1,2-dihydro-3H,8H-2a,5,8a-triazaacenaphthylene-3,8-dione;
2-[(4-{[(3-chlorophenyl)methyl]amino}-1-piperidinyl) methyl]-1,2-dihydro-3H,8H-2a,5,8a-triazaacenaphthylene-3,8-dione;
2-[(4-{[(4-methyl-3-nitrophenyl)methyl]amino}-1-piperidinyl)methyl]-1,2-dihydro-3H,8H-2a,5,8a-triazaacenaphthylene-3,8-dione;
2-[(4-{[(5-bromo-4-methyl-2-thienyl)methyl]amino}-1-piperidinyl)methyl]-1,2-dihydro-3H,8H-2a,5,8a-triazaacenaphthylene-3,8-dione;
2-[(4-{[(3,4-dimethylphenyl)methyl]amino}-1-piperidinyl)methyl]-1,2-dihydro-3H,8H-2a,5,8a-triazaacenaphthylene-3,8-dione;
2-[(4-{[(5-chloro-6-methyl-3-pyridinyl)methyl]amino}-1-piperidinyl)methyl]-1,2-dihydro-3H,8H-2a,5,8a-triazaacenaphthylene-3,8-dione;
2-({4-[({4-[(trifluoromethyl)oxy]phenyl}methyl)amino]-1-piperidinyl}methyl)-1,2-dihydro-3H,8H-2a,5,8a-triazaacenaphthylene-3,8-dione;
2-{[4-({[4-(trifluoromethyl)phenyl]methyl}amino)-1-piperidinyl]methyl}-1,2-dihydro-3H,8H-2a,5,8a-triazaacenaphthylene-3,8-dione;
2-[(4-{[(4-bromophenyl)methyl]amino}-1-piperidinyl) methyl]-1,2-dihydro-3H,8H-2a,5,8a-triazaacenaphthylene-3,8-dione;
2-[(4-{[(5-chloro-6-methyl-3-pyridinyl)methyl]amino}-1-piperidinyl)methyl]-1,2-dihydro-3H,8H-2a,5,8a-triazaacenaphthylene-3,8-dione;
(1R)-1-[(4-{[(3,4-dichlorophenyl)methyl]amino}-1-piperidinyl)methyl]-1,2-dihydro-4H,9H-imidazo[1,2,3-ij]-1,8-naphthyridine-4,9-dione;
5-{[(1-{[(1R)-4,9-dioxo-1,2-dihydro-4H,9H-imidazo[1,2,3-ij]-1,8-naphthyridin-1-yl]methyl}-4-piperidinyl) amino]methyl}-3-methyl-2-pyridinecarbonitrile;
2-[(4-{[(6-fluoro-5-methyl-3-pyridinyl)methyl]amino}-1-piperidinyl)methyl]-1,2-dihydro-3H,8H-2a,5,8a-triazaacenaphthylene-3,8-dione;
2-[(4-{[(4-chloro-3-methylphenyl)methyl]amino}-1-piperidinyl)methyl]-1,2-dihydro-3H,8H-2a,5,8a-triazaacenaphthylene-3,8-dione;
2-[(4-{[(4-bromo-2-thienyl)methyl]amino}-1-piperidinyl)methyl]-1,2-dihydro-3H,8H-2a,5,8a-triazaacenaphthylene-3,8-dione;
2-[(4-{[(3,4-dichlorophenyl)methyl]amino}-1-piperidinyl)methyl]-1,2-dihydro-3H,8H-2a,5,8a-triazaacenaphthylene-3,8-dione;
2-[(4-{[(2-chloro-1,3-thiazol-5-yl)methyl]amino}-1-piperidinyl)methyl]-1,2-dihydro-3H,8H-2a,5,8a-triazaacenaphthylene-3,8-dione;
2-[(4-{[(4-nitrophenyl)methyl]amino}-1-piperidinyl)methyl]-1,2-dihydro-3H,8H-2a,5,8a-triazaacenaphthylene-3,8-dione;
2-{[4-({[3-chloro-4-(methyloxy)phenyl]methyl}amino)-1-piperidinyl]methyl}-1,2-dihydro-3H,8H-2a,5,8a-triazaacenaphthylene-3,8-dione;
2-[(4-{[(5-bromo-2-pyridinyl)methyl]amino}-1-piperidinyl)methyl]-1,2-dihydro-3H,8H-2a,5,8a-triazaacenaphthylene-3,8-dione;
2-[(4-{[(5-bromo-3-pyridinyl)methyl]amino}-1-piperidinyl)methyl]-1,2-dihydro-3H,8H-2a,5,8a-triazaacenaphthylene-3,8-dione;
2-[(4-{[(5-chloro-3-pyridinyl)methyl]amino}-1-piperidinyl)methyl]-1,2-dihydro-3H,8H-2a,5,8a-triazaacenaphthylene-3,8-dione;
2-[(4-{[(3-fluoro-4-methylphenyl)methyl]amino}-1-piperidinyl)methyl]-1,2-dihydro-3H,8H-2a,5,8a-triazaacenaphthylene-3,8-dione;
2-[(4-{[(3,4-difluorophenyl)methyl]amino}-1-piperidinyl)methyl]-1,2-dihydro-3H,8H-2a,5,8a-triazaacenaphthylene-3,8-dione;
(2R)-2-{[4-({[6-(trifluoromethyl)-3-pyridinyl] methyl}amino)-1-piperidinyl]methyl}-1,2-dihydro-3H,8H-2a,5,8a-triazaacenaphthylene-3,8-dione;
(2R)-2-{[4-({[6-(trifluoromethyl)-3-pyridinyl] methyl}amino)-1-piperidinyl]methyl}-1,2-dihydro-3H,8H-2a,5,8a-triazaacenaphthylene-3,8-dione hydrochloride;
(2S)-2-[(4-{[(3,4-dichlorophenyl)methyl]amino}-1-piperidinyl)methyl]-1,2-dihydro-3H,8H-2a,5,8a-triazaacenaphthylene-3,8-dione;
(2S)-2-{[4-({[6-(trifluoromethyl)-3-pyridinyl] methyl}amino)-1-piperidinyl]methyl}-1,2-dihydro-3H,8H-2a,5,8a-triazaacenaphthylene-3,8-dione;
3-chloro-5-{[(1-{[(1R)-4,9-dioxo-1,2-dihydro-4H,9H-imidazo[1,2,3-ij]-1,8-naphthyridin-1-yl]methyl}-4-piperidinyl)amino]methyl}-2-pyridinecarbonitrile;
3-chloro-5-{[(1-{[(1R)-4,9-dioxo-1,2-dihydro-4H,9H-imidazo[1,2,3-ij]-1,8-naphthyridin-1-yl]methyl}-4-piperidinyl)amino]methyl}-2-pyridinecarbonitrile dihydrochloride;
(2R)-2-[(4-{[(5-bromo-6-methyl-3-pyridinyl)methyl] amino}-1-piperidinyl)methyl]-1,2-dihydro-3H,8H-2a, 5,8a-triazaacenaphthylene-3,8-dione;
2-[(4-{[(5-fluoro-6-methyl-3-pyridinyl)methyl]amino}-1-piperidinyl)methyl]-1,2-dihydro-3H,8H-2a,5,8a-triazaacenaphthylene-3,8-dione;
(2S)-2-[(4-{[(5-chloro-6-methyl-3-pyridinyl)methyl] amino}-1-piperidinyl)methyl]-1,2-dihydro-3H,8H-2a, 5,8a-triazaacenaphthylene-3,8-dione;
(1R)-1-[(4-{[(6-ethyl-5-fluoro-3-pyridinyl)methyl] amino}-1-piperidinyl)methyl]-1,2-dihydro-4H,9H-imidazo[1,2,3-ij]-1,8-naphthyridine-4,9-dione;
(1R)-1-[(4-{[(5-bromo-6-methyl-3-pyridinyl)methyl] amino}-1-piperidinyl)methyl]-1,2-dihydro-3H,8H-2a, 5,8a-triazaacenaphthylene-3,8-dione hydrochloride;
(1R)-1-{[4-({[5-chloro-6-(hydroxymethyl)-3-pyridinyl] methyl}amino)-1-piperidinyl]methyl}-1,2-dihydro-4H,9H-imidazo[1,2,3-ij]-1,8-naphthyridine-4,9-dione;
2-{[4-({[4-methyl-3-(methyloxy)phenyl]methyl}amino)-1-piperidinyl]methyl}-1,2-dihydro-3H,8H-2a,5,8a-triazaacenaphthylene-3,8-dione;
(1R)-1-{[4-({[6-(Trifluoromethyl)-3-pyridinyl] methyl}amino)-1-piperidinyl]methyl}-1,2-dihydro-4H,9H-imidazo[1,2,3-ij]-1,8-naphthyridine-4,9-dione hydrochloride;
(1R)-1-{[4-({[5-methyl-6-(trifluoromethyl)-3-pyridinyl] methyl}amino)-1-piperidinyl]methyl}-1,2-dihydro-4H,9H-imidazo[1,2,3-ij]-1,8-naphthyridine-4,9-dione;
(1R)-1-{[4-({[5-bromo-6-(trifluoromethyl)-3-pyridinyl] methyl}amino)-1-piperidinyl]methyl}-1,2-dihydro-4H,9H-imidazo[1,2,3-ij]-1,8-naphthyridine-4,9-dione;
(1R)-1-{[4-({[5-chloro-6-(1-hydroxy-1-methylethyl)-3-pyridinyl]methyl}amino)-1-piperidinyl]methyl}-1,2-dihydro-4H,9H-imidazo[1,2,3-ij]-1,8-naphthyridine-4, 9-dione;
(1R)-1-[(4-{[(5-fluoro-6-methyl-3-pyridinyl)methyl] amino}-1-piperidinyl)methyl]-1,2-dihydro-4H,9H-imidazo[1,2,3-ij]-1,8-naphthyridine-4,9-dione;
(1R)-1-{[4-({[3-chloro-4-(hydroxymethyl)phenyl] methyl}amino)-1-piperidinyl]methyl}-1,2-dihydro-4H,9H-imidazo[1,2,3-ij]-1,8-naphthyridine-4,9-dione;

3-chloro-5-{[(1-{[(2R)-3,8-dioxo-1,2-dihydro-3H,8H-2a, 5,8a-triazaacenaphthylen-2-yl]methyl}-4-piperidinyl) amino]methyl}-2-pyridinecarbonitrile dihydrochloride;

(2R)-2-[(4-{[(5,6-dichloro-3-pyridinyl)methyl]amino}-1-piperidinyl)methyl]-1,2-dihydro-3H,8H-2a,5,8a-triazaacenaphthylene-3,8-dione;

(2R)-2-{[4-({[5-chloro-6-(hydroxymethyl)-3-pyridinyl] methyl}amino)-1-piperidinyl]methyl}-1,2-dihydro-3H,8H-2a,5,8a-triazaacenaphthylene-3,8-dione;

(2-chloro-4-{[(1-{[(1R)-4,9-dioxo-1,2-dihydro-4H,9H-imidazo[1,2,3-ij]-1,8-naphthyridin-1-yl]methyl}-4-piperidinyl)amino]methyl}phenyl)methyl acetate;

(1R)-1-{[4-({[5-chloro-6-(1-hydroxyethyl)-3-pyridinyl] methyl}amino)-1-piperidinyl]methyl}-1,2-dihydro-4H,9H-imidazo[1,2,3-ij]-1,8-naphthyridine-4,9-dione;

(1R)-1-[(4-{[(6-chloro-5-methyl-3-pyridazinyl)methyl] amino}-1-piperidinyl)methyl]-1,2-dihydro-4H,9H-imidazo[1,2,3-ij]-1,8-naphthyridine-4,9-dione;

(1R)-1-[(4-{[(6-chloro-5-methyl-3-pyridinyl)methyl] amino}-1-piperidinyl)methyl]-1,2-dihydro-4H,9H-imidazo[1,2,3-ij]-1,8-naphthyridine-4,9-dione; and (2R)-2-{[4-({[5-methyl-6-(trifluoromethyl)-3-pyridinyl] methyl}amino)-1-piperidinyl]methyl}-1,2-dihydro-3H,8H-2a,5,8a-triazaacenaphthylene-3,8-dione hydrochloride.

13. The compound of claim 12 which is (1R)-1-[(4-{[(5-chloro-6-methyl-3-pyridinyl)methyl]amino}-1-piperidinyl) methyl]-1,2-dihydro-4H,9H-imidazo[1,2,3-ij]-1,8-naphthyridine-4,9-dione.

14. The compound of claim 12 which is (2R)-2-[(4-{[(5-chloro-6-methyl-3-pyridinyl)methyl]amino}-1-piperidinyl) methyl]-1,2-dihydro-3H,8H-2a,5,8a-triazaacenaphthylene-3,8-dione.

15. The compound of claim 12 which is (1R)-1-{[4-({[6-(trifluoromethyl)-3-pyridinyl]methyl}amino)-1-piperidinyl] methyl}-1,2-dihydro-4H,9H-imidazo[1,2,3-ij]-1,8-naphthyridine-4,9-dione.

16. A pharmaceutical composition comprising a compound of claim 1, and one or more pharmaceutically acceptable carriers, excipients or diluents.

17. A method of treatment of tuberculosis in mammals, which method comprises the administration to a mammal in need of such treatment an effective amount of a compound of claim 1.

18. A method of treatment of tuberculosis in mammals which method comprises the administration to a mammal in need of such treatment a composition comprising a) the compound of claim 1 or a pharmaceutically acceptable salt thereof or N-oxide thereof; and b) one or more pharmaceutically acceptable carriers, excipients, or diluents.

19. A process for preparing the compound of claim 1 which comprises contacting under nucleophilic displacement or reductive amination conditions an amine compound of Formula (IIA) and a compound of Formula (IIB):

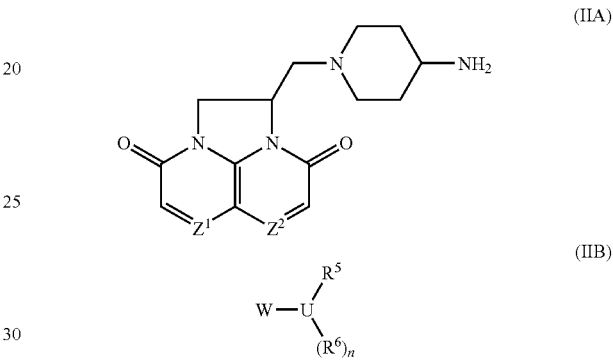

wherein W is an aldehyde moiety —CH=O when the reaction is carried out under reductive amination conditions or W is —CH$_2$Br when the reaction is carried out under nucleophilic displacement conditions.

* * * * *